(12) United States Patent
Bourn et al.

(10) Patent No.: US 8,481,685 B2
(45) Date of Patent: Jul. 9, 2013

(54) MODIFIED DNA POLYMERASES

(75) Inventors: William Bourn, Western Cape (ZA); Bjarne Faurholm, Western Cape (ZA); John Foskett, Western Cape (ZA)

(73) Assignee: Kapa Biosystems, Woburn, MA (US)

( * ) Notice: Subject to any disclaimer, the term of this patent is extended or adjusted under 35 U.S.C. 154(b) by 161 days.

(21) Appl. No.: 13/127,425

(22) PCT Filed: Nov. 3, 2009

(86) PCT No.: PCT/US2009/063169
§ 371 (c)(1),
(2), (4) Date: Jul. 19, 2011

(87) PCT Pub. No.: WO2010/062779
PCT Pub. Date: Jun. 3, 2010

(65) Prior Publication Data
US 2011/0269211 A1    Nov. 3, 2011

Related U.S. Application Data

(60) Provisional application No. 61/110,883, filed on Nov. 3, 2008.

(51) Int. Cl.
*C12P 21/08* (2006.01)
*C12N 9/00* (2006.01)
*C12N 9/10* (2006.01)
*C12N 9/12* (2006.01)

(52) U.S. Cl.
USPC ......... 530/387.3; 435/183; 435/193; 435/194

(58) Field of Classification Search
None
See application file for complete search history.

(56) References Cited

U.S. PATENT DOCUMENTS 7,960,157 B2 * 6/2011 Borns ........................... 435/194

* cited by examiner

*Primary Examiner* — Suzanne M Noakes
*Assistant Examiner* — Jae W Lee
(74) *Attorney, Agent, or Firm* — Brenda Herschbach Jarrell; Fangli Chen; Choate, Hall & Stewart LLP

(57) ABSTRACT

The present invention provides, among other things, modified DNA polymerases containing amino acid alterations based on mutations identified in directed evolution experiments designed to select enzymes that are better suited for applications in recombinant DNA technologies.

7 Claims, 3 Drawing Sheets

```
                          10        20        30        40        50        60        70        80        90       100
                          |         |         |         |         |         |         |         |         |         |
                          ░░░░░░░░░░░░░░░░░░░░N-terminal domain░░░░░░░░░░░░░░░░░░░░
Kofu                      MASAILDTDYITEDGKPVIRIFKKENGEFKIEYDRTFEPYFYALLKDDSAIEEVKKITAERHGTVVTVKRVEKVQKRFLGRPVEVWKLYFTHPQDVPAIR
Pod                       ......V....E.....L....K...H....R..I....R...K........G....KI.RIVD....E....K.IT....LE......T..
P kodakaraensis (D29671.2) ~~~M..............................................................................................
P furiosus (D12983.1)     ~~~M..V....E.....L....K...H....R..I....R...K........G....KI.RIVD....E....K.IT....LE......T..
T gorgonarius (BD00950)   ~~~M.................T.D...N...I........P..D..........T.R.V.A...K......I....................
T zilligii (DQ336890)     ~~~M...A...........V...K....D...D...I........DI..........T.R.T.A.R.K..........................
T litoralis (M74198.1)    ~~~M.......K...I............L.PH.Q..I............I.A.KG....KT.R.LDAV..R......E......I.E......M.
P GB-D 'Deep Vent' (U00707.1) ~~~M...A.........I...........V....N.R..I.........Q.D..R........KI.RIIDA...R......I...R....E......
T 9N-7 (U47108.1)         ~~~M........N.....V....................D...V..K....K...A............I.......N................
T aggregans (Y13030)      ~~~M.......K...I............L.PH.Q..I............D.I.A.KG....KI.R.VDAV..K......D.....I.E......L.

110       120       130       140       150       160       170       180       190       200
                          |         |         |         |         |         |         |         |         |         |
                          ░░░░░░░░░░░░░░░░░░░░░░░░░░░░░░░░░░░░░░░5'-3' exo░░░░░░░░░░░░░░░░░░░░░░░░░░░░░░░░░░░░░░░░░
Kofu                      DKIREHPAVIDIYEYDIPTAKRYLIDKGLVPMEGDEELKMLAFDIETLYHEGEEFAEGPIIMISYADEEGARVITWKNVDLPYVDVVSTEREMIKRFLRV
Pod                       E.V......V..F................I....E....I..........GK....I......NE.K......I.....E...S...........I
P kodakaraensis (D29671.2) ..................................................................................................
P furiosus (D12983.1)     E.V......V..F................I....E....I..........GK....I......NE.K......I.....E...S...........I
T gorgonarius (BD00950)   ...K.....V................I........................................I.............K......K.
T zilligii (DQ336890)     .........V.............R..I......R............G...............I.....ES....K......K.
T litoralis (M74198.1)    G........V................I......L.......F....D..GK.E.I........E.......I.........N........VQ.
P GB-D 'Deep Vent' (U00707.1) .....S.....F................I......L............K...I......E.K......KI.....E...S..........K.
T 9N-7 (U47108.1)         .R..A....V................I......T............GT.........GSE......KI...........K..........
T aggregans (Y13030)      G........................I........IM......F...D..GK.E.I........E.......I.........N........VQI 210       220       230       240       250       260       270       280       290       300
                          |         |         |         |         |         |         |         |         |         |
                          ░░░░░░░░░░░░░░░░░░░░░░░░░░░░░░░░░░5'-3' exo░░░░░░░░░░░░░░░░░░░░░░░░░░░░░░░░░░░░░░░░░
Kofu                      VKEKDPDVLITYNGDNFDFAYLKKRCEKLGINFALGRDG~~SEPKIQRMGDRFAVEVKGRIHFDLYPVIRRTINLPTYTLEAVYEAVFGQPKEKVYAEEI
Pod                       IR.....IIV.....S...P..A..A....KLTI....~~....M..I..MT..........H..T............I..K.......D..
P kodakaraensis (D29671.2) ..................................~~..............................................................
P furiosus (D12983.1)     IR.....IIV.....S...P..A..A....KLTI....~~....M..I..MT..........H..T............I..K.......D..
T gorgonarius (BD00950)   ..........I.........S...VK.I....E.~~..............................I....................
T zilligii (DQ336890)     IQ....................S.T..VK.I.....~~................................T...I...............
T litoralis (M74198.1)    .........I.........IP..I..A....VRLV....KEHP..........S...I........F..V............L.KT.S.LG....
P GB-D 'Deep Vent' (U00707.1) IR......I.....S..IP..V..A....KLP......~~....M..L..MT...I..........H.............I..K.......H..
T 9N-7 (U47108.1)         .R...............E...K.T......~~...............................................K............
T aggregans (Y13030)      .R..............IP..I..A....VTLL....KEHP....H...S...I.......F..V............L.KT.S.LG....
```

FIG. 1

```
                                                                <<<<<<<<<<<<<<Mapped domain<<<<<<<<<<<<<<<<<<<<<<<<<<<
                              310       320       330       340       350       360       370       380       390       400
                                                  5'-3' exo    N-terminal domain            Pol x
Kofu                          TTAWETGENLERVARYSMEDAKVTYELGKEFLPMEAQLSRLVGQPLWDVSRSSTGNLVEWFLLRKAYERNEVAPNKPSEEEYQRRLRESYTGGFVKEPEK
Pod                           AK...S......K.....A...........I...I..S.....................L.....D.K.LA..~..Q..E..Y....R
P kodakaraensis (D29671.2)    ..................................I...I..S.....................L.....D.K.LA..~..Q..E..Y....R
P furiosus (D12983.1)         AK...S......K.....A...........I................................................................
T gorgonarius (ED00950)       AQ......G.....................F...........S.....................L.....D.R.LA..~...A..Y....R
T zilligii (DQ336890)         AR...S..G.....................F...........S.....................L.....D.R.LA..~A...A..Y.....
T litoralis (M74198.1)        AAI...E..SMKKL.Q......RA........F.....E.AK.I..SV.............Y...V..A...L......D.....K.....TT.L..Y.....
P GB-D 'Deep Vent' (U00707.1) AE.....KG.....K...........R..F..........................Y.......L.....D.R..E......A..Y.....
T 9N-7 (U47108.1)             AQ...S..G.................R..F..............I..S...................K...L.....D.R.LA..~..GG.A..Y....R
T aggregans (Y13030)          AAI...E..SMKKL.Q......RA........F.....E.AK.I..SV.............Y...V......L......D.....R.....TT.L..Y....R
                                                                          D343G    V356M            E377K    E386K
                                                                                                              E386V
                                                                                                  S376G <<<<<<<<<<<<<<Mapped domain<<<<<<<<<<<<<<<<<<<<<<<<<<<
                              410       420       430       440       450       460       470       480       490       500
Kofu                          GLWENIVYLDFRALYPSIIITHNVSPDTLNLEGCKNYDIAPQVGHKFCKDIPGFIPSLLGHLLEERQKIKTKMKETQDPIEKILLDYRQKAIKLLIANSFY
Pod                           ..........S............R...E..V.......R...F.........D.......K...A.I....RK......R...I....Y.
P kodakaraensis (D29671.2)    ..........S............R...E..V.......R...F.........D.......K...A.I....RK......R...I....Y.
P furiosus (D12983.1)         ..........................................................................................
T gorgonarius (ED00950)       ..........S............R...EE..V..........F.........D.......V.K..A.I....K.......R...I.....
T zilligii (DQ336890)         ........YKS............R...RE..V.......R...F.........D.......V.K..A.V....RK......R...I....Y.
T litoralis (M74198.1)        ......I....S.....V........EK.......V...I..YR...F......I..D.IAM..D.K...S.I.......KM......R.....Y.
P GB-D 'Deep Vent' (U00707.1) ..GL.S.....S...............RE..V..E........F.........KR..D...E..R....ASK.....KM......R...I....Y.
T 9N-7 (U47108.1)             ..D........S...............R...E..V..E........F.........D.......R..A.V..L..K......R...I.....
T aggregans (Y13030)          .....A.....S.....V........ER.......V...I..Y....F......I..E.ITM..E..K...A.I.......KM......R.V.....Y.
                                      R410E                V441I                                                 A494V <<<<<<<<<<<<<<Mapped domain<<<<<<<<<<<<<<<<<<<<<<<<<<<
                              510       520       530       540       550       560       570       580       590       600
                                                                                          Pol I
Kofu                          GYYGYAKARWYCKECAESVTAWGRKYIELVWKELEEKFGPKVLYIDTDGLYATIPGGESEEIKKKALEFLKYINAKLPGALELEYEGFYKRGFFVTKKKY
Pod                           .....R.............E..TMTI..I...Y....I.S....FF.....ADA.TV....M..V....S....L..................R.
P kodakaraensis (D29671.2)    .....R.............E..TMTI..I...Y....I.S....FF.....ADA.TV....M.................................
P furiosus (D12983.1)         ..............................................................V....S....L..................R.
T gorgonarius (ED00950)       ....T.....Y......G....E...TTIR.I..........A...FF.....ADA.TV....K...D.........L.................
T zilligii (DQ336890)         ......N.....R..........Q...TTMR.I..........A...FF.....ADA.TV....K...N..PR....L......R..........
T litoralis (M74198.1)        .M..P.....S............H...MTIR.I..........A...F.....EKP.L....K...N..S....L..........L.......R.
P GB-D 'Deep Vent' (U00707.1) ....................E...F.R.....................AKP...........VD.....L..........V.............
T 9N-7 (U47108.1)             ....................E...M.IR..........A....H.....ADA.TV....K....P....L..........V.............
T aggregans (Y13030)          .M..P.....S............H...MTI..I..........A...F.....EKP.T....K.......S....L..........L......A.R.
                                                                           A550V                     E582K    F591L
                                                                                                              F591I
```

CONTINUATION OF FIG. 1

```
                              610       620       630       640       650       660       670       680       690       700
Kofu                      AVIDEEGKITTRGLEIVRRDWSEIAKETQARVIEALLKDGDVEKAVRIVKEVTEKLSKYEVPPEKLVIHEQITRDLKDYKATGPHVAVAKRIAARGVKIR
Pod                       ........VI.............TI..H...E.......IQ..AN..I.....A.Y....P.EE..I.......K...K...K
P kodakaraensis (D29671.2) ..........................................................................................
P furiosus (D12983.1)     ........VI.............TI..H...E.......IQ..AN..I.....A.Y....P.EE..I.......K...K...K
T gorgonarius (BD00950)   .....D.................I..H...E......................Y..........................I...
T zilligii (DQ336890)     .....D.................I..H...E.............R........Y......R..R................I...
T litoralis (M74198.1)    .......R......V..........K....I..E.S....EV.RD.V..IA..R..L..................I......I......I.VK
P GB-D 'Deep Vent' (U00707.1) .L......I............K....I..H.N..E..K.............I.....Y....P.EE..I..............V.
T 9N-7 (U47108.1)         ...........................I..H...E.........................R..........................
T aggregans (Y13030)      .......R......V..........K....I..EDS....E..D.V.EIA..Q..L.......K..SE...I.....I......K.I.V.
                                                       G636Y         E652X         E668Y      A679Y
                                                       G636R                                  A679I
                                                                                                E680I 710       720       730       740       750       760       770       780
Kofu                      PGTVISYIVLKGSGRIGDRAIPFDEFDPTKHKYDAEYYIENQVLPAVERILRAFGYRKEDLRYQKTRQVGLSAWLKPKGT*~ (SEQ ID NO:16)
Pod                       ..M..G....R.D.P.SN...LAE.Y..K...............L...EG.................TS..NI.KS*~ (SEQ ID NO:15)
P kodakaraensis (D29671.2) ................................................................................*~ (SEQ ID NO:11)
P furiosus (D12983.1)     ..M..G....R.D.P.SN...LAE.Y..K...............L...EG.................TS..NI.KS*~ (SEQ ID NO:9)
T gorgonarius (BD00950)   ......................A...................................G......T*~~ (SEQ ID NO:18)
T zilligii (DQ336890)     ..........P..V...........A..R.................................K.A..G......T*~~ (SEQ ID NO:19)
T litoralis (M74198.1)    ...I........K.S..V.LLT.Y..R.....PD..........L...E.............SSK.T..D....R*~~~~ (SEQ ID NO:20)
P GB-D 'Deep Vent' (U00707.1) ..M..G....R.D.P.SK...LAE...LR................L...E.........W...K.T..T...NI.KK*~ (SEQ ID NO:21)
T 9N-7 (U47108.1)         ..............A......R..................K...............K......G....V..KK* (SEQ ID NO:22)
T aggregans (Y13030)      ...I......R..K.S..V.LLS.Y..K.....PD..........L...E........K..SSK...D....K*~~~~ (SEQ ID NO:23)
                                                    E734K         E752Y         W772R
                                                    E734G         E752S
                                                    E734N
                                                     E738G
```

CONTINUATION OF FIG. 1

SEQUENCE LISTING

```
<160> NUMBER OF SEQ ID NOS: 26

<210> SEQ ID NO 1
<211> LENGTH: 2328
<212> TYPE: DNA
<213> ORGANISM: Pyrococcus furiosus

<400> SEQUENCE: 1
atgattttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacggggga aaggcatgga     180
aagattgtga gaattgttga tgtagagaag gttgagaaaa gtttctcgg caagcctatt      240 accgtgtgga aactttattt ggaacatccc caagatgttc ccactattag agaaaaagtt     300
agagaacatc cagcagttgt ggacatcttc gaatacgata ttccatttgc aaagagatac     360
ctcatcgaca aaggcctaat accaatggag ggggaagaag agctaaagat tcttgccttc     420
gatatagaaa ccctctatca cgaaggagaa gagtttggaa aaggcccaat tataatgatt     480
agttatgcag atgaaaatga agcaaaggtg attacttgga aaaacataga tcttccatac     540
gttgaggttg tatcaagcga gagagagatg ataaagagat ttctcaggat tatcagggag     600
aaggatcctg acattatagt tacttataat ggagactcat tcgacttccc atatttagcg     660
aaaagggcag aaaaacttgg gattaaatta accattggaa gagatggaag cgagcccaag     720
atgcagagaa taggcgatat gacggctgta gaagtcaagg gaagaataca tttcgacttg     780
tatcatgtaa taacaaggac aataaatctc ccaacataca cactagaggc tgtatatgaa     840 gcaattttg gaaagccaaa ggagaaggta tacgccgacg agatagcaaa agcctgggaa     900
agtggagaga accttgagag agttgccaaa tactcgatgg aagatgcaaa ggcaacttat     960
gaactcggga aagaattcct tccaatgaa attcagcttt caagattagt tggacaacct    1020
ttatgggatg tttcaaggtc aagcacaggg aaccttgtag agtggttctt acttaggaaa    1080
gcctacgaaa gaaacgaagt agctccaaac aagccaagtg aagaggagta tcaaagaagg    1140
ctcagggaga gctacacagg tggattcgtt aaagagccag aaaaggggtt gtgggaaaac    1200
```

```
atagtataccc tagatttttag agccctatat ccctcgatta taattaccca caatgtttct   1260
cccgatactc taaatcttga gggatgcaag aactatgata tcgctcctca agtaggccac   1320
aagttctgca aggacatccc tggttttata ccaagtctct tgggacattt gttagaggaa   1380
agacaaaaga ttaagacaaa aatgaaggaa actcaagatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg gggaagaaag   1560
tacatcgagt tagtatggaa ggagctcgaa gaaaagtttg gatttaaagt cctctacatt   1620
gacactgatg gtctctatgc aactatccca ggaggagaaa gtgaggaaat aaagaaaaag   1680
gctctagaat ttgtaaaata cataaaattca aagctccctg gactgctaga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acgagatgt tgaagaagct   1920 gtgagaatag taaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca ttgagaacca ggttcttcca   2220
gcggtactta ggatattgga gggatttgga tacagaaagg aagacctcag ataccaaaag   2280
acaagacaag tcggcctaac ttcctggctt aacattaaaa aatcctag            2328

<210> SEQ ID NO 2
<211> LENGTH: 2325
<212> TYPE: DNA
<213> ORGANISM: Thermococcus sp.

<400> SEQUENCE: 2
atgatcctcg acactgacta cataaccgag gatggaaagc ctgtcataag aattttcaag     60
aaggaaaacg gcgagtttaa gattgagtac gaccggactt ttgaacccta cttctacgcc    120
ctcctgaagg acgattctgc cattgaggaa gtcaagaaga taaccgccga gaggcacggg    180
acggttgtaa cggttaagcg ggttgaaaag gttcagaaga agttcctcgg agaccagtt    240 gaggtctgga aactctactt tactcatccg caggacgtcc cagcgataag ggacaagata    300
cgagagcatc cagcagttat tgacatctac gagtacgaca taccttcgc caagcgctac    360 ctcatagaca aggattagt gccaatggaa ggcgacgagg agctgaaaat gctcgccttc    420
gacattgaaa ctctctacca tgagggcgag gagttcgccg aggggccaat ccttatgata    480
agctacgccg acgaggaagg ggccagggtg ataacttgga agaacgtgga tctcccctac    540
gttgacgtcg tctcgacgga gagggagatg ataaagcgct tcctccgtgt tgtgaaggag    600
aaagacccgg acgttctcat aacctacaac ggcgacaact tcgacttcgc ctatctgaaa    660
aagcgctgtg aaaagctcgg aataaacttc gccctcggaa gggatggaag cgagccgaag    720
attcagagga tgggcgacag gtttgccgtc gaagtgaagg gacggataca cttcgatctc    780
tatcctgtga taagacggac gataaacctg cccacataca cgcttgaggc cgtttatgaa    840
gccgtcttcg gtcagccgaa ggagaaggtt tacgctgagg aaataaccac agcctgggaa    900
accggcgaga accttgagag agtcgcccgc tactcgatgg aagatgcgaa ggtcacatac    960
gagcttggga aggagttcct tccgatggag gcccagcttt ctcgcttaat cggccagtcc   1020
```

-continued

| | |
|---|---|
| ctctgggacg tctcccgctc cagcactggc aacctcgttg agtggttcct cctcaggaag | 1080 |
| gcctatgaga ggaatgagct ggccccgaac aagcccgatg aaaaggagct ggccagaaga | 1140 |
| cggcagagct atgaaggagg ctatgtaaaa gagcccgaga gagggttgtg ggagaacata | 1200 |
| gtgtacctag attttagatc cctgtacccc tcaatcatca tcacccacaa cgtctcgccg | 1260 |
| gatacgctca acagagaagg atgcaaggaa tatgacgttg ccccacaggt cggccaccgc | 1320 |
| ttctgcaagg acttcccagg atttatcccg agcctgcttg agacctcct agaggagagg | 1380 |
| cagaagataa agaagaagat gaaggccacg attgacccga tcgagaggaa gctcctcgat | 1440 |
| tacaggcaga gggccatcaa gatcctggca aacagctact acggttacta cggctatgca | 1500 |
| agggcgcgct ggtactgcaa ggagtgtgca gagagcgtaa cggcctgggg aagggagtac | 1560 |
| ataacgatga ccatcaagga gatagaggaa aagtacggct taaggtaat ctacagcgac | 1620 |
| accgacggat tttttgccac aatacctgga gccgatgctg aaaccgtcaa aagaaggct | 1680 |
| atggagttcc tcaagtatat caacgccaaa cttccgggcg cgcttgagct cgagtacgag | 1740 |
| ggcttctaca acgcggctt cttcgtcacg aagaagaagt atgcggtgat agacgaggaa | 1800 |
| ggcaagataa caacgcgcgg acttgagatt gtgaggcgtg actggagcga gatagcgaaa | 1860 |
| gagacgcagg cgagggttct tgaagctttg ctaaggacg gtgacgtcga aaggccgtg | 1920 |
| aggatagtca agaagttac cgaaaagctg agcaagtacg aggttccgcc ggagaagctg | 1980 |
| gtgatccacg agcagataac gagggattta aaggactaca aggcaaccgg tccccacgtt | 2040 |
| gccgttgcca agaggttggc cgcgagagga gtcaaaatac gccctggaac ggtgataagc | 2100 |
| tacatcgtgc tcaagggctc tgggaggata ggcgacaggg cgataccgtt cgacgagttc | 2160 |
| gacccgacga agcacaagta cgacgccgag tactacattg agaaccaggt tctcccagcc | 2220 |
| gttgagagaa ttctgagagc cttcggttac cgcaaggaag acctgcgcta ccagaagacg | 2280 |
| agacaggttg gtttgagtgc ttggctgaag ccgaagggaa cttga | 2325 |

<210> SEQ ID NO 3
<211> LENGTH: 2328
<212> TYPE: DNA
<213> ORGANISM: Artificial Sequence
<220> FEATURE:
<223> OTHER INFORMATION: Pfu codon optimized nucleotide sequence

<400> SEQUENCE: 3

| | |
|---|---|
| atgattctgg atgtggacta tatcaccgaa gagggcaaac cggttatacg tttatttaag | 60 |
| aaagagaatg gtaaattcaa gatcgagcat gaccgcacgt tccgtccata catttacgcg | 120 |
| ttgcttcggg atgatagcaa aattgaggaa gtcaaaaaga tcaccgggga acgtcatgga | 180 |
| aaaatagtaa gaattgtgga cgttgaaaaa gtcgaaaaga aatttctggg caaaccgatc | 240 |
| actgtatgga agctctatct ggaacatcct caggatgtgc ccacaattcg agaaaaagtt | 300 |
| cgtgagcacc cagccgtcgt ggatatattt gaatatgaca tccctttgc aaaacgctac | 360 |
| ttaattgata aaggcctgat cccgatggag ggggaagaag aacttaaaat tctggctttt | 420 |
| gacatagaaa cgctctatca tgagggagaa gaatttggca aggtcccat cattatgatt | 480 |
| tcttacgcgg atgagaacga agccaaggta atcacttgga aaaatattga cctgccgtac | 540 |
| gttgaagtgg tcagttcaga gcgggaaatg attaaacgtt ttttacgcat cattagagag | 600 |
| aaagatccag atataatcgt tacatataac ggcgactcct tcgatttcc ttacctggca | 660 |
| aaacgagctg aaaaattggg tattaaactt accatcgggc gtgacggatc ggaaccgaaa | 720 |
| atgcaacgca ttggcgatat gacggcggta gaggtgaaag gtcggataca ctttgatctg | 780 |

```
tatcatgtca tcacccgtac tattaatctc cccacataca cgttagaagc cgtttatgag    840
gcaatattcg gcaagccgaa agaaaaagtg tacgctgacg aaatcgcgaa ggcatgggag    900
agcggcgaaa acctggagcg cgtagcaaaa tattctatgg aagatgctaa agcgacctac    960
gaattgggga agaatttct tccaatggaa attcagctga gtcgtttagt cggacaacct    1020
ctgtgggacg tttcacgctc ctcgactggc aatctcgtgg agtggttcct gttgagaaaa    1080
gcctatgaac gaaacgaagt agcaccgaat aaaccaagcg aggaagaata tcagcgtcgc    1140
cttcgcgagt cttacacagg tgggtttgtt aaggaaccgg agaaaggtct ttgggaaaac    1200
atcgtgtatt tagatttccg tgcgctgtac cccagtatta taatcaccca caatgtctca    1260
cctgacacgc tcaacttgga aggttgcaaa aattatgata ttgctccgca agttggacat    1320
aagttttgta agatattcc gggcttcatc ccgtccctgc ttggtcactt actgaagag    1380 cgccaaaaaa ttaagaccaa aatgaaagag actcaggatc ccattgaaaa gatcctgctc    1440
gattaccggc aaaaagccat taaattgctt gcaaactcgt tttatgggta ctatggctat    1500
gcgaaggctc gttggtactg caagaatgt gccgagagcg tgacagcatg gggtcgcaaa    1560
tatatagaat tagtatggaa ggagctggaa gaaaaattcg gattcaaagt cctgtacatc    1620
gatacggatg gcctctatgc gaccattcct ggtggggagt ctgaagaaat caagaaaaaa    1680
gccttggaat tcgttaagta cattaatagt aaattaccgg gactgcttga actggagtat    1740
gaaggcttct acaaaagagg ttttttcgtt actaagaaac gatatgccgt aatagatgaa    1800
gaggggaaag tcatcacacg tggcctcgag attgttcgcc gggactggtc agagatagca    1860
aaggaaacgc aggcgcgcgt gctcgaaacc atcttgaaac atggtgatgt gaggaagcc    1920 gtccgcattg ttaaagaggt gatccagaag ttagcaaact atgaaattcc accggaaaa    1980 ctggcgatat acgagcaaat cactcgtccc cttcacgaat ataaagctat tggacctcat    2040
gtagccgtcg cgaagaaact ggctgcaaaa ggcgttaaga taaaaccagg tatggtgatc    2100
gggtacattg tactccgcgg cgacggtccg atttccaata gagccatctt ggcggaggaa    2160
tatgatccta aaaagcataa atacgacgct gaatattaca ttgagaacca ggtcttgccg    2220
gcagttctgc ggatacttga aggatttggc tatcgtaaag aagatctgcg ctatcaaaag    2280
acgcgacagg tgggtctgac tagctggttg aatatcaaaa aatcgtaa                2328
```

<210> SEQ ID NO 4
<211> LENGTH: 2337
<212> TYPE: DNA
<213> ORGANISM: Artificial Sequence
<220> FEATURE:
<223> OTHER INFORMATION: Pfu codon optimized nucleotide sequence, extra
      9 nt in 5' area

<400> SEQUENCE: 4

```
atggctagcg ccattctgga tgtggactat atcaccgaag agggcaaacc ggttatacgt    60
ttatttaaga aagagaatgg taaattcaag atcgagcatg accgcacgtt ccgtccatac    120
atttacgcgt tgcttcggga tgatagcaaa attgaggaag tcaaaaagat caccggggaa    180
cgtcatggaa aaatagtaag aattgtggac gttgaaaaag tcgaaagaa atttctgggc    240 aaaccgatca ctgtatggaa gctctatctg aacatcctc aggatgtgcc cacaattcga    300
gaaaaagttc gtgagcaccc agccgtcgtg gatatatttg aatatgacat ccctttttgca    360 aaacgctact taattgataa aggcctgatc ccgatggagg gggaagaaga acttaaaatt    420
ctggcttttg acatagaaac gctctatcat gagggagaag aatttggcaa aggtcccatc    480
```

```
attatgattt cttacgcgga tgagaacgaa gccaaggtaa tcacttggaa aaatattgac    540
ctgccgtacg ttgaagtggt cagttcagag cgggaaatga ttaaacgttt tttacgcatc    600
attagagaga aagatccaga tataatcgtt acatataacg gcgactcctt cgattttcct    660
tacctggcaa aacgagctga aaaattgggt attaaactta ccatcgggcg tgacggatcg    720
gaaccgaaaa tgcaacgcat tggcgatatg acggcggtag aggtgaaagg tcggatacac    780
tttgatctgt atcatgtcat cacccgtact attaatctcc ccacatacac gttagaagcc    840
gtttatgagg caatattcgg caagccgaaa gaaaaagtgt acgctgacga aatcgcgaag    900
gcatgggaga gcggcgaaaa cctggagcgc gtagcaaaat attctatgga agatgctaaa    960
gcgacctacg aattggggaa agaatttctt ccaatggaaa ttcagctgag tcgtttagtc    1020
ggacaacctc tgtgggacgt ttcacgctcc tcgactggca atctcgtgga gtggttcctg    1080
ttgagaaaag cctatgaacg aaacgaagta gcaccgaata aaccaagcga ggaagaatat    1140
cagcgtcgcc ttcgcgagtc ttacacaggt gggtttgtta aggaaccgga gaaaggtctt    1200
tgggaaaaca tcgtgtattt agatttccgt gcgctgtacc ccagtattat aatcacccac    1260
aatgtctcac ctgacacgct caacttgaa ggttgcaaaa attatgatat tgctccgcaa    1320
gttggacata agttttgtaa agatattccg ggcttcatcc cgtccctgct tggtcactta    1380
ctggaagagc gccaaaaaat taagaccaaa atgaaagaga ctcaggatcc cattgaaaag    1440
atcctgctcg attaccggca aaaagccatt aaattgcttg caaactcgtt ttatgggtac    1500
tatggctatg cgaaggctcg ttggtactgc aaagaatgtg ccgagagcgt gacagcatgg    1560
ggtcgcaaat atatagaatt agtatggaag gagctggaag aaaaattcgg attcaaagtc    1620
ctgtacatcg atacgggtgg cctctatgcg accattcctg gtggggagtc tgaagaaatc    1680
aagaaaaaag ccttggaatt cgttaagtac attaatagta aattaccggg actgcttgaa    1740
ctggagtatg aaggcttcta caaagaggt ttttcgtta ctaagaaacg atatgccgta    1800
atagatgaag aggggaaagt catcacacgt ggcctcgaga ttgttcgccg ggactggtca    1860
gagatagcaa aggaaacgca ggcgcgcgtg ctcgaaacca tcttgaaaca tggtgatgta    1920
gaggaagccg tccgcattgt taagaggtg atccagaagt tagcaaacta tgaaattcca    1980
ccggaaaaac tggcgatata cgagcaaatc actcgtcccc ttcacgaata taagctatt    2040 ggacctcatg tagccgtcgc gaagaaactg gctgcaaaag cgttaagat aaaaccaggt    2100 atggtgatcg ggtacattgt actccgcggc gacggtccga ttcccaatag agccatcttg    2160
gcggaggaat atgatcctaa aaagcataaa tacgacgctg aatattacat tgagaaccag    2220
gtcttgccgg cagttctgcg gatacttgaa ggatttggct atcgtaaaga agatctgcgc    2280
tatcaaaaga cgcgacaggt gggtctgact agctggttga atatcaaaaa atcgtaa      2337

<210> SEQ ID NO 5
<211> LENGTH: 2325
<212> TYPE: DNA
<213> ORGANISM: Artificial Sequence
<220> FEATURE:
<223> OTHER INFORMATION: KOD codon optimized nucleotide sequence

<400> SEQUENCE: 5
atgattctgg ataccgacta tatcacggaa gatggcaaac cggtgatacg tattttttaag     60 aaagagaatg gtgagttcaa aatcgagtac gaccgcactt ttgagccata tttctacgcg    120
ttactgaagg acgatagcgc cattgaagaa gttaaaaaaa tcaccgcaga gcggcatggg    180
acagtggtaa ccgtgaagag agttgaaaaa gtccagaaaa aattttttggg acgacctgta    240
```

```
gaagtgtgga aactttattt cactcacccc caagatgttc cggctatacg tgataaaatt    300
cgcgaacatc cagcggtcat tgatatttac gaatatgata tacctttgc caagcgttac    360 ctcatcgaca aaggcctggt gccgatggaa ggtgatgaag aattaaaaat gttggcattc    420
gacattgaaa cactttatca cgagggggaa gagtttgctg agggtcccat cctgatgatt    480
tcttatgcgg atgaagaggg tgcccgcgta ataacctgga gaacgttga tctcccgtac    540 gtggacgtcg ttagtacgga acgggaaatg atcaaacgtt tcctgcgcgt agtgaaagag    600
aaagatccag acgtcttaat tacctataat ggtgataact ttgattttgc atacctgaaa    660
aaaagatgcg aaaagttggg cataaatttc gctcttggtc gagacgggtc agagcctaaa    720
atccagcgta tgggagatcg cttttgcggtt gaagtgaaag gccggattca tttcgacctg    780
tatccggtaa ttcgtcgcac tatcaacctc cccacataca cgttagaagc cgtctatgag    840
gcagtttttg gtcaaccgaa ggaaaaagtt tacgctgagg aaattaccac tgcgtgggaa    900
acaggcgaga atctggaacg tgtagcccgc tattctatgg aggatgcaaa agttacctat    960
gaattgggta aggaatttct tccaatggag gcgcagctgt cgagattaat agggcagagc   1020
ctgtgggacg tgtctcgaag ttcaacggga aacctcgtcg aatggtttct gttgcggaaa   1080
gcatacgagc gtaatgaact tgcccctaac aaaccggatg aaaaggagct ggcacgccgt   1140
cgccaatcct atgaaggcgg ttacgttaaa gaaccagagc gggggttatg ggaaaatatc   1200
gtgtatctgg atttccgttc gctctacccg agcattatca ttacccacaa cgtatctccc   1260
gacactttga atcgcgaggg ctgtaaagaa tatgatgtcg cgccgcaggt tggtcataga   1320
ttttgcaagg acttcccggg atttatacca agtctgcttg gcgatttact ggaagagcga   1380
caaaaaatca aaagaaaat gaaagctaca atcgatccga tagaacgtaa gctgctcgac   1440
taccgccagc gggccatcaa aattttggca aactcatatt atggttacta tgggtacgcg   1500
cgtgctcgct ggtattgtaa agagtgcgcc gaatccgtga cggcatgggg ccgtgaatac   1560
atcaccatga ctattaagga gatagaagag aaatatggtt caaagtaat ctactcggat   1620 acagacggat tctttgcgac gattcccggt gccgatgcag aaaccgtcaa gaaaaaagcg   1680
atggaattcc ttaagtatat aaatgctaaa ttacctggtg ccctggagct ggaatacgaa   1740
gggttttaca acgcggatt ctttgttact aagaaaaaat atgcggtgat cgacgaggaa   1800
ggcaagatta cgaccagagg cctcgagatt gtacggcgtg attggagcga aatcgctaaa   1860
gaaacacagg cacgtgtctt ggaggcatta ctgaaagatg gggacgttga aaaggcggtg   1920
cgaattgtaa agaagtcac cgaaaaactt tctaagtacg aagttccgcc agagaaactg   1980
gtgatacacg aacaaatcac tcgtgatctg aaagactata aggctacagg cccgcatgta   2040
gcagtcgcca aacgcctcgc ggctcggggt gttaaaattc gtcccggaac ggtgatcagt   2100
tacattgtat tgaagggctc aggtcgcata ggggatagag caatcccttt cgacgagttt   2160
gatccaacca aacacaaata tgatgccgaa tactatattg aaaaccaggt cttgccggcg   2220
gttgagcgta tactgcgcgc tttcggctat cgaaggaag atcttcgtta ccaaaaaact   2280
agacaggtgg gtctgtccgc atggctcaaa cctaagggaa cgtaa                   2325
```

<210> SEQ ID NO 6  
<211> LENGTH: 2334  
<212> TYPE: DNA  
<213> ORGANISM: Artificial Sequence  
<220> FEATURE:  
<223> OTHER INFORMATION: KOD codon optimized nucleotide sequence, extra 9 nt in 5' area.

<400> SEQUENCE: 6

```
atggctagcg ccattctgga taccgactat atcacggaag atggcaaacc ggtgatacgt       60
atttttaaga aagagaatgg tgagttcaaa atcgagtacg accgcacttt tgagccatat      120
ttctacgcgt tactgaagga cgatagcgcc attgaagaag ttaaaaaaat caccgcagag      180
cggcatggga cagtggtaac cgtgaagaga gttgaaaaag tccagaaaaa attttttggga     240
cgacctgtag aagtgtggaa actttatttc actcaccccc aagatgttcc ggctatacgt     300
gataaaattc gcgaacatcc agcggtcatt gatatttacg aatatgatat accttttgcc     360
aagcgttacc tcatcgacaa aggcctggtg ccgatggaag gtgatgaaga attaaaaatg     420
ttggcattcg acattgaaac actttatcac gaggggaag agtttgctga gggtcccatc      480
ctgatgattt cttatgcgga tgaagagggt gcccgcgtaa taacctggaa gaacgttgat     540
ctcccgtacg tggacgtcgt tagtacgaaa cgggaaatga tcaaacgttt cctgcgcgta    600
gtgaaagaga aagatccaga cgtcttaatt acctataatg gtgataactt tgattttgca     660
tacctgaaaa aagatgcga aaagttgggc ataaatttcg ctcttggtcg agacgggtca      720
gagcctaaaa tccagcgtat gggagatcgc tttgcggttg aagtgaaagg ccggattcat     780
ttcgacctgt atccggtaat tcgtcgcact atcaacctcc ccacatacac gttagaagcc     840
gtctatgagg cagttttggg tcaaccgaag gaaaaagttt acgctgagga aattaccact      900
gcgtgggaaa caggcgagaa tctggaacgt gtagcccgct attctatgga ggatgcaaaa    960
gttacctatg aattgggtaa ggaatttctt ccaatggagg cgcagctgtc gagattaata    1020
gggcagagcc tgtgggacgt gtctcgaagt tcaacgggaa acctcgtcga atggtttctg    1080
ttgcggaaag catacgagcg taatgaactt gcccctaaca aaccggatga aaaggagctg   1140
gcacgccgtc gccaatccta tgaaggcggt tacgttaaag aaccagagcg ggggttatgg   1200
gaaaatatcg tgtatctgga tttccgttcg ctctacccga gcattatcat tacccacaac  1260
gtatctcccg acactttgaa tcgcgagggc tgtaaagaat atgatgtcgc gccgcaggtt   1320
ggtcatagat tttgcaagga cttcccggga tttataccaa gtctgcttgg cgatttactg   1380
gaagagcgac aaaaaatcaa aaagaaaatg aaagctacaa tcgatccgat agaacgtaag   1440
ctgctcgact accgccagcg ggccatcaaa attttggcaa actcatatta tggttactat   1500
gggtacgcgc gtgctcgctg gtattgtaaa gagtgcgccg aatccgtgac ggcatggggc    1560
cgtgaataca tcaccatgac tattaaggag atagaagaga aatatggttt caaagtaatc   1620
tactcggata cagacggatt ctttgcgacg attcccggtg ccgatgcaga aaccgtcaag    1680
aaaaaagcga tggaattcct taagtatata aatgctaaat tacctggtgc cctggagctg    1740
gaatacgaag ggttttacaa acgcggattc tttgttacta agaaaaaata tgcggtgatc    1800
gacgaggaag gcaagattac gaccagaggc ctcgagattg tacggcgtga ttggagcgaa    1860
atcgctaaag aaacacaggc acgtgtcttg gaggcattac tgaaagatgg ggacgttgaa    1920
aaggcggtgc gaattgtaaa agaagtcacc gaaaaacttt ctaagtacga agttccgcca    1980
gagaaactgg tgatacacga acaaatcact cgtgatctga aagactataa ggctacaggc    2040
ccgcatgtag cagtcgccaa acgcctcgcg gctcggggtg ttaaaattcg tcccggaacg   2100
gtgatcagtt acattgtatt gaagggctca ggtcgcatag gggatagagc aatccctttc   2160
gacgagtttg atccaaccaa acacaaatat gatgccgaat actatattga aaaccaggtc   2220
ttgccggcgg ttgagcgtat actgcgcgct ttcggctatc gaaggaaga tcttcgttac   2280
caaaaaacta gacaggtggg tctgtccgca tggctcaaac ctaagggaac gtaa         2334
```

```
<210> SEQ ID NO 7
<211> LENGTH: 5017
<212> TYPE: DNA
<213> ORGANISM: Artificial Sequence
<220> FEATURE:
<223> OTHER INFORMATION: pKB13 - Pfu codon optimized nucleotide sequence
      in pUC19 vector

<400> SEQUENCE: 7
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cggtctcagc gccattctgg    420
ataccgacta tatcacggaa gatggcaaac cggtgatacg tattttttaag aaagagaatg    480 gtgagttcaa aatcgagtac gaccgcactt ttgagccata tttctacgcg ttactgaagg    540
acgatagcgc cattgaagaa gttaaaaaaa tcaccgcaga gcggcatggg acagtggtaa    600
ccgtgaagag agttgaaaaa gtccagaaaa aattttttggg acgacctgta gaagtgtgga    660
aactttattt cactcacccc caagatgttc cggctatacg tgataaaatt cgcgaacatc    720
cagcggtcat tgatatttac gaatatgata taccttttgc caagcgttac ctcatcgaca    780
aaggcctggt gccgatggaa ggtgatgaag aattaaaaat gttggcattc gacattgaaa    840
cactttatca cgagggggaa gagtttgctg agggtcccat cctgatgatt tcttatgcgg    900
atgaagaggg tgcccgcgta ataacctgga agaacgttga tctcccgtac gtggacgtcg    960
ttagtacgga acgggaaatg atcaaacgtt cctgcgcgt agtgaaagag aaagatccag   1020
acgtcttaat tacctataat ggtgataact ttgattttgc atacctgaaa aaaagatgcg   1080
aaaagttggg cataaatttc gctcttggtc gagacgggtc agagcctaaa atccagcgta   1140
tgggagatcg ctttgcggtt gaagtgaaag gccggattca tttcgacctg tatccggtaa   1200
ttcgtcgcac tatcaacctc cccacataca cgttagaagc cgtctatgag gcagttttg    1260 gtcaaccgaa ggaaaaagtt tacgctgagg aaattaccac tgcgtgggaa acaggcgaga   1320
atctggaacg tgtagcccgc tattctatgg aggatgcaaa agttacctat gaattgggta   1380
aggaatttct tccaatggag gcgcagctgt cgagattaat agggcagagc ctgtgggacg   1440
tgtctcgaag ttcaacggga aacctcgtcg aatggtttct gttgcggaaa gcatacgagc   1500
gtaatgaact tgcccctaac aaaccggatg aaaaggagct ggcacgccgt cgccaatcct   1560
atgaaggcgg ttacgttaaa gaaccagagc gggggttatg ggaaaatatc gtgtatctgg   1620
atttccgttc gctctacccg agcattatca ttacccacaa cgtatctccc gacactttga   1680
atcgcgaggg ctgtaaagaa tatgatgtcg cgccgcaggt tggtcataga ttttgcaagg   1740
acttcccggg atttataccag agtctgcttg gcgatttact ggaagagcga caaaaaatca   1800 aaagaaaat gaaagctaca atcgatccga tagaacgtaa gctgctcgac taccgccagc   1860
gggccatcaa aattttggca aactcatatt atggttacta tgggtacgcg cgtgctcgct   1920
ggtattgtaa agagtgcgcc gaatccgtga cggcatgggg ccgtgaatac atcaccatga   1980
ctattaagga gatagaagag aaatatggtt tcaaagtaat ctactcggat acagacggat   2040
tctttgcgac gattcccggt gccgatgcag aaaccgtcaa gaaaaagcg atggaattcc   2100
```

```
ttaagtatat aaatgctaaa ttacctggtg ccctggagct ggaatacgaa gggttttaca    2160
aacgcggatt ctttgttact aagaaaaaat atgcggtgat cgacgaggaa ggcaagatta    2220
cgaccagagg cctcgagatt gtacggcgtg attggagcga atcgctaaag aaacacagg     2280
cacgtgtctt ggaggcatta ctgaaagatg ggacgttga aaaggcggtg cgaattgtaa     2340
aagaagtcac cgaaaaactt tctaagtacg aagttccgcc agagaaactg gtgatacacg    2400
aacaaatcac tcgtgatctg aaagactata aggctacagg cccgcatgta gcagtcgcca    2460
aacgcctcgc ggctcggggt gttaaaattc gtcccggaac ggtgatcagt tacattgtat    2520
tgaagggctc aggtcgcata ggggatagag caatccctt cgacgagttt gatccaacca     2580
aacacaaata tgatgccgaa tactatattg aaaaccaggt cttgccggcg gttgagcgta    2640
tactgcgcgc tttcggctat cgaaaggaag atcttcgtta ccaaaaaact agacaggtgg    2700
gtctgtccgc atggctcaaa cctaagggaa cgtaatgata tgagaccgga tcctctagag    2760
tcgacctgca ggcatgcaag cttggcgtaa tcatggtcat agctgtttcc tgtgtgaaat    2820
tgttatccgc tcacaattcc acacaacata cgagccggaa gcataaagtg taaagcctgg    2880
ggtgcctaat gagtgagcta actcacatta attgcgttgc gctcactgcc cgcttttcag    2940
tcgggaaacc tgtcgtgcca gctgcattaa tgaatcggcc aacgcgcggg gagaggcggt    3000
ttgcgtattg ggcgctcttc cgcttcctcg ctcactgact cgctgcgctc ggtcgttcgg    3060
ctgcggcgag cggtatcagc tcactcaaag gcggtaatac ggttatccac agaatcaggg    3120
gataacgcag gaaagaacat gtgagcaaaa ggccagcaaa aggccaggaa ccgtaaaaag    3180
gccgcgttgc tggcgttttt ccataggctc cgcccccctg acgagcatca caaaaatcga    3240
cgctcaagtc agaggtggcg aaacccgaca ggactataaa gataccaggc gtttccccct    3300
ggaagctccc tcgtgcgctc tcctgttccg accctgccgc ttaccggata cctgtccgcc    3360
tttctccctt cgggaagcgt ggcgctttct catagctcac gctgtaggta tctcagttcg    3420
gtgtaggtcg ttcgctccaa gctgggctgt gtgcacgaac cccccgttca gcccgaccgc    3480
tgcgccttat ccggtaacta tcgtcttgag tccaacccgg taagacacga cttatcgcca    3540
ctggcagcag ccactggtaa caggattagc agagcgaggt atgtaggcgg tgctacagag    3600
ttcttgaagt ggtggcctaa ctacggctac actagaagaa cagtatttgg tatctgcgct    3660
ctgctgaagc cagttacctt cggaaaaaga gttggtagct cttgatccgg caaacaaacc    3720
accgctggta gcggtggttt ttttgtttgc aagcagcaga ttacgcgcag aaaaaaagga    3780
tctcaagaag atcctttgat cttttctacg ggtctgacg ctcagtggaa cgaaaactca    3840
cgttaaggga ttttggtcat gagattatca aaaaggatct tcacctagat ccttttaaat    3900
taaaaatgaa gttttaaatc aatctaaagt atatatgagt aaacttggtc tgacagttac    3960
caatgcttaa tcagtgaggc acctatctca gcgatctgtc tatttcgttc atccatagtt    4020
gcctgactcc ccgtcgtgta gataactacg atacgggagg gcttaccatc tggccccagt    4080
gctgcaatga taccgcgaga cccacgctca ccggctccag atttatcagc aataaaccag    4140
ccagccggaa gggccgagcg cagaagtggt cctgcaactt tatccgcctc catccagtct    4200
attaattgtt gccgggaagc tagagtaagt agttcgccag ttaatagttt gcgcaacgtt    4260
gttgccattg ctacaggcat cgtggtgtca cgctcgtcgt ttggtatggc ttcattcagc    4320
tccggttccc aacgatcaag gcgagttaca tgatccccca tgttgtgcaa aaaagcggtt    4380
agctccttcg gtcctccgat cgttgtcaga agtaagttgg ccgcagtgtt atcactcatg    4440
gttatggcag cactgcataa ttctcttact gtcatgccat ccgtaagatg cttttctgtg    4500
```

-continued

| | |
|---|---|
| actggtgagt actcaaccaa gtcattctga gaatagtgta tgcggcgacc gagttgctct | 4560 |
| tgcccggcgt caatacggga taataccgcg ccacatagca gaactttaaa agtgctcatc | 4620 |
| attggaaaac gttcttcggg gcgaaaactc tcaaggatct taccgctgtt gagatccagt | 4680 |
| tcgatgtaac ccactcgtgc acccaactga tcttcagcat cttttacttt caccagcgtt | 4740 |
| tctgggtgag caaaaacagg aaggcaaaat gccgcaaaaa agggaataag ggcgacacgg | 4800 |
| aaatgttgaa tactcatact cttccttttt caatattatt gaagcattta tcagggttat | 4860 |
| tgtctcatga gcggatacat atttgaatgt atttagaaaa ataaacaaat aggggttccg | 4920 |
| cgcacatttc cccgaaaagt gccacctgac gtctaagaaa ccattattat catgacatta | 4980 |
| acctataaaa ataggcgtat cacgaggccc tttcgtc | 5017 |

<210> SEQ ID NO 8
<211> LENGTH: 5017
<212> TYPE: DNA
<213> ORGANISM: Artificial Sequence
<220> FEATURE:
<223> OTHER INFORMATION: pKB8 - KOD codon optimized nucleotide sequence
      in pUC19 vector

<400> SEQUENCE: 8

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cggtctcagc gccattctgg | 420 |
| ataccgacta tatcacggaa gatggcaaac cggtgatacg tattttaag aaagagaatg | 480 |
| gtgagttcaa aatcgagtac gaccgcactt ttgagccata tttctacgcg ttactgaagg | 540 |
| acgatagcgc cattgaagaa gttaaaaaaa tcaccgcaga gcggcatggg acagtggtaa | 600 |
| ccgtgaagag agttgaaaaa gtccagaaaa aatttttggg acgacctgta gaagtgtgga | 660 |
| aactttattt cactcacccc caagatgttc cggctatacg tgataaaatt cgcgaacatc | 720 |
| cagcggtcat tgatatttac gaatatgata taccttttgc caagcgttac ctcatcgaca | 780 |
| aaggcctggt gccgatggaa ggtgatgaag aattaaaaat gttggcattc gacattgaaa | 840 |
| cactttatca cgaggggaa gagtttgctg agggtcccat cctgatgatt tcttatgcgg | 900 |
| atgaagaggg tgcccgcgta ataacctgga agaacgttga tctcccgtac gtggacgtcg | 960 |
| ttagtacgga acgggaaatg atcaaacgtt tcctgcgcgt agtgaaagag aaagatccag | 1020 |
| acgtcttaat tacctataat ggtgataact ttgattttgc atacctgaaa aaagatgcg | 1080 |
| aaaagttggg cataaatttc gctcttggtc gagacgggtc agagcctaaa atccagcgta | 1140 |
| tgggagatcg ctttgcggtt gaagtgaaag gccggattca tttcgacctg tatccggtaa | 1200 |
| ttcgtcgcac tatcaacctc cccacataca cgttagaagc cgtctatgag gcagtttttg | 1260 |
| gtcaaccgaa ggaaaaagtt tacgctgagg aaattaccac tgcgtgggaa acaggcgaga | 1320 |
| atctggaacg tgtagcccgc tattctatgg aggatgcaaa agttacctat gaattgggta | 1380 |
| aggaatttct tccaatggag gcgcagctgt cgagattaat agggcagagc ctgtgggacg | 1440 |
| tgtctcgaag ttcaacggga aacctcgtcg aatggtttct gttgcggaaa gcatacgagc | 1500 |
| gtaatgaact tgcccctaac aaaccggatg aaaaggagct ggcacgccgt cgccaatcct | 1560 |

```
atgaaggcgg ttacgttaaa gaaccagagc gggggttatg ggaaaatatc gtgtatctgg    1620
atttccgttc gctctacccg agcattatca ttacccacaa cgtatctccc gacactttga    1680
atcgcgaggc ctgtaaagaa tatgatgtcg cgccgcaggt tggtcataga ttttgcaagg    1740
acttcccggg atttatacca agtctgcttg gcgatttact ggaagagcga caaaaaatca    1800
aaaagaaaat gaaagctaca atcgatccga tagaacgtaa gctgctcgac taccgccagc    1860
gggccatcaa aattttggca aactcatatt atggttacta tgggtacgcg cgtgctcgct    1920
ggtattgtaa agagtgcgcc gaatccgtga cggcatgggg ccgtgaatac atcaccatga    1980
ctattaagga gatagaagag aaatatggtt tcaaagtaat ctactcggat acagacggat    2040
tctttgcgac gattcccggt gccgatgcag aaaccgtcaa gaaaaaagcg atggaattcc    2100
ttaagtatat aaatgctaaa ttacctggtg ccctggagct ggaatacgaa gggttttaca    2160
aacgcggatt ctttgttact aagaaaaaat atgcggtgat cgacgaggaa ggcaagatta    2220
cgaccagagg cctcgagatt gtacggcgtg attggagcga aatcgctaaa gaaacacagg    2280
cacgtgtctt ggaggcatta ctgaaagatg gggacgttga aaggcggtg cgaattgtaa    2340 aagaagtcac cgaaaaactt tctaagtacg aagttccgcc agagaaactg gtgatacacg    2400
aacaaatcac tcgtgatctg aaagactata aggctacagg cccgcatgta gcagtcgcca    2460
aacgcctcgc ggctcggggt gttaaaattc gtcccggaac ggtgatcagt tacattgtat    2520
tgaagggctc aggtcgcata ggggatagag caatcccttt cgacgagttt gatccaacca    2580
aacacaaata tgatgccgaa tactatattg aaaaccaggt cttgccggcg gttgagcgta    2640
tactgcgcgc tttcggctat cgaaaggaag atcttcgtta ccaaaaaact agacaggtgg    2700
gtctgtccgc atggctcaaa cctaagggaa cgtaatgata tgagaccgga tcctctagag    2760
tcgacctgca ggcatgcaag cttggcgtaa tcatggtcat agctgtttcc tgtgtgaaat    2820
tgttatccgc tcacaattcc acacaacata cgagccggaa gcataaagtg taaagcctgg    2880
ggtgcctaat gagtgagcta actcacatta attgcgttgc gctcactgcc cgctttccag    2940
tcgggaaacc tgtcgtgcca gctgcattaa tgaatcggcc aacgcgcggg gagaggcggt    3000
ttgcgtattg ggcgctcttc cgcttcctcg ctcactgact cgctgcgctc ggtcgttcgg    3060
ctgcggcgag cggtatcagc tcactcaaag gcggtaatac ggttatccac agaatcaggg    3120
gataacgcag gaaagaacat gtgagcaaaa ggccagcaaa aggccaggaa ccgtaaaaag    3180
gccgcgttgc tggcgttttt ccataggctc cgcccccctg acgagcatca caaaaatcga    3240
cgctcaagtc agaggtggcg aaacccgaca ggactataaa gataccaggc gtttccccct    3300
ggaagctccc tcgtgcgctc tcctgttccg accctgccgc ttaccggata cctgtccgcc    3360
tttctccctt cgggaagcgt ggcgctttct catagctcac gctgtaggta tctcagttcg    3420
gtgtaggtcg ttcgctccaa gctgggctgt gtgcacgaac cccccgttca gcccgaccgc    3480
tgcgccttat ccggtaacta tcgtcttgag tccaacccgg taagacacga cttatcgcca    3540
ctggcagcag ccactggtaa caggattagc agagcgaggt atgtaggcgg tgctacagag    3600
ttcttgaagt ggtggcctaa ctacggctac actagaagaa cagtatttgg tatctgcgct    3660
ctgctgaagc cagttacctt cggaaaaaga gttggtagct cttgatccgg caaacaaacc    3720
accgctggta gcggtggttt ttttgtttgc aagcagcaga ttacgcgcag aaaaaagga    3780 tctcaagaag atcctttgat cttttctacg gggtctgacg ctcagtggaa cgaaaactca    3840
cgttaaggga ttttggtcat gagattatca aaaaggatct tcacctagat ccttttaaat    3900
taaaaatgaa gttttaaatc aatctaaagt atatatgagt aaacttggtc tgacagttac    3960
```

-continued

```
caatgcttaa tcagtgaggc acctatctca gcgatctgtc tatttcgttc atccatagtt    4020
gcctgactcc ccgtcgtgta gataactacg atacgggagg gcttaccatc tggcccagt    4080 gctgcaatga taccgcgaga cccacgctca ccggctccag atttatcagc aataaaccag    4140
ccagccggaa gggccgagcg cagaagtggt cctgcaactt tatccgcctc catccagtct    4200
attaattgtt gccgggaagc tagagtaagt agttcgccag ttaatagttt gcgcaacgtt    4260
gttgccattg ctacaggcat cgtggtgtca cgctcgtcgt ttggtatggc ttcattcagc    4320
tccggttccc aacgatcaag gcagttaca tgatccccca tgttgtgcaa aaaagcggtt    4380
agctccttcg gtcctccgat cgttgtcaga agtaagttgg ccgcagtgtt atcactcatg    4440
gttatggcag cactgcataa ttctcttact gtcatgccat ccgtaagatg cttttctgtg    4500
actggtgagt actcaaccaa gtcattctga gaatagtgta tgcggcgacc gagttgctct    4560
tgcccggcgt caatacggga taataccgcg ccacatagca gaactttaaa agtgctcatc    4620
attgaaaaac gttcttcggg gcgaaaactc tcaaggatct taccgctgtt gagatccagt    4680
tcgatgtaac ccactcgtgc acccaactga tcttcagcat cttttacttt caccagcgtt    4740
tctgggtgag caaaaacagg aaggcaaaat gccgcaaaaa agggaataag ggcgacacgg    4800
aaatgttgaa tactcatact cttcctttt caatattatt gaagcattta tcagggttat    4860
tgtctcatga gcggatacat atttgaatgt atttagaaaa ataaacaaat aggggttccg    4920
cgcacatttc cccgaaaagt gccacctgac gtctaagaaa ccattattat catgacatta    4980
acctataaaa ataggcgtat cacgaggccc tttcgtc                              5017
```

```
<210> SEQ ID NO 9
<211> LENGTH: 775
<212> TYPE: PRT
<213> ORGANISM: Pyrococcus furiosus

<400> SEQUENCE: 9

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190
```

```
Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
        210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
```

```
                610                 615                 620
Ala Arg Val Leu Glu Thr Ile Leu Lys His Gly Asp Val Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
                675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
                740                 745                 750

Lys Glu Asp Leu Arg Tyr Gln Lys Thr Arg Gln Val Gly Leu Thr Ser
                755                 760                 765

Trp Leu Asn Ile Lys Lys Ser
770                 775

<210> SEQ ID NO 10
<211> LENGTH: 778
<212> TYPE: PRT
<213> ORGANISM: Artificial Sequence
<220> FEATURE:
<223> OTHER INFORMATION: Pfu amino acid sequence, extra 3 aa in 5' area.

<400> SEQUENCE: 10

Met Ala Ser Ala Ile Leu Asp Val Asp Tyr Ile Thr Glu Glu Gly Lys
1               5                   10                  15

Pro Val Ile Arg Leu Phe Lys Lys Glu Asn Gly Lys Phe Lys Ile Glu
                20                  25                  30

His Asp Arg Thr Phe Arg Pro Tyr Ile Tyr Ala Leu Leu Arg Asp Asp
                35                  40                  45

Ser Lys Ile Glu Glu Val Lys Lys Ile Thr Gly Glu Arg His Gly Lys
50                  55                  60

Ile Val Arg Ile Val Asp Val Glu Lys Val Glu Lys Lys Phe Leu Gly
65                  70                  75                  80

Lys Pro Ile Thr Val Trp Lys Leu Tyr Leu Glu His Pro Gln Asp Val
                85                  90                  95

Pro Thr Ile Arg Glu Lys Val Arg Glu His Pro Ala Val Val Asp Ile
                100                 105                 110

Phe Glu Tyr Asp Ile Pro Phe Ala Lys Arg Tyr Leu Ile Asp Lys Gly
                115                 120                 125

Leu Ile Pro Met Glu Gly Glu Glu Leu Lys Ile Leu Ala Phe Asp
130                 135                 140

Ile Glu Thr Leu Tyr His Glu Gly Glu Glu Phe Gly Lys Gly Pro Ile
145                 150                 155                 160

Ile Met Ile Ser Tyr Ala Asp Glu Asn Glu Ala Lys Val Ile Thr Trp
                165                 170                 175

Lys Asn Ile Asp Leu Pro Tyr Val Glu Val Val Ser Ser Glu Arg Glu
                180                 185                 190

Met Ile Lys Arg Phe Leu Arg Ile Ile Arg Glu Lys Asp Pro Asp Ile
                195                 200                 205
```

Ile Val Thr Tyr Asn Gly Asp Ser Phe Asp Phe Pro Tyr Leu Ala Lys
210                 215                 220

Arg Ala Glu Lys Leu Gly Ile Lys Leu Thr Ile Gly Arg Asp Gly Ser
225                 230                 235                 240

Glu Pro Lys Met Gln Arg Ile Gly Asp Met Thr Ala Val Glu Val Lys
                245                 250                 255

Gly Arg Ile His Phe Asp Leu Tyr His Val Ile Thr Arg Thr Ile Asn
                260                 265                 270

Leu Pro Thr Tyr Thr Leu Glu Ala Val Tyr Glu Ala Ile Phe Gly Lys
            275                 280                 285

Pro Lys Glu Lys Val Tyr Ala Asp Glu Ile Ala Lys Ala Trp Glu Ser
290                 295                 300

Gly Glu Asn Leu Glu Arg Val Ala Lys Tyr Ser Met Glu Asp Ala Lys
305                 310                 315                 320

Ala Thr Tyr Glu Leu Gly Lys Glu Phe Leu Pro Met Glu Ile Gln Leu
                325                 330                 335

Ser Arg Leu Val Gly Gln Pro Leu Trp Asp Val Ser Arg Ser Ser Thr
                340                 345                 350

Gly Asn Leu Val Glu Trp Phe Leu Arg Lys Ala Tyr Glu Arg Asn
            355                 360                 365

Glu Val Ala Pro Asn Lys Pro Ser Glu Glu Tyr Gln Arg Arg Leu
370                 375                 380

Arg Glu Ser Tyr Thr Gly Gly Phe Val Lys Glu Pro Glu Lys Gly Leu
385                 390                 395                 400

Trp Glu Asn Ile Val Tyr Leu Asp Phe Arg Ala Leu Tyr Pro Ser Ile
                405                 410                 415

Ile Ile Thr His Asn Val Ser Pro Asp Thr Leu Asn Leu Glu Gly Cys
                420                 425                 430

Lys Asn Tyr Asp Ile Ala Pro Gln Val Gly His Lys Phe Cys Lys Asp
                435                 440                 445

Ile Pro Gly Phe Ile Pro Ser Leu Leu Gly His Leu Leu Glu Glu Arg
            450                 455                 460

Gln Lys Ile Lys Thr Lys Met Lys Glu Thr Gln Asp Pro Ile Glu Lys
465                 470                 475                 480

Ile Leu Leu Asp Tyr Arg Gln Lys Ala Ile Lys Leu Leu Ala Asn Ser
                485                 490                 495

Phe Tyr Gly Tyr Tyr Gly Tyr Ala Lys Ala Arg Trp Tyr Cys Lys Glu
            500                 505                 510

Cys Ala Glu Ser Val Thr Ala Trp Gly Arg Lys Tyr Ile Glu Leu Val
            515                 520                 525

Trp Lys Glu Leu Glu Glu Lys Phe Gly Phe Lys Val Leu Tyr Ile Asp
            530                 535                 540

Thr Asp Gly Leu Tyr Ala Thr Ile Pro Gly Gly Glu Ser Glu Glu Ile
545                 550                 555                 560

Lys Lys Lys Ala Leu Glu Phe Val Lys Tyr Ile Asn Ser Lys Leu Pro
                565                 570                 575

Gly Leu Leu Glu Leu Glu Tyr Glu Gly Phe Tyr Lys Arg Gly Phe Phe
                580                 585                 590

Val Thr Lys Lys Arg Tyr Ala Val Ile Asp Glu Glu Gly Lys Val Ile
            595                 600                 605

Thr Arg Gly Leu Glu Ile Val Arg Arg Asp Trp Ser Glu Ile Ala Lys
610                 615                 620

Glu Thr Gln Ala Arg Val Leu Glu Thr Ile Leu Lys His Gly Asp Val

```
            625                 630                 635                 640
Glu Glu Ala Val Arg Ile Val Lys Glu Val Ile Gln Lys Leu Ala Asn
                    645                 650                 655
Tyr Glu Ile Pro Pro Glu Lys Leu Ala Ile Tyr Glu Gln Ile Thr Arg
                660                 665                 670
Pro Leu His Glu Tyr Lys Ala Ile Gly Pro His Val Ala Val Ala Lys
            675                 680                 685
Lys Leu Ala Ala Lys Gly Val Lys Ile Lys Pro Gly Met Val Ile Gly
        690                 695                 700
Tyr Ile Val Leu Arg Gly Asp Gly Pro Ile Ser Asn Arg Ala Ile Leu
705                 710                 715                 720
Ala Glu Glu Tyr Asp Pro Lys Lys His Lys Tyr Asp Ala Glu Tyr Tyr
                    725                 730                 735
Ile Glu Asn Gln Val Leu Pro Ala Val Leu Arg Ile Leu Glu Gly Phe
                740                 745                 750
Gly Tyr Arg Lys Glu Asp Leu Arg Tyr Gln Lys Thr Arg Gln Val Gly
            755                 760                 765
Leu Thr Ser Trp Leu Asn Ile Lys Lys Ser
        770                 775

<210> SEQ ID NO 11
<211> LENGTH: 774
<212> TYPE: PRT
<213> ORGANISM: Thermococcus sp.

<400> SEQUENCE: 11

Met Ile Leu Asp Thr Asp Tyr Ile Thr Glu Asp Gly Lys Pro Val Ile
1               5                   10                  15
Arg Ile Phe Lys Lys Glu Asn Gly Glu Phe Lys Ile Glu Tyr Asp Arg
            20                  25                  30
Thr Phe Glu Pro Tyr Phe Tyr Ala Leu Leu Lys Asp Asp Ser Ala Ile
        35                  40                  45
Glu Glu Val Lys Lys Ile Thr Ala Glu Arg His Gly Thr Val Val Thr
    50                  55                  60
Val Lys Arg Val Glu Lys Val Gln Lys Lys Phe Leu Gly Arg Pro Val
65                  70                  75                  80
Glu Val Trp Lys Leu Tyr Phe Thr His Pro Gln Asp Val Pro Ala Ile
                85                  90                  95
Arg Asp Lys Ile Arg Glu His Pro Ala Val Ile Asp Ile Tyr Glu Tyr
            100                 105                 110
Asp Ile Pro Phe Ala Lys Arg Tyr Leu Ile Asp Lys Gly Leu Val Pro
        115                 120                 125
Met Glu Gly Asp Glu Glu Leu Lys Met Leu Ala Phe Asp Ile Glu Thr
    130                 135                 140
Leu Tyr His Glu Gly Glu Glu Phe Ala Glu Gly Pro Ile Leu Met Ile
145                 150                 155                 160
Ser Tyr Ala Asp Glu Glu Gly Ala Arg Val Ile Thr Trp Lys Asn Val
                165                 170                 175
Asp Leu Pro Tyr Val Asp Val Val Ser Thr Glu Arg Glu Met Ile Lys
            180                 185                 190
Arg Phe Leu Arg Val Val Lys Glu Lys Asp Pro Asp Val Leu Ile Thr
        195                 200                 205
Tyr Asn Gly Asp Asn Phe Asp Phe Ala Tyr Leu Lys Lys Arg Cys Glu
    210                 215                 220
Lys Leu Gly Ile Asn Phe Ala Leu Gly Arg Asp Gly Ser Glu Pro Lys
```

```
              225                 230                 235                 240
Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Gln Pro Lys Glu
                275                 280                 285

Lys Val Tyr Ala Glu Glu Ile Thr Thr Ala Trp Glu Thr Gly Glu Asn
                290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Lys Glu Leu Ala Arg Arg Gln Ser Tyr
                370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
                420                 425                 430

Val Ala Pro Gln Val Gly His Arg Phe Cys Lys Asp Phe Pro Gly Phe
                435                 440                 445

Ile Pro Ser Leu Leu Gly Asp Leu Leu Glu Glu Arg Gln Lys Ile Lys
                450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
                500                 505                 510

Val Thr Ala Trp Gly Arg Glu Tyr Ile Thr Met Thr Ile Lys Glu Ile
                515                 520                 525

Glu Glu Lys Tyr Gly Phe Lys Val Ile Tyr Ser Asp Thr Asp Gly Phe
                530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
                580                 585                 590

Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
                610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655
```

```
Pro Glu Lys Leu Val Ile His Glu Gln Ile Thr Arg Asp Leu Lys Asp
            660                 665                 670

Tyr Lys Ala Thr Gly Pro His Val Ala Val Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
            755                 760                 765

Leu Lys Pro Lys Gly Thr
    770

<210> SEQ ID NO 12
<211> LENGTH: 777
<212> TYPE: PRT
<213> ORGANISM: Artificial Sequence
<220> FEATURE:
<223> OTHER INFORMATION: KOD amino acid sequence, extra 3 aa in 5' area.

<400> SEQUENCE: 12

Met Ala Ser Ala Ile Leu Asp Thr Asp Tyr Ile Thr Glu Asp Gly Lys
1               5                   10                  15

Pro Val Ile Arg Ile Phe Lys Lys Glu Asn Gly Glu Phe Lys Ile Glu
            20                  25                  30

Tyr Asp Arg Thr Phe Glu Pro Tyr Phe Tyr Ala Leu Leu Lys Asp Asp
        35                  40                  45

Ser Ala Ile Glu Glu Val Lys Lys Ile Thr Ala Glu Arg His Gly Thr
    50                  55                  60

Val Val Thr Val Lys Arg Val Glu Lys Val Gln Lys Lys Phe Leu Gly
65                  70                  75                  80

Arg Pro Val Glu Val Trp Lys Leu Tyr Phe Thr His Pro Gln Asp Val
                85                  90                  95

Pro Ala Ile Arg Asp Lys Ile Arg Glu His Pro Ala Val Ile Asp Ile
            100                 105                 110

Tyr Glu Tyr Asp Ile Pro Phe Ala Lys Arg Tyr Leu Ile Asp Lys Gly
        115                 120                 125

Leu Val Pro Met Glu Gly Asp Glu Glu Leu Lys Met Leu Ala Phe Asp
    130                 135                 140

Ile Glu Thr Leu Tyr His Glu Gly Glu Glu Phe Ala Glu Gly Pro Ile
145                 150                 155                 160

Leu Met Ile Ser Tyr Ala Asp Glu Glu Gly Ala Arg Val Ile Thr Trp
                165                 170                 175

Lys Asn Val Asp Leu Pro Tyr Val Asp Val Val Ser Thr Glu Arg Glu
            180                 185                 190

Met Ile Lys Arg Phe Leu Arg Val Val Lys Glu Lys Asp Pro Asp Val
        195                 200                 205

Leu Ile Thr Tyr Asn Gly Asp Asn Phe Asp Phe Ala Tyr Leu Lys Lys
    210                 215                 220

Arg Cys Glu Lys Leu Gly Ile Asn Phe Ala Leu Gly Arg Asp Gly Ser
225                 230                 235                 240

Glu Pro Lys Ile Gln Arg Met Gly Asp Arg Phe Ala Val Glu Val Lys
```

```
                245                 250                 255
Gly Arg Ile His Phe Asp Leu Tyr Pro Val Ile Arg Arg Thr Ile Asn
            260                 265                 270

Leu Pro Thr Tyr Thr Leu Glu Ala Val Tyr Glu Ala Val Phe Gly Gln
            275                 280                 285

Pro Lys Glu Lys Val Tyr Ala Glu Glu Ile Thr Thr Ala Trp Glu Thr
            290                 295                 300

Gly Glu Asn Leu Glu Arg Val Ala Arg Tyr Ser Met Glu Asp Ala Lys
305                 310                 315                 320

Val Thr Tyr Glu Leu Gly Lys Glu Phe Leu Pro Met Glu Ala Gln Leu
            325                 330                 335

Ser Arg Leu Ile Gly Gln Ser Leu Trp Asp Val Ser Arg Ser Ser Thr
            340                 345                 350

Gly Asn Leu Val Glu Trp Phe Leu Leu Arg Lys Ala Tyr Glu Arg Asn
            355                 360                 365

Glu Leu Ala Pro Asn Lys Pro Asp Glu Lys Glu Leu Ala Arg Arg Arg
            370                 375                 380

Gln Ser Tyr Glu Gly Gly Tyr Val Lys Glu Pro Glu Arg Gly Leu Trp
385                 390                 395                 400

Glu Asn Ile Val Tyr Leu Asp Phe Arg Ser Leu Tyr Pro Ser Ile Ile
            405                 410                 415

Ile Thr His Asn Val Ser Pro Asp Thr Leu Asn Arg Glu Gly Cys Lys
            420                 425                 430

Glu Tyr Asp Val Ala Pro Gln Val Gly His Arg Phe Cys Lys Asp Phe
            435                 440                 445

Pro Gly Phe Ile Pro Ser Leu Leu Gly Asp Leu Leu Glu Glu Arg Gln
            450                 455                 460

Lys Ile Lys Lys Lys Met Lys Ala Thr Ile Asp Pro Ile Glu Arg Lys
465                 470                 475                 480

Leu Leu Asp Tyr Arg Gln Arg Ala Ile Lys Ile Leu Ala Asn Ser Tyr
            485                 490                 495

Tyr Gly Tyr Tyr Gly Tyr Ala Arg Ala Arg Trp Tyr Cys Lys Glu Cys
            500                 505                 510

Ala Glu Ser Val Thr Ala Trp Gly Arg Glu Tyr Ile Thr Met Thr Ile
            515                 520                 525

Lys Glu Ile Glu Glu Lys Tyr Gly Phe Lys Val Ile Tyr Ser Asp Thr
            530                 535                 540

Asp Gly Phe Phe Ala Thr Ile Pro Gly Ala Asp Ala Glu Thr Val Lys
545                 550                 555                 560

Lys Lys Ala Met Glu Phe Leu Lys Tyr Ile Asn Ala Lys Leu Pro Gly
            565                 570                 575

Ala Leu Glu Leu Glu Tyr Glu Gly Phe Tyr Lys Arg Gly Phe Phe Val
            580                 585                 590

Thr Lys Lys Lys Tyr Ala Val Ile Asp Glu Glu Gly Lys Ile Thr Thr
            595                 600                 605

Arg Gly Leu Glu Ile Val Arg Arg Asp Trp Ser Glu Ile Ala Lys Glu
            610                 615                 620

Thr Gln Ala Arg Val Leu Glu Ala Leu Leu Lys Asp Gly Asp Val Glu
625                 630                 635                 640

Lys Ala Val Arg Ile Val Lys Glu Val Thr Glu Lys Leu Ser Lys Tyr
            645                 650                 655

Glu Val Pro Pro Glu Lys Leu Val Ile His Glu Gln Ile Thr Arg Asp
            660                 665                 670
```

```
Leu Lys Asp Tyr Lys Ala Thr Gly Pro His Val Ala Val Ala Lys Arg
        675                 680                 685

Leu Ala Ala Arg Gly Val Lys Ile Arg Pro Gly Thr Val Ile Ser Tyr
    690                 695                 700

Ile Val Leu Lys Gly Ser Gly Arg Ile Gly Asp Arg Ala Ile Pro Phe
705                 710                 715                 720

Asp Glu Phe Asp Pro Thr Lys His Lys Tyr Asp Ala Glu Tyr Tyr Ile
                725                 730                 735

Glu Asn Gln Val Leu Pro Ala Val Glu Arg Ile Leu Arg Ala Phe Gly
            740                 745                 750

Tyr Arg Lys Glu Asp Leu Arg Tyr Gln Lys Thr Arg Gln Val Gly Leu
        755                 760                 765

Ser Ala Trp Leu Lys Pro Lys Gly Thr
    770                 775

<210> SEQ ID NO 13
<211> LENGTH: 2334
<212> TYPE: DNA
<213> ORGANISM: Artificial Sequence
<220> FEATURE:
<223> OTHER INFORMATION: Pod codon optimized nucleotide sequence

<400> SEQUENCE: 13
atggctagcg ccattctgga tgtggactat atcaccgaag agggcaaacc ggttatacgt      60
ttatttaaga agagaatgg taaattcaag atcgagcatg accgcacgtt ccgtccatac     120
atttacgcgt tgcttcggga tgatagcaaa attgaggaag tcaaaaagat caccggggaa     180
cgtcatggaa aaatagtaag aattgtggac gttgaaaaag tcgaaaagaa atttctgggc     240
aaaccgatca ctgtatggaa gctctatctg aacatcctc aggatgtgcc cacaattcga     300
gaaaaagttc gtgagcaccc agccgtcgtg atatatttg aatatgacat ccctttttgca    360 aaacgctact taattgataa aggcctgatc ccgatggagg gggaagaaga acttaaaatt     420
ctggcttttg acatagaaac gctctatcat gagggagaag aatttggcaa aggtcccatc     480
attatgattt cttacgcgga tgagaacgaa gccaaggtaa tcacttggaa aaatattgac     540
ctgccgtacg ttgaagtggt cagttcagag cgggaaatga ttaaacgttt tttacgcatc     600
attagagaga aagatccaga tataatcgtt acatataacg gcgactcctt cgattttcct     660
tacctggcaa acgagctga aaaattgggt attaaactta ccatcgggcg tgacggatcg     720
gaaccgaaaa tgcaacgcat tggcgatatg acggcggtag aggtgaaagg tcggatacac     780
tttgatctgt atcatgtcat caccgtact attaatctcc ccacatacac gttagaagcc      840
gtttatgagg caatattcgg caagccgaaa gaaaaagtgt acgctgacga atcgcgaag     900 gcatgggaga gcggcgaaaa cctggagcgc gtagcaaaat attctatgga agatgctaaa     960
gcgacctacg aattgggaa agaatttctt ccaatggaaa ttcagctgtc gagattaata    1020
gggcagagcc tgtgggacgt gtctcgaagt tcaacggaa acctcgtcga atggtttctg    1080
ttgcggaaag catacgagcg taatgaactt gcccctaaca aaccggatga aaaggagctg    1140
gcacgccgtc gccaatccta tgaaggcggt tacgttaaag aaccagagcg ggggttatgg    1200
gaaaatatcg tgtatctgga tttccgttcg ctctacccga gcattatcat taccacaac    1260 gtatctcccg acactttgaa tcgcgagggc tgtaaagaat atgatgtcgc gccgcaggtt    1320
ggtcatagat tttgcaagga cttcccggga tttataccaa gtctgcttgg cgatttactg    1380
gaagagcgac aaaaaatcaa aagaaaatg aaagctacaa tcgatccgat agaacgtaag    1440
ctgctcgact accgccagcg ggccatcaaa attttggcaa actcatatta tggttactat    1500
```

| | |
|---|---|
| gggtacgcgc gtgctcgctg gtattgtaaa gagtgcgccg aatccgtgac ggcatggggc | 1560 |
| cgtgaataca tcaccatgac tattaaggag atagaagaga aatatggttt caaagtaatc | 1620 |
| tactcggata cagacggatt ctttgcgacg attcccggtg ccgatgcaga aaccgtcaag | 1680 |
| aaaaaagcga tggaattcgt taagtacatt aatagtaaat taccgggact gcttgaactg | 1740 |
| gagtatgaag gcttctacaa aagaggtttt ttcgttacta agaaacgata tgccgtaata | 1800 |
| gatgaagagg ggaaagtcat cacacgtggc ctcgagattg ttcgccggga ctggtcagag | 1860 |
| atagcaaagg aaacgcaggc gcgcgtgctc gaaaccatct tgaaacatgg tgatgtagag | 1920 |
| gaagccgtcc gcattgttaa agaggtgatc cagaagttag caaactatga aattccaccg | 1980 |
| gaaaaactgg cgatatacga gcaaatcact cgtcccctcc acgaatataa agctattgga | 2040 |
| cctcatgtag ccgtcgcgaa gaaactggct gcaaaaggcg ttaagataaa accaggtatg | 2100 |
| gtgatcgggt acattgtact ccgcggcgac ggtccgattt ccaatagagc catcttggcg | 2160 |
| gaggaatatg atcctaaaaa gcataaatac gacgctgaat attacattga gaaccaggtc | 2220 |
| ttgccggcag ttctgcggat acttgaagga tttggctatc gtaaagaaga tctgcgctat | 2280 |
| caaaagacgc gacaggtggg tctgactagc tggttgaata tcaaaaaatc gtaa | 2334 |

<210> SEQ ID NO 14
<211> LENGTH: 2337
<212> TYPE: DNA
<213> ORGANISM: Artificial Sequence
<220> FEATURE:
<223> OTHER INFORMATION: Kofu codon optimized nucleotide sequence

<400> SEQUENCE: 14

| | |
|---|---|
| atggctagcg ccattctgga taccgactat atcacggaag atggcaaacc ggtgatacgt | 60 |
| atttttaaga aagagaatgg tgagttcaaa atcgagtacg accgcacttt tgagccatat | 120 |
| ttctacgcgt tactgaagga cgatagcgcc attgaagaag ttaaaaaaat caccgcagag | 180 |
| cggcatggga cagtggtaac cgtgaagaga gttgaaaaag tccagaaaaa attttttggga | 240 |
| cgacctgtag aagtgtggaa actttatttc actcaccccc aagatgttcc ggctatacgt | 300 |
| gataaaattc gcgaacatcc agcggtcatt gatatttacg aatatgatat acctttttgcc | 360 |
| aagcgttacc tcatcgacaa aggcctggtg ccgatggaag gtgatgaaga attaaaaatg | 420 |
| ttggcattcg acattgaaac actttatcac gaggggaag agtttgctga gggtcccatc | 480 |
| ctgatgattt cttatgcgga tgaagagggt gcccgcgtaa taactgaa gaacgttgat | 540 |
| ctcccgtacg tggacgtcgt tagtacggaa cgggaaatga tcaaacgttt cctgcgcgta | 600 |
| gtgaaagaga aagatccaga cgtcttaatt acctataatg gtgataactt tgatttttgca | 660 |
| tacctgaaaa aagatgcga aaagttgggc ataaatttcg ctcttggtcg agacgggtca | 720 |
| gagcctaaaa tccagcgtat gggagatcgc tttgcggttg aagtgaaagg ccggattcat | 780 |
| ttcgacctgt atccggtaat tcgtcgcact atcaacctcc ccacatacac gttagaagcc | 840 |
| gtctatgagg cagttttttgg tcaaccgaag gaaaaagttt acgctgagga aattaccact | 900 |
| gcgtgggaaa caggcgagaa tctggaacgt gtagcccgct attctatgga ggatgcaaaa | 960 |
| gttacctatg aattgggtaa ggaatttctt ccaatggagg cgcagctgag tcgtttagtc | 1020 |
| ggacaacctc tgtgggacgt tcacgctcc tcgactggca tctcgtgga gtggttcctg | 1080 |
| ttgagaaaag cctatgaacg aaacgaagta gcaccgaata aaccaagcga ggaagaatat | 1140 |
| cagcgtcgcc ttcgcgagtc ttacacaggt gggtttgtta aggaaccgga gaaaggtctt | 1200 |
| tgggaaaaca tcgtgtattt agatttccgt gcgctgtacc ccagtattat aatcacccac | 1260 |

```
aatgtctcac ctgacacgct caacttggaa ggttgcaaaa attatgatat tgctccgcaa    1320
gttggacata agttttgtaa agatattccg ggcttcatcc cgtccctgct tggtcactta    1380
ctggaagagc gccaaaaaat taagaccaaa atgaaagaga ctcaggatcc cattgaaaag    1440
atcctgctcg attaccggca aaaagccatt aaattgcttg caaactcgtt ttatgggtac    1500
tatggctatg cgaaggctcg ttggtactgc aaagaatgtg ccgagagcgt gacagcatgg    1560
ggtcgcaaat atatagaatt agtatggaag gagctggaag aaaaattcgg attcaaagtc    1620
ctgtacatcg atacggatgg cctctatgcg accattcctg gtggggagtc tgaagaaatc    1680
aagaaaaaag ccttggaatt ccttaagtat ataaatgcta aattacctgg tgccctggag    1740
ctggaatacg aagggtttta caaacgcgga ttctttgtta ctaagaaaaa atatgcggtg    1800
atcgacgagg aaggcaagat tacgaccaga ggcctcgaga ttgtacggcg tgattggagc    1860
gaaatcgcta agaaacaca ggcacgtgtc ttggaggcat tactgaaaga tggggacgtt    1920
gaaaaggcgg tgcgaattgt aaaagaagtc accgaaaaac tttctaagta cgaagttccg    1980
ccagagaaac tggtgataca cgaacaaatc actcgtgatc tgaaagacta taaggctaca    2040
ggcccgcatg tagcagtcgc caaacgcctc gcggctcggg gtgttaaaat tcgtcccgga    2100
acggtgatca gttacattgt attgaagggc tcaggtcgca taggggatag agcaatccct    2160
ttcgacgagt ttgatccaac caaacacaaa tatgatgccg aatactatat tgaaaaccag    2220
gtcttgccgg cggttgagcg tatactgcgc gctttcggct atcgaaagga agatcttcgt    2280
taccaaaaaa ctagacaggt gggtctgtcc gcatggctca aacctaaggg aacgtaa      2337
```

<210> SEQ ID NO 15
<211> LENGTH: 777
<212> TYPE: PRT
<213> ORGANISM: Artificial Sequence
<220> FEATURE:
<223> OTHER INFORMATION: Pod amino acid sequence

<400> SEQUENCE: 15

```
Met Ala Ser Ala Ile Leu Asp Val Asp Tyr Ile Thr Glu Glu Gly Lys
1               5                   10                  15

Pro Val Ile Arg Leu Phe Lys Lys Glu Asn Gly Lys Phe Lys Ile Glu
            20                  25                  30

His Asp Arg Thr Phe Arg Pro Tyr Ile Tyr Ala Leu Leu Arg Asp Asp
        35                  40                  45

Ser Lys Ile Glu Glu Val Lys Lys Ile Thr Gly Glu Arg His Gly Lys
    50                  55                  60

Ile Val Arg Ile Val Asp Val Glu Lys Val Glu Lys Lys Phe Leu Gly
65                  70                  75                  80

Lys Pro Ile Thr Val Trp Lys Leu Tyr Leu Glu His Pro Gln Asp Val
                85                  90                  95

Pro Thr Ile Arg Glu Lys Val Arg Glu His Pro Ala Val Val Asp Ile
            100                 105                 110

Phe Glu Tyr Asp Ile Pro Phe Ala Lys Arg Tyr Leu Ile Asp Lys Gly
        115                 120                 125

Leu Ile Pro Met Glu Gly Glu Glu Leu Lys Ile Leu Ala Phe Asp
    130                 135                 140

Ile Glu Thr Leu Tyr His Glu Gly Glu Glu Phe Gly Lys Gly Pro Ile
145                 150                 155                 160

Ile Met Ile Ser Tyr Ala Asp Glu Asn Glu Ala Lys Val Ile Thr Trp
                165                 170                 175
```

-continued

```
Lys Asn Ile Asp Leu Pro Tyr Val Glu Val Ser Ser Glu Arg Glu
            180                 185                 190

Met Ile Lys Arg Phe Leu Arg Ile Arg Glu Lys Asp Pro Asp Ile
        195                 200                 205

Ile Val Thr Tyr Asn Gly Asp Ser Phe Asp Phe Pro Tyr Leu Ala Lys
210                 215                 220

Arg Ala Glu Lys Leu Gly Ile Lys Leu Thr Ile Gly Arg Asp Gly Ser
225                 230                 235                 240

Glu Pro Lys Met Gln Arg Ile Gly Asp Met Thr Ala Val Glu Val Lys
                245                 250                 255

Gly Arg Ile His Phe Asp Leu Tyr His Val Ile Thr Arg Thr Ile Asn
                260                 265                 270

Leu Pro Thr Tyr Thr Leu Glu Ala Val Tyr Glu Ala Ile Phe Gly Lys
            275                 280                 285

Pro Lys Glu Lys Val Tyr Ala Asp Glu Ile Ala Lys Ala Trp Glu Ser
290                 295                 300

Gly Glu Asn Leu Glu Arg Val Ala Lys Tyr Ser Met Glu Asp Ala Lys
305                 310                 315                 320

Ala Thr Tyr Glu Leu Gly Lys Glu Phe Leu Pro Met Glu Ile Gln Leu
                325                 330                 335

Ser Arg Leu Ile Gly Gln Ser Leu Trp Asp Val Ser Arg Ser Ser Thr
            340                 345                 350

Gly Asn Leu Val Glu Trp Phe Leu Leu Arg Lys Ala Tyr Glu Arg Asn
            355                 360                 365

Glu Leu Ala Pro Asn Lys Pro Asp Glu Lys Leu Ala Arg Arg Arg
370                 375                 380

Gln Ser Tyr Glu Gly Gly Tyr Val Lys Glu Pro Glu Arg Gly Leu Trp
385                 390                 395                 400

Glu Asn Ile Val Tyr Leu Asp Phe Arg Ser Leu Tyr Pro Ser Ile Ile
                405                 410                 415

Ile Thr His Asn Val Ser Pro Asp Thr Leu Asn Arg Glu Gly Cys Lys
                420                 425                 430

Glu Tyr Asp Val Ala Pro Gln Val Gly His Arg Phe Cys Lys Asp Phe
            435                 440                 445

Pro Gly Phe Ile Pro Ser Leu Leu Gly Asp Leu Leu Glu Glu Arg Gln
450                 455                 460

Lys Ile Lys Lys Met Lys Ala Thr Ile Asp Pro Ile Glu Arg Lys
465                 470                 475                 480

Leu Leu Asp Tyr Arg Gln Arg Ala Ile Lys Ile Leu Ala Asn Ser Tyr
                485                 490                 495

Tyr Gly Tyr Tyr Gly Tyr Ala Arg Ala Arg Trp Tyr Cys Lys Glu Cys
            500                 505                 510

Ala Glu Ser Val Thr Ala Trp Gly Arg Glu Tyr Ile Thr Met Thr Ile
515                 520                 525

Lys Glu Ile Glu Glu Lys Tyr Gly Phe Lys Val Ile Tyr Ser Asp Thr
        530                 535                 540

Asp Gly Phe Phe Ala Thr Ile Pro Gly Ala Asp Ala Glu Thr Val Lys
545                 550                 555                 560

Lys Lys Ala Met Glu Phe Val Lys Tyr Ile Asn Ser Lys Leu Pro Gly
                565                 570                 575

Leu Leu Glu Leu Glu Tyr Glu Gly Phe Tyr Lys Arg Gly Phe Phe Val
            580                 585                 590

Thr Lys Lys Arg Tyr Ala Val Ile Asp Glu Glu Gly Lys Val Ile Thr
            595                 600                 605
```

```
Arg Gly Leu Glu Ile Val Arg Arg Asp Trp Ser Glu Ile Ala Lys Glu
        610                 615                 620

Thr Gln Ala Arg Val Leu Glu Thr Ile Leu Lys His Gly Asp Val Glu
625                 630                 635                 640

Glu Ala Val Arg Ile Val Lys Glu Val Ile Gln Lys Leu Ala Asn Tyr
                645                 650                 655

Glu Ile Pro Pro Glu Lys Leu Ala Ile Tyr Glu Gln Ile Thr Arg Pro
                660                 665                 670

Leu His Glu Tyr Lys Ala Ile Gly Pro His Val Ala Val Ala Lys Lys
            675                 680                 685

Leu Ala Ala Lys Gly Val Lys Ile Lys Pro Gly Met Val Ile Gly Tyr
        690                 695                 700

Ile Val Leu Arg Gly Asp Gly Pro Ile Ser Asn Arg Ala Ile Leu Ala
705                 710                 715                 720

Glu Glu Tyr Asp Pro Lys Lys His Lys Tyr Asp Ala Glu Tyr Tyr Ile
                725                 730                 735

Glu Asn Gln Val Leu Pro Ala Val Leu Arg Ile Leu Glu Gly Phe Gly
                740                 745                 750

Tyr Arg Lys Glu Asp Leu Arg Tyr Gln Lys Thr Arg Gln Val Gly Leu
            755                 760                 765

Thr Ser Trp Leu Asn Ile Lys Lys Ser
        770                 775

<210> SEQ ID NO 16
<211> LENGTH: 778
<212> TYPE: PRT
<213> ORGANISM: Artificial Sequence
<220> FEATURE:
<223> OTHER INFORMATION: Kofu amino acid sequence

<400> SEQUENCE: 16

Met Ala Ser Ala Ile Leu Asp Thr Asp Tyr Ile Thr Glu Asp Gly Lys
1               5                   10                  15

Pro Val Ile Arg Ile Phe Lys Lys Glu Asn Gly Glu Phe Lys Ile Glu
                20                  25                  30

Tyr Asp Arg Thr Phe Glu Pro Tyr Phe Tyr Ala Leu Leu Lys Asp Asp
            35                  40                  45

Ser Ala Ile Glu Glu Val Lys Lys Ile Thr Ala Glu Arg His Gly Thr
        50                  55                  60

Val Val Thr Val Lys Arg Val Glu Lys Val Gln Lys Lys Phe Leu Gly
65                  70                  75                  80

Arg Pro Val Glu Val Trp Lys Leu Tyr Phe Thr His Pro Gln Asp Val
                85                  90                  95

Pro Ala Ile Arg Asp Lys Ile Arg Glu His Pro Ala Val Ile Asp Ile
                100                 105                 110

Tyr Glu Tyr Asp Ile Pro Phe Ala Lys Arg Tyr Leu Ile Asp Lys Gly
            115                 120                 125

Leu Val Pro Met Glu Gly Asp Glu Glu Leu Lys Met Leu Ala Phe Asp
        130                 135                 140

Ile Glu Thr Leu Tyr His Glu Gly Glu Glu Phe Ala Glu Gly Pro Ile
145                 150                 155                 160

Leu Met Ile Ser Tyr Ala Asp Glu Glu Gly Ala Arg Val Ile Thr Trp
                165                 170                 175

Lys Asn Val Asp Leu Pro Tyr Val Asp Val Val Ser Thr Glu Arg Glu
                180                 185                 190
```

-continued

```
Met Ile Lys Arg Phe Leu Arg Val Lys Glu Lys Asp Pro Asp Val
    195                 200                 205

Leu Ile Thr Tyr Asn Gly Asp Asn Phe Asp Phe Ala Tyr Leu Lys Lys
    210                 215                 220

Arg Cys Glu Lys Leu Gly Ile Asn Phe Ala Leu Gly Arg Asp Gly Ser
225                 230                 235                 240

Glu Pro Lys Ile Gln Arg Met Gly Asp Arg Phe Ala Val Glu Val Lys
                245                 250                 255

Gly Arg Ile His Phe Asp Leu Tyr Pro Val Ile Arg Arg Thr Ile Asn
                    260                 265                 270

Leu Pro Thr Tyr Thr Leu Glu Ala Val Tyr Glu Ala Val Phe Gly Gln
                275                 280                 285

Pro Lys Glu Lys Val Tyr Ala Glu Glu Ile Thr Thr Ala Trp Glu Thr
            290                 295                 300

Gly Glu Asn Leu Glu Arg Val Ala Arg Tyr Ser Met Glu Asp Ala Lys
305                 310                 315                 320

Val Thr Tyr Glu Leu Gly Lys Glu Phe Leu Pro Met Glu Ala Gln Leu
                325                 330                 335

Ser Arg Leu Val Gly Gln Pro Leu Trp Asp Val Ser Arg Ser Ser Thr
                340                 345                 350

Gly Asn Leu Val Glu Trp Phe Leu Leu Arg Lys Ala Tyr Glu Arg Asn
            355                 360                 365

Glu Val Ala Pro Asn Lys Pro Ser Glu Glu Tyr Gln Arg Arg Leu
370                 375                 380

Arg Glu Ser Tyr Thr Gly Gly Phe Val Lys Pro Glu Lys Gly Leu
385                 390                 395                 400

Trp Glu Asn Ile Val Tyr Leu Asp Phe Arg Ala Leu Tyr Pro Ser Ile
                405                 410                 415

Ile Ile Thr His Asn Val Ser Pro Asp Thr Leu Asn Leu Glu Gly Cys
                420                 425                 430

Lys Asn Tyr Asp Ile Ala Pro Gln Val Gly His Lys Phe Cys Lys Asp
            435                 440                 445

Ile Pro Gly Phe Ile Pro Ser Leu Leu Gly His Leu Leu Glu Glu Arg
450                 455                 460

Gln Lys Ile Lys Thr Lys Met Lys Glu Thr Gln Asp Pro Ile Glu Lys
465                 470                 475                 480

Ile Leu Leu Asp Tyr Arg Gln Lys Ala Ile Lys Leu Leu Ala Asn Ser
                485                 490                 495

Phe Tyr Gly Tyr Tyr Gly Tyr Ala Lys Ala Arg Trp Tyr Cys Lys Glu
            500                 505                 510

Cys Ala Glu Ser Val Thr Ala Trp Gly Arg Lys Tyr Ile Glu Leu Val
            515                 520                 525

Trp Lys Glu Leu Glu Glu Lys Phe Gly Phe Lys Val Leu Tyr Ile Asp
530                 535                 540

Thr Asp Gly Leu Tyr Ala Thr Ile Pro Gly Gly Glu Ser Glu Glu Ile
545                 550                 555                 560

Lys Lys Lys Ala Leu Glu Phe Leu Lys Tyr Ile Asn Ala Lys Leu Pro
                565                 570                 575

Gly Ala Leu Glu Leu Glu Tyr Glu Gly Phe Tyr Lys Arg Gly Phe Phe
            580                 585                 590

Val Thr Lys Lys Lys Tyr Ala Val Ile Asp Glu Glu Gly Lys Ile Thr
                595                 600                 605

Thr Arg Gly Leu Glu Ile Val Arg Arg Asp Trp Ser Glu Ile Ala Lys
610                 615                 620
```

```
Glu Thr Gln Ala Arg Val Leu Glu Ala Leu Leu Lys Asp Gly Asp Val
625                 630                 635                 640

Glu Lys Ala Val Arg Ile Val Lys Glu Val Thr Gly Lys Leu Ser Lys
                645                 650                 655

Tyr Glu Val Pro Pro Glu Lys Leu Val Ile His Glu Gln Ile Thr Arg
                660                 665                 670

Asp Leu Lys Asp Tyr Lys Ala Thr Gly Pro His Val Ala Val Ala Lys
                675                 680                 685

Arg Leu Ala Ala Arg Gly Val Lys Ile Arg Pro Gly Thr Val Ile Ser
            690                 695                 700

Tyr Ile Val Leu Lys Gly Ser Gly Arg Ile Gly Asp Arg Ala Ile Pro
705                 710                 715                 720

Phe Asp Glu Phe Asp Pro Thr Lys His Lys Tyr Asp Ala Glu Tyr Tyr
                725                 730                 735

Ile Glu Asn Gln Val Leu Pro Ala Val Glu Arg Ile Leu Arg Ala Phe
            740                 745                 750

Gly Tyr Arg Lys Glu Asp Leu Arg Tyr Gln Lys Thr Arg Gln Val Gly
            755                 760                 765

Leu Ser Ala Trp Leu Lys Pro Lys Gly Thr
        770                 775
```

```
<210> SEQ ID NO 17
<211> LENGTH: 3778
<212> TYPE: DNA
<213> ORGANISM: Artificial Sequence
<220> FEATURE:
<223> OTHER INFORMATION: pLACIQZa

<400> SEQUENCE: 17
```

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcaggcgcg | tcagcgggtg | 120 |
| ttggcgggtg | tcgggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgaatt | cgagctcggt | acccggggat | 420 |
| cctctagagc | cgtaatcatg | gtcatagctg | tttcctgtgt | gaaattgtta | tccgctcaca | 480 |
| attccacaca | acatacgagc | cggaagcata | aagtgtaaag | cctggggtgc | ctaatgagtg | 540 |
| agctaactca | cattaattgc | gttgcgctca | ctgcccgctt | tccagtcggg | aaacctgtcg | 600 |
| tgccagctgc | attaatgaat | cggccaacgc | gcggggagag | gcggtttgcg | tattgggcgc | 660 |
| cagggtggtt | tttcttttca | ccagtgagac | gggcaacagc | tgattgccct | tcaccgcctg | 720 |
| gccctgagag | agttgcagca | agcggtccac | gctggtttgc | cccagcaggc | gaaaatcctg | 780 |
| tttgatggtg | gttgacggcg | ggatataaca | tgagctgtct | tcggtatcgt | cgtatcccac | 840 |
| taccgagata | tccgcaccaa | cgcgcagccc | ggactcggta | atggcgcgca | ttgcgcccag | 900 |
| cgccatctga | tcgttggcaa | ccagcatcgc | agtgggaacg | atgccctcat | tcagcatttg | 960 |
| catggtttgt | tgaaaaccgg | acatggcact | ccagtcgcct | tcccgttccg | ctatcggctg | 1020 |
| aatttgattg | cgagtgagat | atttatgcca | gccagccaga | cgcagacgcg | ccgagacaga | 1080 |
| acttaatggg | cccgctaaca | gcgcgatttg | ctggtgaccc | aatgcgacca | gatgctccac | 1140 |
| gcccagtcgc | gtaccgtctt | catgggagaa | aataatactg | ttgatgggtg | tctggtcaga | 1200 |

```
gacatcaaga ataacgccg gaacattagt gcaggcagct tccacagcaa tggcatcctg    1260
gtcatccagc ggatagttaa tgatcagccc actgacgcgt tgcgcgagaa gattgtgcac    1320
cgccgcttta caggcttcga cgccgcttcg ttctaccatc gacaccacca cgctggcacc    1380
cagttgatcg gcgcgagatt taatcgccgc gacaatttgc gacggcgcgt gcagggccag    1440
actggaggtg gcaacgccaa tcagcaacga ctgtttgccc gccagttgtt gtgccacgcg    1500
gttgggaatg taattcagct ccgccatcgc cgcttccact ttttcccgcg ttttcgcaga    1560
aacgtggctg gcctggttca ccacgcggga aacggtctga taagagacac cggcatactc    1620
tgcgacatcg tataacgtta ctggtttcac attcaccacc ctgaattgac tctcttccgg    1680
gcgctatcat gccataccgc gaaaggtttt gcgccattcg atggtgtcaa cgtaaatgca    1740
tgccgcttcg ccttccggcc accagaatag cctgcgccat gggcttcctc gctcactgac    1800
tcgctgcgct cggtcgttcg gctgcggcga gcggtatcag ctcactcaaa ggcggtaata    1860
cggttatcca cagaatcagg ggataacgca ggaaagaaca tgtgagcaaa aggccagcaa    1920
aaggccagga accgtaaaaa ggccgcgttg ctggcgtttt tccataggct ccgcccccct    1980
gacgagcatc acaaaaatcg acgctcaagt cagaggtggc gaaacccgac aggactataa    2040
agataccagg cgtttccccc tggaagctcc ctcgtgcgct ctcctgttcc gaccctgccg    2100
cttaccggat acctgtccgc ctttctccct tcgggaagcg tggcgctttc tcatagctca    2160
cgctgtaggt atctcagttc ggtgtaggtc gttcgctcca agctgggctg tgtgcacgaa    2220
ccccccgttc agcccgaccg ctgcgcctta tccggtaact atcgtcttga gtccaacccg    2280
gtaagacacg acttatcgcc actggcagca gccactggta acaggattag cagagcgagg    2340
tatgtaggcg gtgctacaga gttcttgaag tggtggccta actacggcta cactagaaga    2400
acagtatttg gtatctgcgc tctgctgaag ccagttacct tcggaaaaag agttggtagc    2460
tcttgatccg gcaaacaaac caccgctggt agcggtggtt tttttgtttg caagcagcag    2520
attacgcgca gaaaaaaagg atctcaagaa gatcctttga tcttttctac ggggtctgac    2580
gctcagtgga acgaaaactc acgttaaggg attttggtca tgagattatc aaaaaggatc    2640
ttcacctaga tccttttaaa ttaaaaatga agttttaaat caatctaaag tatatatgag    2700
taaacttggt ctgacagtta ccaatgctta atcagtgagg cacctatctc agcgatctgt    2760
ctatttcgtt catccatagt tgcctgactc cccgtcgtgt agataactac gatacgggag    2820
ggcttaccat ctggccccag tgctgcaatg ataccgcgag acccacgctc accggctcca    2880
gatttatcag caataaacca gccagccgga agggccgagc gcagaagtgg tcctgcaact    2940
ttatccgcct ccatccagtc tattaattgt tgccgggaag ctagagtaag tagttcgcca    3000
gttaatagtt tgcgcaacgt tgttgccatt gctacaggca tcgtggtgtc acgctcgtcg    3060
tttggtatgg cttcattcag ctccggttcc caacgatcaa ggcgagttac atgatccccc    3120
atgttgtgca aaaaagcggt tagctccttc ggtcctccga tcgttgtcag aagtaagttg    3180
gccgcagtgt tatcactcat ggttatggca gcactgcata attctcttac tgtcatgcca    3240
tccgtaagat gcttttctgt gactggtgag tactcaacca agtcattctg agaatagtgt    3300
atgcggcgac cgagttgctc ttgcccggcg tcaatacggg ataataccgc gccacatagc    3360
agaactttaa aagtgctcat cattggaaaa cgttcttcgg ggcgaaaact ctcaaggatc    3420
ttaccgctgt tgagatccag ttcgatgtaa cccactcgtg cacccaactg atcttcagca    3480
tcttttactt tcaccagcgt ttctgggtga gcaaaaacag gaaggcaaaa tgccgcaaaa    3540
aagggaataa gggcgacacg gaaatgttga atactcatac tcttcctttt tcaatattat    3600
```

```
tgaagcattt atcagggtta ttgtctcatg agcggataca tatttgaatg tatttagaaa    3660
aataaacaaa tagggggttcc gcgcacattt ccccgaaaag tgccacctga cgtctaagaa    3720
accattatta tcatgacatt aacctataaa aataggcgta tcacgaggcc ctttcgtc      3778
```

<210> SEQ ID NO 18
<211> LENGTH: 774
<212> TYPE: PRT
<213> ORGANISM: Thermococcus sp.

<400> SEQUENCE: 18

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Thr Ile Asp Tyr Asp Arg
            20                  25                  30

Asn Phe Glu Pro Tyr Ile Tyr Ala Leu Leu Lys Asp Asp Ser Pro Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Ser Thr Glu Lys Glu Met Ile Lys
            180                 185                 190

Arg Phe Leu Lys Val Val Lys Glu Lys Asp Pro Asp Val Leu Ile Ile
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350
```

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Leu Arg Glu Ser
    370                 375                 380

Tyr Ala Gly Gly Tyr Val Lys Glu Pro Glu Arg Gly Leu Trp Glu Asn
385                 390                 395                 400

Ile Val Tyr Leu Asp Phe Arg Ser Leu Tyr Pro Ser Ile Ile Ile Thr
                405                 410                 415

His Asn Val Ser Pro Asp Thr Leu Asn Arg Glu Gly Cys Glu Glu Tyr
            420                 425                 430

Asp Val Ala Pro Gln Val Gly His Lys Phe Cys Lys Asp Phe Pro Gly
        435                 440                 445

Phe Ile Pro Ser Leu Leu Gly Asp Leu Leu Glu Glu Arg Gln Lys Val
    450                 455                 460

Lys Lys Lys Met Lys Ala Thr Ile Asp Pro Ile Glu Lys Lys Leu Leu
465                 470                 475                 480

Asp Tyr Arg Gln Arg Ala Ile Lys Ile Leu Ala Asn Ser Phe Tyr Gly
                485                 490                 495

Tyr Tyr Gly Tyr Thr Lys Ala Arg Trp Tyr Lys Glu Cys Ala Glu
            500                 505                 510

Ser Val Thr Gly Trp Gly Arg Glu Tyr Ile Glu Thr Ile Arg Glu
        515                 520                 525

Ile Glu Glu Lys Phe Gly Phe Lys Val Leu Tyr Ala Asp Thr Asp Gly
    530                 535                 540

Phe Phe Ala Thr Ile Pro Gly Ala Asp Ala Glu Thr Val Lys Lys Lys
545                 550                 555                 560

Ala Lys Glu Phe Leu Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Val Ile Asp Glu Glu Asp Lys Ile Thr Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Ala Ile Leu Lys His Gly Asp Val Glu Glu Ala
625                 630                 635                 640

Val Arg Ile Val Lys Glu Val Ile Glu Lys Leu Ser Lys Tyr Glu Val
                645                 650                 655

Pro Pro Glu Lys Leu Val Ile Tyr Glu Gln Ile Thr Arg Asp Leu Lys
            660                 665                 670

Asp Tyr Lys Ala Thr Gly Pro His Val Ala Val Ala Lys Arg Leu Ala
        675                 680                 685

Ala Arg Gly Ile Lys Ile Arg Pro Gly Thr Val Ile Ser Tyr Ile Val
    690                 695                 700

Leu Lys Gly Ser Gly Arg Ile Gly Asp Arg Ala Ile Pro Phe Asp Glu
705                 710                 715                 720

Phe Asp Pro Ala Lys His Lys Tyr Asp Ala Glu Tyr Tyr Ile Glu Asn
                725                 730                 735

Gln Val Leu Pro Ala Val Glu Arg Ile Leu Arg Ala Phe Gly Tyr Arg
            740                 745                 750

Lys Glu Asp Leu Arg Tyr Gln Lys Thr Arg Gln Val Gly Leu Gly Ala
        755                 760                 765

Trp Leu Lys Pro Lys Thr

<210> SEQ ID NO 19
<211> LENGTH: 774
<212> TYPE: PRT
<213> ORGANISM: Thermococcus sp.

<400> SEQUENCE: 19

```
Met Ile Leu Asp Ala Asp Tyr Ile Thr Glu Asp Gly Lys Pro Val Ile
1               5                   10                  15
Arg Val Phe Lys Lys Glu Lys Gly Glu Phe Lys Ile Asp Tyr Asp Arg
            20                  25                  30
Asp Phe Glu Pro Tyr Ile Tyr Ala Leu Leu Lys Asp Asp Ser Ala Ile
        35                  40                  45
Glu Asp Ile Lys Lys Ile Thr Ala Glu Arg His Gly Thr Thr Val Arg
    50                  55                  60
Val Thr Arg Ala Glu Arg Val Lys Lys Lys Phe Leu Gly Arg Pro Val
65                  70                  75                  80
Glu Val Trp Lys Leu Tyr Phe Thr His Pro Gln Asp Val Pro Ala Ile
                85                  90                  95
Arg Asp Lys Ile Arg Glu His Pro Ala Val Val Asp Ile Tyr Glu Tyr
            100                 105                 110
Asp Ile Pro Phe Ala Lys Arg Tyr Leu Ile Asp Arg Gly Leu Ile Pro
        115                 120                 125
Met Glu Gly Asp Glu Glu Leu Arg Met Leu Ala Phe Asp Ile Glu Thr
    130                 135                 140
Leu Tyr His Glu Gly Glu Glu Phe Gly Glu Gly Pro Ile Leu Met Ile
145                 150                 155                 160
Ser Tyr Ala Asp Glu Glu Gly Ala Arg Val Ile Thr Trp Lys Asn Ile
                165                 170                 175
Asp Leu Pro Tyr Val Glu Ser Val Ser Thr Glu Lys Glu Met Ile Lys
            180                 185                 190
Arg Phe Leu Lys Val Ile Gln Glu Lys Asp Pro Asp Val Leu Ile Thr
        195                 200                 205
Tyr Asn Gly Asp Asn Phe Asp Phe Ala Tyr Leu Lys Lys Arg Ser Glu
    210                 215                 220
Thr Leu Gly Val Lys Phe Ile Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Thr Val Tyr Glu Ala Ile Phe Gly Gln Pro Lys Glu
        275                 280                 285
Lys Val Tyr Ala Glu Glu Ile Ala Arg Ala Trp Glu Ser Gly Glu Gly
    290                 295                 300
Leu Glu Arg Val Ala Arg Tyr Ser Met Glu Asp Ala Lys Ala Thr Tyr
305                 310                 315                 320
Glu Leu Gly Lys Glu Phe Phe Pro Met Glu Ala Gln Leu Ser Arg Leu
                325                 330                 335
Val Gly Gln Ser Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Arg Glu Leu Ala Arg Arg Leu Ala Glu Ser
```

```
                370             375             380
Tyr Ala Gly Gly Tyr Val Lys Glu Pro Glu Lys Gly Leu Trp Glu Asn
385                 390                 395                 400

Ile Val Tyr Leu Asp Tyr Lys Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Gln Val Gly His Arg Phe Cys Lys Asp Phe Pro Gly
            435                 440                 445

Phe Ile Pro Ser Leu Leu Gly Asp Leu Leu Glu Glu Arg Gln Lys Val
450                 455                 460

Lys Lys Met Lys Ala Thr Val Asp Pro Ile Glu Arg Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Asn Ala Arg Trp Tyr Cys Arg Glu Cys Ala Glu
            500                 505                 510

Ser Val Thr Ala Trp Gly Arg Gln Tyr Ile Glu Thr Thr Met Arg Glu
            515                 520                 525

Ile Glu Glu Lys Phe Gly Phe Lys Val Leu Tyr Ala Asp Thr Asp Gly
            530                 535                 540

Phe Phe Ala Thr Ile Pro Gly Ala Asp Ala Glu Thr Val Lys Lys Lys
545                 550                 555                 560

Ala Lys Glu Phe Leu Asn Tyr Ile Asn Pro Arg Leu Pro Gly Leu Leu
                565                 570                 575

Glu Leu Glu Tyr Glu Gly Phe Tyr Arg Arg Gly Phe Phe Val Thr Lys
            580                 585                 590

Lys Lys Tyr Ala Val Ile Asp Glu Glu Asp Lys Ile Thr Thr Arg Gly
            595                 600                 605

Leu Glu Ile Val Arg Arg Asp Trp Ser Glu Ile Ala Lys Glu Thr Gln
            610                 615                 620

Ala Arg Val Leu Glu Ala Ile Leu Lys His Gly Asp Val Glu Glu Ala
625                 630                 635                 640

Val Arg Ile Val Lys Glu Val Thr Glu Lys Leu Ser Arg Tyr Glu Val
                645                 650                 655

Pro Pro Glu Lys Leu Val Ile Tyr Glu Gln Ile Thr Arg Asp Leu Arg
            660                 665                 670

Asp Tyr Arg Ala Thr Gly Pro His Val Ala Val Ala Lys Arg Leu Ala
            675                 680                 685

Ala Arg Gly Ile Lys Ile Arg Pro Gly Thr Val Ile Ser Tyr Ile Val
690                 695                 700

Leu Lys Gly Pro Gly Arg Val Gly Asp Arg Ala Ile Pro Phe Asp Glu
705                 710                 715                 720

Phe Asp Pro Ala Lys His Arg Tyr Asp Ala Glu Tyr Tyr Ile Glu Asn
                725                 730                 735

Gln Val Leu Pro Ala Val Glu Arg Ile Leu Arg Ala Phe Gly Tyr Arg
            740                 745                 750

Lys Glu Asp Leu Arg Tyr Gln Lys Thr Lys Gln Ala Gly Leu Gly Ala
            755                 760                 765

Trp Leu Lys Pro Lys Thr
    770

<210> SEQ ID NO 20
<211> LENGTH: 774
```

<212> TYPE: PRT
<213> ORGANISM: Thermococcus litoralis

<400> SEQUENCE: 20

```
Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Tyr Lys Arg Arg Leu Arg
    370                 375                 380

Thr Thr Tyr Leu Gly Gly Tyr Val Lys Glu Pro Glu Lys Gly Leu Trp
385                 390                 395                 400
```

```
Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
        435                 440                 445

Pro Gly Phe Ile Pro Ser Ile Leu Gly Asp Leu Ile Ala Met Arg Gln
    450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
        515                 520                 525

Arg Glu Ile Glu Glu Lys Phe Gly Phe Lys Val Leu Tyr Ala Asp Thr
    530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
    610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
        675                 680                 685

Leu Ala Ala Arg Gly Ile Lys Val Lys Pro Gly Thr Ile Ile Ser Tyr
    690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
    770

<210> SEQ ID NO 21
<211> LENGTH: 775
<212> TYPE: PRT
<213> ORGANISM: Pyrococcus sp. GB-D

<400> SEQUENCE: 21
```

-continued

```
Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Lys Asp Asp Ser Gln Ile
            35                  40                  45

Asp Glu Val Arg Lys Ile Thr Ala Glu Arg His Gly Lys Ile Val Arg
        50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430
```

```
Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Glu Ile
        450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
            530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
            610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
        690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
            755                 760                 765

Trp Leu Asn Ile Lys Lys Lys
    770                 775

<210> SEQ ID NO 22
<211> LENGTH: 776
<212> TYPE: PRT
<213> ORGANISM: Thermococcus sp.

<400> SEQUENCE: 22

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30
```

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
 50                  55                  60

Val Lys Arg Ala Glu Lys Val Gln Lys Lys Phe Leu Gly Arg Pro Ile
 65                  70                  75                  80

Glu Val Trp Lys Leu Tyr Phe Asn His Pro Gln Asp Val Pro Ala Ile
                85                  90                  95

Arg Asp Arg Ile Arg Glu His Pro Ala Val Val Asp Ile Tyr Glu Tyr
               100                 105                 110

Asp Ile Pro Phe Ala Lys Arg Tyr Leu Ile Asp Lys Gly Leu Ile Pro
           115                 120                 125

Met Glu Gly Asp Glu Glu Leu Thr Met Leu Ala Phe Asp Ile Glu Thr
       130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
               165                 170                 175

Asp Leu Pro Tyr Val Asp Val Val Ser Thr Glu Lys Glu Met Ile Lys
           180                 185                 190

Arg Phe Leu Arg Val Val Arg Glu Lys Asp Pro Asp Val Leu Ile Thr
       195                 200                 205

Tyr Asn Gly Asp Asn Phe Asp Phe Ala Tyr Leu Lys Lys Arg Cys Glu
   210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
               245                 250                 255

His Phe Asp Leu Tyr Pro Val Ile Arg Arg Thr Ile Asn Leu Pro Thr
           260                 265                 270

Tyr Thr Leu Glu Ala Val Tyr Glu Ala Val Phe Gly Lys Pro Lys Glu
       275                 280                 285

Lys Val Tyr Ala Glu Glu Ile Ala Gln Ala Trp Glu Ser Gly Glu Gly
   290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
               325                 330                 335

Ile Gly Gln Ser Leu Trp Asp Val Ser Arg Ser Ser Thr Gly Asn Leu
           340                 345                 350

Val Glu Trp Phe Leu Leu Arg Lys Ala Tyr Lys Arg Asn Glu Leu Ala
       355                 360                 365

Pro Asn Lys Pro Asp Glu Arg Glu Leu Ala Arg Arg Leu Arg Gly Gly
   370                 375                 380

Tyr Ala Gly Gly Tyr Val Lys Glu Pro Glu Arg Gly Leu Trp Asp Asn
385                 390                 395                 400

Ile Val Tyr Leu Asp Phe Arg Ser Leu Tyr Pro Ser Ile Ile Ile Thr
               405                 410                 415

His Asn Val Ser Pro Asp Thr Leu Asn Arg Glu Gly Cys Lys Glu Tyr
           420                 425                 430

Asp Val Ala Pro Glu Val Gly His Lys Phe Cys Lys Asp Phe Pro Gly
       435                 440                 445

Phe Ile Pro Ser Leu Leu Gly Asp Leu Leu Glu Glu Arg Gln Lys Ile

```
                    450                 455                 460
Lys Arg Lys Met Lys Ala Thr Val Asp Pro Leu Glu Lys Lys Leu Leu
465                 470                 475                 480

Asp Tyr Arg Gln Arg Ala Ile Lys Ile Leu Ala Asn Ser Phe Tyr Gly
                    485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Glu Tyr Ile Glu Met Val Ile Arg Glu
            515                 520                 525

Leu Glu Glu Lys Phe Gly Phe Lys Val Leu Tyr Ala Asp Thr Asp Gly
530                 535                 540

Leu His Ala Thr Ile Pro Gly Ala Asp Ala Glu Thr Val Lys Lys Lys
545                 550                 555                 560

Ala Lys Glu Phe Leu Lys Tyr Ile Asn Pro Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Val Ile Asp Glu Glu Gly Lys Ile Thr Thr Arg Gly
        595                 600                 605

Leu Glu Ile Val Arg Arg Asp Trp Ser Glu Ile Ala Lys Glu Thr Gln
610                 615                 620

Ala Arg Val Leu Glu Ala Ile Leu Lys His Gly Asp Val Glu Glu Ala
625                 630                 635                 640

Val Arg Ile Val Lys Glu Val Thr Glu Lys Leu Ser Lys Tyr Glu Val
                645                 650                 655

Pro Pro Glu Lys Leu Val Ile His Glu Gln Ile Thr Arg Asp Leu Arg
            660                 665                 670

Asp Tyr Lys Ala Thr Gly Pro His Val Ala Val Ala Lys Arg Leu Ala
        675                 680                 685

Ala Arg Gly Val Lys Ile Arg Pro Gly Thr Val Ile Ser Tyr Ile Val
690                 695                 700

Leu Lys Gly Ser Gly Arg Ile Gly Asp Arg Ala Ile Pro Ala Asp Glu
705                 710                 715                 720

Phe Asp Pro Thr Lys His Arg Tyr Asp Ala Glu Tyr Tyr Ile Glu Asn
                725                 730                 735

Gln Val Leu Pro Ala Val Glu Arg Ile Leu Lys Ala Phe Gly Tyr Arg
            740                 745                 750

Lys Glu Asp Leu Arg Tyr Gln Lys Thr Lys Gln Val Gly Leu Gly Ala
        755                 760                 765

Trp Leu Lys Val Lys Gly Lys Lys
770                 775

<210> SEQ ID NO 23
<211> LENGTH: 774
<212> TYPE: PRT
<213> ORGANISM: Thermococcus sp.

<400> SEQUENCE: 23

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Asp Glu Ile Lys Ala Ile Lys Gly Glu Arg His Gly Lys Ile Val Arg
```

```
                50                  55                  60
Val Val Asp Ala Val Lys Val Lys Lys Phe Leu Gly Arg Asp Val
 65                  70                  75                  80

Glu Val Trp Lys Leu Ile Phe Glu His Pro Gln Asp Val Pro Ala Leu
                 85                  90                  95

Arg Gly Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Ile Pro
                115                 120                 125

Met Glu Gly Asp Glu Glu Leu Lys Leu Met Ala Phe Asp Ile Glu Thr
            130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Ile Val Arg Glu Lys Asp Pro Asp Val Leu Ile Thr
        195                 200                 205

Tyr Asn Gly Asp Asn Phe Asp Leu Pro Tyr Leu Ile Lys Arg Ala Glu
    210                 215                 220

Lys Leu Gly Val Thr Leu Leu Gly Arg Asp Lys Glu His Pro Glu
225                 230                 235                 240

Pro Lys Ile His Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
    290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Glu Arg Asn Glu
        355                 360                 365

Leu Ala Pro Asn Lys Pro Asp Glu Glu Glu Tyr Arg Arg Arg Leu Arg
    370                 375                 380

Thr Thr Tyr Leu Gly Gly Tyr Val Lys Glu Pro Glu Arg Gly Leu Trp
385                 390                 395                 400

Glu Asn Ile Ala Tyr Leu Asp Phe Arg Ser Leu Tyr Pro Ser Ile Ile
                405                 410                 415

Val Thr His Asn Val Ser Pro Asp Thr Leu Glu Arg Glu Gly Cys Lys
            420                 425                 430

Asn Tyr Asp Val Ala Pro Ile Val Gly Tyr Lys Phe Cys Lys Asp Phe
        435                 440                 445

Pro Gly Phe Ile Pro Ser Ile Leu Gly Glu Leu Ile Thr Met Arg Gln
    450                 455                 460

Glu Ile Lys Lys Lys Met Lys Ala Thr Ile Asp Pro Ile Glu Lys Lys
465                 470                 475                 480
```

```
Met Leu Asp Tyr Arg Gln Arg Ala Val Lys Leu Leu Ala Asn Ser Tyr
                485                 490                 495
Tyr Gly Tyr Met Gly Tyr Pro Lys Ala Arg Trp Tyr Ser Lys Glu Cys
            500                 505                 510
Ala Glu Ser Val Thr Ala Trp Gly Arg His Tyr Ile Glu Met Thr Ile
        515                 520                 525
Lys Glu Ile Glu Glu Lys Phe Gly Phe Lys Val Leu Tyr Ala Asp Thr
    530                 535                 540
Asp Gly Phe Tyr Ala Thr Ile Pro Gly Glu Lys Pro Glu Thr Ile Lys
545                 550                 555                 560
Lys Lys Ala Lys Glu Phe Leu Lys Tyr Ile Asn Ser Lys Leu Pro Gly
                565                 570                 575
Leu Leu Glu Leu Glu Tyr Glu Gly Phe Tyr Leu Arg Gly Phe Phe Val
            580                 585                 590
Ala Lys Lys Arg Tyr Ala Val Ile Asp Glu Glu Gly Arg Ile Thr Thr
        595                 600                 605
Arg Gly Leu Glu Val Val Arg Arg Asp Trp Ser Glu Ile Ala Lys Glu
    610                 615                 620
Thr Gln Ala Lys Val Leu Glu Ala Ile Leu Lys Glu Asp Ser Val Glu
625                 630                 635                 640
Lys Ala Val Glu Ile Val Lys Asp Val Glu Glu Ile Ala Lys Tyr
                645                 650                 655
Gln Val Pro Leu Glu Lys Leu Val Ile His Glu Gln Ile Thr Lys Asp
            660                 665                 670
Leu Ser Glu Tyr Lys Ala Ile Gly Pro His Val Ala Ile Ala Lys Arg
        675                 680                 685
Leu Ala Ala Lys Gly Ile Lys Val Arg Pro Gly Thr Ile Ile Ser Tyr
    690                 695                 700
Ile Val Leu Arg Gly Ser Gly Lys Ile Ser Asp Arg Val Ile Leu Leu
705                 710                 715                 720
Ser Glu Tyr Asp Pro Lys Lys His Lys Tyr Asp Pro Asp Tyr Tyr Ile
                725                 730                 735
Glu Asn Gln Val Leu Pro Ala Val Leu Arg Ile Leu Glu Ala Phe Gly
            740                 745                 750
Tyr Arg Lys Glu Asp Leu Lys Tyr Gln Ser Ser Lys Gln Val Gly Leu
        755                 760                 765
Asp Ala Trp Leu Lys Lys
    770

<210> SEQ ID NO 24
<211> LENGTH: 17
<212> TYPE: DNA
<213> ORGANISM: Artificial Sequence
<220> FEATURE:
<223> OTHER INFORMATION: Primer

<400> SEQUENCE: 24
gttttcccag tcacgac                                                  17

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
ggtatcttta tagtcctgtc g                                             21
```

```
<210> SEQ ID NO 26
<211> LENGTH: 40
<212> TYPE: DNA
<213> ORGANISM: Artificial Sequence
<220> FEATURE:
<223> OTHER INFORMATION: Primer

<400> SEQUENCE: 26
aacgccaggg ttttcccagt cacgacgttg taaaacgacg                              40
```

MODIFIED DNA POLYMERASES

The present application is a national phase entry of international application serial number PCT/US2009/063169, filed Nov. 3, 2009 which claims priority to U.S. Provisional patent application Ser. No. 61/110,883, filed Nov. 3, 2008, the entire disclosure of which is incorporated herein by reference.

The present specification makes reference to a Sequence Listing (submitted electronically as a .txt file named "Sequence Listing.txt" on May 3, 2011). The .txt file was generated on Nov. 9, 2009 and is 122 kb in size. The entire contents of the Sequence Listing are herein incorporated by reference.

BACKGROUND OF THE INVENTION

DNA polymerases are a family of enzymes that use single-stranded DNA as a template to synthesize the complementary DNA strand. In particular, DNA polymerases can add free nucleotides to the 3' end of a newly-forming strand resulting in elongation of the new strand in a 5'-3' direction. Most DNA polymerases are multifunctional proteins that possess both polymerizing and exonucleolytic activities. For example, many DNA polymerases have 3'→5' exonuclease activity. These polymerases can recognize an incorrectly incorporated nucleotide and the 3'→5' exonuclease activity of the enzyme allows the incorrect nucleotide to be excised (this activity is known as proofreading). Following nucleotide excision, the polymerase can re-insert the correct nucleotide and replication can continue. Many DNA polymerases also have 5'→3' exonuclease activity.

DNA polymerases, like other natural enzymes, have evolved over millions of years to be efficient in their natural cellular environment. Many of them are almost perfectly adapted to work in that environment. In such an environment the way that the protein can evolve is constrained by a number of requirements; the protein has to interact with other cellular components, it has to function in the cytoplasm (i.e., particular pH, ionic strength, in the presence of particular compounds, etc.) and it cannot cause lethal or disadvantageous side effects that detract from the fitness of the parent organism as a whole.

When DNA polymerases are removed from their natural environment and used in industrial or research applications, the environment and conditions under which the enzyme is operating is inevitably vastly different than those in which it evolved. Many of the constraints that limited the evolutionary direction the protein could take fall away. Therefore, there is vast potential for improvement of DNA polymerases for use in industrial or research applications.

SUMMARY OF THE INVENTION

The present invention provides improved DNA polymerases that may be better suited for applications in recombinant DNA technologies. Among other things, the present invention provides modified DNA polymerases based on directed evolution experiments designed to select mutations that confer advantageous phenotypes under environment and conditions used in industrial or research applications.

In one aspect, the present invention provides modified DNA polymerases containing one or more amino acid alterations (e.g., substitution, deletion or insertion) corresponding to one or more positions identified from the positions identified in Tables 1, 2, 3, 4, 5, or 6 relative to the corresponding wild-type or parental enzyme. In some embodiments, such amino acid alterations alter (e.g., increase or decrease) enzyme activity, fidelity, processivity, elongation rate, stability, primer-dimer formation, salt resistance, solubility, expression efficiency, folding robustness, thermostability, polymerization activity, concentration robustness, resistance to impurities, strand-displacement activity, knock-out of uracil read-ahead function, nucleotide selectivity, and/or other properties and characteristics involved in the process of DNA polymerization.

In some embodiments, modified DNA polymerases of the invention contain amino acid alterations at one or more positions corresponding to F752, F591, E668, G638, E734, E377, T609, P454, E582 and/or G715 of SEQ ID NO:16 (the Kofu amino acid sequence shown in the Sequences section).

In some embodiments, modified DNA polymerases of the invention contain one or more amino acid substitutions selected from Tables 2, 3, 4, 5, or 6. In some embodiments, modified DNA polymerases of the invention contain one or more amino acid substitutions selected from F752Y, F591L, F591I, E668V, G638R, G638V, E734K, E377K, T609I, T609A, P454S, E582K and/or G715R.

In some embodiments, the present invention provides modified DNA polymerases containing one or more amino acid alterations (e.g., substitutions, deletions or insertions) at one or more positions selected from the positions corresponding to E377, V356, E386, F591, G638, E668, E734, E738, F752, and/or W772 of SEQ ID NO:16, wherein the one or more amino acid alterations increase the enzyme activity of the DNA polymerases. In some embodiments, modified DNA polymerases in accordance with the invention contain one or more amino acid substitutions selected from the substitutions corresponding to F752Y, F591L, F591I, G638V, G638R, E668V, E734K, V356M, E738G, E386K, W772R, and/or E377K of SEQ ID NO:16.

In some embodiments, the present invention provides modified DNA polymerases containing one or more amino acid alterations (e.g., substitutions, deletions or insertions) at one or more positions selected from the positions corresponding to D346, V356, E377, A494, A550, F591, G638, E668, E734, and/or E738, of SEQ ID NO:16, wherein the one or more amino acid alterations increase the DNA binding affinity of the DNA polymerases. In some embodiments, modified DNA polymerases in accordance with the invention contain one or more amino acid substitutions selected from the substitutions corresponding to F591I, F591L, A550V, E377K, A494V, E734K, G638V, G638R, E668V, D346G, V356M, E738G, E734G, and/or E734N of SEQ ID NO:16.

In some embodiments, the present invention provides modified DNA polymerases containing one or more amino acid alterations (e.g., substitutions, deletions or insertions) at one or more positions selected from the positions corresponding to S376, R410, E582, E652, A679, or T680 of SEQ ID NO.14, wherein the one or more amino acid alterations decrease the DNA binding affinity of the DNA polymerase. In some embodiments, modified DNA polymerases in accordance with the invention contain one or more amino acid alterations selected from the substitutions corresponding to R410H, E582K, E652K, A679V, A679T, S376G, and/or T680I of SEQ ID NO:16.

In some embodiments, the present invention provides modified DNA polymerases containing one or more amino acid alterations (e.g., substitutions, deletions or insertions) at positions corresponding to S376, V441, F591, G638, E668, T680, and/or F752, of SEQ ID NO.14, wherein the one or more amino acid alterations decrease the fidelity of the DNA polymerase.

In some embodiments, modified DNA polymerases of the invention contain one or more amino acid substitutions selected from the substitutions corresponding to F591L, F752Y, F591I, E668V, V441I, G638R, S376G and/or T680I, of SEQ ID NO.16.

In some embodiments, modified DNA polymerases of the present invention are modified from a naturally-occurring polymerase (e.g., a naturally-occurring euryarchaeal family B polymerase) including, but not limited to, the naturally-occurring polymerases isolated from *P. kodakaraensis, P. furiosus, T. gorgonarius, T. zilligii, T. litoralis* "Vent™", *P. GB-D* "Deep Vent", *T. 9N-7, T. aggregans, T. barossii, T. fumicolans, T. celer, Pyrococcus* sp. strain ST700, *T. pacificus, P. abyssi, T. profundus, T. siculi, T. hydrothermalis, Thermococcus* sp. strain GE8, *T. thioreducens, P. horikoshii* or *T. onnurineus* NA1, or truncated versions thereof.

In some embodiments, modified DNA polymerases of the invention are modified from a recombinant or engineered DNA polymerase including, but not limited to, chimeric DNA polymerases, fusion polymerases, and other modified polymerases (e.g., polymerases that contain deletions, substitutions or insertions but retain polymerase activity). In some embodiments, modified DNA polymerases of the invention are modified from a chimeric DNA polymerase containing SEQ ID NO.16.

In another aspect, the present invention provides methods of engineering modified DNA polymerases based on various mutations described herein. In some embodiments, methods of the invention include steps of: (a) modifying a DNA polymerase by introducing one or more amino acid alterations at one or more positions corresponding to the positions identified in Table 1; (b) determining the enzyme activity, fidelity, processivity, elongation rate, stability, primer-dimer formation, salt resistance, and/or solubility of the modified DNA polymerase from step (a). In some embodiments, the present invention provides various modified DNA polymerases engineered according to the methods described herein.

The present invention also provides kits and compositions containing various modified polymerases described herein and uses thereof. In addition, the present invention provides nucleotide sequences encoding various modified polymerases described herein and vectors and/or cells containing the nucleotide sequences according to the invention.

BRIEF DESCRIPTION OF THE DRAWINGS

The drawings are for illustration purposes only not for limitation.

FIG. 1 depicts an alignment of exemplary naturally-occurring type B DNA polymerases and exemplary chimeric DNA polymerases, Kofu and Pod.

DEFINITIONS

Amino acid: As used herein, term "amino acid," in its broadest sense, refers to any compound and/or substance that can be incorporated into a polypeptide chain. In some embodiments, an amino acid has the general structure $H_2N-C(H)(R)-COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical without adversely affecting their activity. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide. It should be noted that all amino acid residue sequences are represented herein by formulae whose left and right orientation is in the conventional direction of amino-terminus to carboxy-terminus.

Base Pair (bp): As used herein, base pair refers to a partnership of adenine (A) with thymine (T), or of cytosine (C) with guanine (G) in a double stranded DNA molecule.

Chimeric polymerase: As used herein, the term "chimeric polymerase" (also referred to as "chimera") refers to any recombinant polymerase containing at least a first amino acid sequence derived from a first DNA polymerase and a second amino acid sequence derived from a second DNA polymerase. Typically, the first and second DNA polymerases are characterized with at least one distinct functional characteristics (e.g., processivity, elongation rate, fidelity). As used herein, a sequence derived from a DNA polymerase of interest refers to any sequence found in the DNA polymerase of interest, or any sequence having at least 70% (e.g., at least 75%, 80%, 85%, 90%, 91%, 92%, 93%, 94%, 95%, 96%, 97%, 98%, 99%) identical to an amino acid sequence found in the DNA polymerase of interest. A "chimeric polymerase" according to the invention may contain two or more amino acid sequences from related or similar polymerases (e.g., proteins sharing similar sequences and/or structures), joined to form a new functional protein. A "chimeric polymerase" according to the invention may contain two or more amino acid sequences from unrelated polymerases, joined to form a new functional protein. For example, a chimeric polymerase of the invention may be an "interspecies" or "intergenic" fusion of protein structures expressed by different kinds of organisms.

Complementary: As used herein, the term "complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

DNA binding affinity: As used herein, the term "DNA-binding affinity" typically refers to the activity of a DNA polymerase in binding DNA nucleic acid. In some embodiments, DNA binding activity can be measured in a two band-shift assay. For example, in some embodiments (based on the assay of Guagliardi et al. (1997) *J. Mol. Biol.* 267:841-848), double-stranded nucleic acid (the 452-bp HindIII-EcoRV fragment from the *S. solfataricus* lacS gene) is labeled with $^{32}P$ to a specific activity of at least about $2.5 \times 10^7$ cpm/μg (or at least about 4000 cpm/fmol) using standard methods. See, e.g., Sambrook et al. (2001) Molecular Cloning: A Laboratory Manual (3$^{rd}$ ed., Cold Spring Harbor Laboratory Press, NY) at 9.63-9.75 (describing end-labeling of nucleic acids). A reaction mixture is prepared containing at least about 0.5 μg of the polypeptide in about 10 μl of binding buffer (50 mM sodium phosphate buffer (pH 8.0), 10% glycerol, 25 mM KCl, 25 mM MgCl$_2$). The reaction mixture is heated to 37° C. for 10 min. About $1 \times 10^4$ to $5 \times 10^4$ cpm (or about 0.5-2 ng) of the labeled double-stranded nucleic acid is added to the reaction mixture and incubated for an additional 10 min. The reaction mixture is loaded onto a native polyacrylamide gel in 0.5× Tris-borate buffer. The reaction mixture is subjected to electrophoresis at room temperature. The gel is dried and subjected to autoradiography using standard methods. Any detectable decrease in the mobility of the labeled double-stranded nucleic acid indicates formation of a binding complex between the polypeptide and the double-stranded nucleic acid. Such nucleic acid binding activity may be quantified using standard densitometric methods to measure the amount of radioactivity in the binding complex relative to the total amount of radioactivity in the initial reaction mixture. Other methods of measuring DNA binding affinity are known in the art (see, e.g. Kong et al. (1993) *J. Biol. Chem.* 268(3): 1965-1975).

Elongation rate: As used herein, the term "elongation rate" refers to the average speed at which a DNA polymerase extends a polymer chain. As used herein, a high elongation rate refers to an elongation rate higher than 25 nt/s (e.g., higher than 30, 35, 40, 45, 50, 55, 60, 65, 70, 75, 80, 85, 90, 95, 100, 105, 110, 115, 120, 125, 130, 135, 140 nt/s). As used in this application, the terms "elongation rate" and "speed" are used inter-changeably.

Enzyme activity: As used herein, the term "enzyme activity" refers to the specificity and efficiency of a DNA polymerase. Enzyme activity of a DNA polymerase is also referred to as "polymerase activity," which typically refers to the activity of a DNA polymerase in catalyzing the template-directed synthesis of a polynucleotide. Enzyme activity of a polymerase can be measured using various techniques and methods known in the art. For example, serial dilutions of polymerase can be prepared in dilution buffer (e.g., 20 mM Tris.Cl, pH 8.0, 50 mM KCl, 0.5% NP 40, and 0.5% Tween-20). For each dilution, 5 µl can be removed and added to 45 µl of a reaction mixture containing 25 mM TAPS (pH 9.25), 50 mM KCl, 2 mM MgCl$_2$, 0.2 mM dATP, 0.2 mM dGTP, 0.2 mM dTTP, 0.1 mM dCTP, 12.5 µg activated DNA, 100 µM [$\alpha$-$^{32}$P]dCTP (0.05 µCi/nmol) and sterile deionized water. The reaction mixtures can be incubated at 37° C. (or 74° C. for thermostable DNA polymerases) for 10 minutes and then stopped by immediately cooling the reaction to 4° C. and adding 10 µl of ice-cold 60 mM EDTA. A 25 µl aliquot can be removed from each reaction mixture. Unincorporated radioactively labeled dCTP can be removed from each aliquot by gel filtration (Centri-Sep, Princeton Separations, Adelphia, N.J.). The column eluate can be mixed with scintillation fluid (1 ml). Radioactivity in the column eluate is quantified with a scintillation counter to determine the amount of product synthesized by the polymerase. One unit of polymerase activity can be defined as the amount of polymerase necessary to synthesize 10 nmole of product in 30 minutes (Lawyer et al. (1989) *J. Biol. Chem.* 264:6427-647). Other methods of measuring polymerase activity are known in the art (see, e.g. Sambrook et al. (2001) Molecular Cloning: A Laboratory Manual (3.sup.rd ed., Cold Spring Harbor Laboratory Press, NY)).

Fidelity: As used herein, the term "fidelity" refers to the accuracy of DNA polymerization by template-dependent DNA polymerase. The fidelity of a DNA polymerase is typically measured by the error rate (the frequency of incorporating an inaccurate nucleotide, i.e., a nucleotide that is not incorporated at a template-dependent manner). The accuracy or fidelity of DNA polymerization is maintained by both the polymerase activity and the 3'-5' exonuclease activity of a DNA polymerase. The term "high fidelity" refers to an error rate less than $4.45 \times 10^{-6}$ (e.g., less than $4.0 \times 10^{-6}$, $3.5 \times 10^{-6}$, $3.0 \times 10^{-6}$, $2.5 \times 10^{-6}$, $2.0 \times 10^{-6}$, $1.5 \times 10^{-6}$, $1.0 \times 10^{-6}$, $0.5 \times 10^{-6}$) mutations/nt/doubling. The fidelity or error rate of a DNA polymerase may be measured using assays known to the art. For example, the error rates of DNA polymerases can be tested using the lacI PCR fidelity assay described in Cline, J. et al. (96) NAR 24: 3546-3551. Briefly, a 1.9 kb fragment encoding the lacIOlacZa target gene is amplified from pPRIAZ plasmid DNA using 2.5 U DNA polymerase (i.e. amount of enzyme necessary to incorporate 25 nmoles of total dNTPs in 30 min at 72° C.) in the appropriate PCR buffer. The lacI-containing PCR products are then cloned into lambda GT10 arms, and the percentage of lacI mutants (MF, mutation frequency) is determined in a color screening assay, as described (Lundberg, K. S., Shoemaker, D. D., Adams, M. W. W., Short, J. M., Sorge, J. A., and Mathur, E. J. (1991) Gene 180: 1-8). Error rates are expressed as mutation frequency per by per duplication (MF/bp/d), where by is the number of detectable sites in the lad gene sequence (349) and d is the number of effective target doublings. Similar to the above, any plasmid containing the lacIOlacZa target gene can be used as template for the PCR. The PCR product may be cloned into a vector different from lambda GT (e.g., plasmid) that allows for blue/white color screening.

Fusion DNA polymerase: As used herein, the term "fusion DNA polymerase" refers to any DNA polymerase that is combined (e.g., covalently or non-covalently) with one or more protein domains having a desired activity (e.g., DNA-binding, stabilizing template-primer complexes, hydrolyzing dUTP). In some embodiments, the one or more protein domains are derived from a non-polymerase protein. Typically, fusion DNA polymerases are generated to improve certain functional characteristics (e.g., processivity, elongation rate, fidelity, salt-resistance, etc.) of a DNA polymerase.

Modified DNA polymerase: As used herein, the term "modified DNA polymerase" refers to a DNA polymerase originated from another (i.e., parental) DNA polymerase and contains one or more amino acid alterations (e.g., amino acid substitution, deletion, or insertion) compared to the parental DNA polymerase. In some embodiments, a modified DNA polymerases of the invention is originated or modified from a naturally-occurring or wild-type DNA polymerase. In some embodiments, a modified DNA polymerase of the invention is originated or modified from a recombinant or engineered DNA polymerase including, but not limited to, chimeric DNA polymerase, fusion DNA polymerase or another modified DNA polymerase. Typically, a modified DNA polymerase has at least one changed phenotypes compared to the parental polymerase.

Mutation: As used herein, the term "mutation" refers to a change introduced into a parental sequence, including, but not limited to, substitutions, insertions, deletions (including truncations). The consequences of a mutation include, but are not limited to, the creation of a new character, property, function, phenotype or trait not found in the protein encoded by the parental sequence.

Mutant: As used herein, the term "mutant" refers to a modified protein which displays altered characteristics when compared to the parental protein.

Joined: As used herein, "joined" refers to any method known in the art for functionally connecting polypeptide domains, including without limitation recombinant fusion with or without intervening domains, inter-mediated fusion, non-covalent association, and covalent bonding, including disulfide bonding, hydrogen bonding, electrostatic bonding, and conformational bonding.

Nucleotide: As used herein, a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence," and is represented herein by a formula whose left to right orientation is in the conventional direction of 5'-terminus to 3'-terminus.

Oligonucleotide or Polynucleotide: As used herein, the term "oligonucleotide" is defined as a molecule including two or more deoxyribonucleotides and/or ribonucleotides, preferably more than three. Its exact size will depend on many factors, which in turn depend on the ultimate function or use of the oligonucleotide. The oligonucleotide may be derived synthetically or by cloning. As used herein, the term "polynucleotide" refers to a polymer molecule composed of nucleotide monomers covalently bonded in a chain. DNA (deoxyribonucleic acid) and RNA (ribonucleic acid) are examples of polynucleotides.

Polymerase: As used herein, a "polymerase" refers to an enzyme that catalyzes the polymerization of nucleotide (i.e., the polymerase activity). Generally, the enzyme will initiate synthesis at the 3'-end of the primer annealed to a polynucleotide template sequence, and will proceed toward the 5' end of the template strand. A "DNA polymerase" catalyzes the polymerization of deoxynucleotides.

Primer: As used herein, the term "primer" refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, e.g., in the presence of four different nucleotide triphosphates and thermostable enzyme in an appropriate buffer ("buffer" includes pH, ionic strength, cofactors, etc.) and at a suitable temperature. The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the thermostable enzyme. The exact lengths of the primers will depend on many factors, including temperature, source of primer and use of the method. For example, depending on the complexity of the target sequence, the oligonucleotide primer typically contains 15-25 nucleotides, although it may contain more or few nucleotides. Short primer molecules generally require colder temperatures to form sufficiently stable hybrid complexes with template.

Processivity: As used herein, "processivity" refers to the ability of a polymerase to remain attached to the template and perform multiple modification reactions. "Modification reactions" include but are not limited to polymerization, and exonucleolytic cleavage. In some embodiments, "processivity" refers to the ability of a DNA polymerase to perform a sequence of polymerization steps without intervening dissociation of the enzyme from the growing DNA chains. Typically, "processivity" of a DNA polymerase is measured by the length of nucleotides (for example 20 nts, 300 nts, 0.5-1 kb, or more) that are polymerized or modified without intervening dissociation of the DNA polymerase from the growing DNA chain. "Processivity" can depend on the nature of the polymerase, the sequence of a DNA template, and reaction conditions, for example, salt concentration, temperature or the presence of specific proteins. As used herein, the term "high processivity" refers to a processivity higher than 20 nts (e.g., higher than 40 nts, 60 nts, 80 nts, 100 nts, 120 nts, 140 nts, 160 nts, 180 nts, 200 nts, 220 nts, 240 nts, 260 nts, 280 nts, 300 nts, 320 nts, 340 nts, 360 nts, 380 nts, 400 nts, or higher) per association/disassociation with the template. Processivity can be measured according the methods defined herein and in WO 01/92501 A1.

Synthesis: As used herein, the term "synthesis" refers to any in vitro method for making new strand of polynucleotide or elongating existing polynucleotide (i.e., DNA or RNA) in a template dependent manner Synthesis, according to the invention, includes amplification, which increases the number of copies of a polynucleotide template sequence with the use of a polymerase. Polynucleotide synthesis (e.g., amplification) results in the incorporation of nucleotides into a polynucleotide (i.e., a primer), thereby forming a new polynucleotide molecule complementary to the polynucleotide template. The formed polynucleotide molecule and its template can be used as templates to synthesize additional polynucleotide molecules. "DNA synthesis," as used herein, includes, but is not limited to, PCR, the labeling of polynucleotide (i.e., for probes and oligonucleotide primers), polynucleotide sequencing.

Template DNA molecule: As used herein, the term "template DNA molecule" refers to a strand of a nucleic acid from which a complementary nucleic acid strand is synthesized by a DNA polymerase, for example, in a primer extension reaction.

Template-dependent manner: As used herein, the term "template-dependent manner" refers to a process that involves the template dependent extension of a primer molecule (e.g., DNA synthesis by DNA polymerase). The term "template-dependent manner" typically refers to polynucleotide synthesis of RNA or DNA wherein the sequence of the newly synthesized strand of polynucleotide is dictated by the well-known rules of complementary base pairing (see, for example, Watson, J. D. et al., In: Molecular Biology of the Gene, 4th Ed., W. A. Benjamin, Inc., Menlo Park, Calif. (1987)).

Thermostable enzyme: As used herein, the term "thermostable enzyme" refers to an enzyme which is stable to heat (also referred to as heat-resistant) and catalyzes (facilitates) polymerization of nucleotides to form primer extension products that are complementary to a polynucleotide template sequence. Typically, thermostable stable polymerases are preferred in a thermocycling process wherein double stranded nucleic acids are denatured by exposure to a high temperature (e.g., about 95 C) during the PCR cycle. A thermostable enzyme described herein effective for a PCR amplification reaction satisfies at least one criteria, i.e., the enzyme do not become irreversibly denatured (inactivated) when subjected to the elevated temperatures for the time necessary to effect denaturation of double-stranded nucleic acids. Irreversible denaturation for purposes herein refers to permanent and complete loss of enzymatic activity. The heating conditions necessary for denaturation will depend, e.g., on the buffer salt concentration and the length and nucleotide composition of the nucleic acids being denatured, but typically range from about 90° C. to about 96° C. for a time depending mainly on the temperature and the nucleic acid length, typically about 0.5 to four minutes. Higher temperatures may be tolerated as the buffer salt concentration and/or GC composition of the nucleic acid is increased. In some embodiments, thermostable enzymes will not become irreversibly denatured at about 90° C.-100° C. Typically, a thermostable enzyme suitable for the invention has an optimum temperature at which it functions that is higher than about 40° C., which is the temperature below which hybridization of primer to template is promoted, although, depending on (1) magnesium and salt, concentrations and (2) composition and length of primer, hybridization can occur at higher temperature (e.g., 45° C.-70° C.). The higher the temperature optimum for the enzyme, the greater the specificity and/or selectivity of the primer-directed extension process. However, enzymes that are active below 40° C. (e.g., at 37° C.) are also with the scope of this invention provided they are heat-stable. In some embodiments, the optimum temperature ranges from about 50° C. to 90° C. (e.g., 60° C.-80° C.).

Wild-type: As used herein, the term "wild-type" refers to a gene or gene product which has the characteristics of that gene or gene product when isolated from a naturally-occurring source.

DETAILED DESCRIPTION OF THE INVENTION

The present invention provides, among other things, modified DNA polymerases containing amino acid alterations based on mutations identified in directed evolution experiments designed to select enzymes that are better suited for applications in recombinant DNA technologies.

As described in the Examples section, the present inventors have successfully developed directed DNA polymerase evolution experiments by mimicking the typical or less-than typical environments and conditions under which an enzyme is usually used or expected to be used in real-life industrial or research applications. Typically, no specific selection pressure is deliberately applied in the directed evolution experiments to increase the diversity of mutations that are selected for.

As discussed in the Examples, various mutations have been observed during the selection process (see Table 1). Many mutations are selected for a wide range of advantages relating to enzyme characteristics including, but not limited to, expression efficiency, solubility and folding robustness, thermostability, polymerization activity, processivity, speed (elongation rate), concentration robustness, resistance to impurities, fidelity, avoidance of primer-dimers, strand-displacement activity, knock-out of uracil read-ahead function, nucleotide selectivity, and other properties and characteristics involved in the process of DNA polymerization (see Table 2).

It is contemplated that the mutations identified herein confer a variety of phenotypes that would make DNA polymerases better suited for applications in recombinant DNA technologies. For example, mutations identified in accordance with the present invention may confer enzymatic phenotypes related to the selective advantages described herein. Indeed, the present inventors have identified or expect to identify mutant polymerases that express well, are more soluble, that display higher activity, fidelity, processivity and/or speed, that are active over a wide range of concentrations, that are resistant to impurities, that work over a range of concentrations and have a higher fidelity, and other phenotypes that may not be immediately measurable. Since many of these phenotypes may depend on the manner in which the DNA and polymerase interact, it is contemplated that many of the mutations identified in accordance with the present invention may affect DNA-polymerase binding characteristics.

In addition, it is contemplated that mutations identified according to the present invention may confer enzymatic phenotypes not directly related to the selective advantages described herein. For example, some phenotypes may confer no advantage, but merely be a side effect of the advantageous mutation. In addition, some mutants may display phenotypes that could be considered disadvantageous. For example, some mutations confer an advantage (for example, high activity), but this advantage comes at a cost (for example, high error-rate). If the advantage outweighs the disadvantage, the mutation will still be selected for. Such mutations may have commercial uses. For example, a low fidelity enzyme could be used in error prone PCR (e.g., for mutagenesis).

Exemplary mutations having specific phenotypes are shown in Tables 3, 4, 5 and 6.

It is further contemplated that, since many DNA polymerases have similar sequences, structures and functional domains, mutations and/or the positions where mutations occur identified herein can serve as bases for modification of DNA polymerases in general. For example, same or similar mutations, as well as other alterations, may be introduced at the corresponding positions in various DNA polymerases to generate modified enzymes that are better adapted for recombinant use.

DNA Polymerases

DNA polymerases in accordance with the present invention may be modified from any types of DNA polymerases including, but not limited to, naturally-occurring wild-type DNA polymerases, recombinant DNA polymerase or engineered DNA polymerases such as chimeric DNA polymerases, fusion DNA polymerases, or other modified DNA polymerases (e.g., DNA polymerases that contain deletions (N- or C-terminal or internal deletions), substitutions or insertains but retain polymerase activity).

Naturally-Occurring DNA Polymerases

In some embodiments, DNA polymerases suitable for the invention are naturally-occurring DNA polymerases (e.g., thermostable DNA polymerases). Typically, DNA polymerases are grouped into six families: A, B, C, D, X and Y. Families A, B, C are grouped based on their amino acid sequence homologies to *E. coli* polymerases I, II, and III, respectively. Family X has no homologous *E. coli* polymerases. In some embodiments, DNA polymerases suitable for the present invention are family B DNA polymerases. Family B polymerases include, but are not limited to, *E. coli* pol II, archaeal polymerases, PRD1, phi29, M2, T4 bacteriophage DNA polymerases, eukaryotic polymerases α, Δ, ϵ, and many viral polymerases. In some embodiments, DNA polymerases suitable for the invention are archaeal polymerases (e.g., euryarchaeal polymerases).

Suitable exemplary archaeal polymerases include, but are not limited to, DNA polymerases from archaea (e.g., *Thermococcus litoralis* (Vent™, GenBank: AAA72101), *Pyrococcus furiosus* (Pfu, GenBank: D12983, BAA02362), *Pyrococcus woesii*, *Pyrococcus* GB-D (Deep Vent™, GenBank: AAA67131), *Thermococcus kodakaraensis* KODI (KOD, GenBank: BD175553; *Thermococcus* sp. strain KOD (Pfx, GenBank: AAE68738, BAA06142)), *Thermococcus gorgonarius* (Tgo, Pdb: 4699806), *Sulfolobus solataricus* (GenBank: NC002754, P26811), *Aeropyrum pernix* (GenBank: BAA81109), *Archaeglobus fulgidus* (GenBank: O29753), *Pyrobaculum aerophilum* (GenBank: AAL63952), *Pyrodictium occultum* (GenBank: BAA07579, BAA07580), *Thermococcus* 9 degree Nm (GenBank: AAA88769, Q56366), *Thermococcus fumicolans* (GenBank: CAA93738, P74918), *Thermococcus hydrothermalis* (GenBank: CAC18555), *Thermococcus* spp. GE8 (GenBank: CAC12850), *Thermococcus* spp. JDF-3 (GenBank: AX135456; WO0132887), *Thermococcus* spp. TY (GenBank: CAA73475), *Pyrococcus abyssi* (GenBank: P77916), *Pyrococcus glycovorans* (GenBank: CAC12849), *Pyrococcus horikoshii* (GenBank: NP 143776), *Pyrococcus* spp. GE23 (GenBank: CAA90887), *Pyrococcus* spp. ST700 (GenBank: CAC12847), *Thermococ-*

*cus pacificus* (GenBank: AX411312.1), *Thermococcus zilligii* (GenBank: DQ3366890), *Thermococcus aggregans*, *Thermococcus barossii*, *Thermococcus celer* (GenBank: DD259850.1), *Thermococcus profundus* (GenBank: E14137), *Thermococcus siculi* (GenBank: DD259857.1), *Thermococcus thioreducens*, *Thermococcus onnurineus* NA1, *Sulfolobus acidocaldarium*, *Sulfolobus tokodaii*, *Pyrobaculum calidifontis*, *Pyrobaculum islandicum* (GenBank: AAF27815), *Methanococcus jannaschii* (GenBank: □58295), *Desulforococcus* species TOK, *Desulfurococcus*, *Pyrolobus*, *Pyrodictium*, *Staphylothermus*, *Vulcanisaetta*, *Methanococcus* (GenBank: P52025) and other archaeal B polymerases, such as GenBank AAC62712, P956901, BAAA07579)). Additional representative temperature-stable family A and B polymerases include, e.g., polymerases extracted from the thermophilic bacteria *Thermus* species (e.g., *favus, Huber, thermophilus, lacteus, rubens, aquaticus*), *Bacillus stearothermophilus*, *Thermotoga maritima*, *Methanothermus fervidus*.

Typically, appropriate PCR enzymes from the archaeal family B DNA polymerase group are commercially available, including Pfu (Stratagene), KOD (Toyobo), Pfx (Life Technologies, Inc.), Vent (New England BioLabs), Deep Vent (New England BioLabs), Tgo (Roche), and Pwo (Roche). Suitable DNA polymerases can also be derived from archaea with optimal growth temperatures that are similar to the desired assay temperatures. In some embodiments, suitable archaea exhibit maximal growth temperatures of >80-85° C. or optimal growth temperatures of >70-80° C. Additional archaea related to those listed above are described in the following references: Archaea: A Laboratory Manual (Robb, F. T. and Place, A. R., eds.), Cold Spring Harbor Laboratory Press, Cold Spring Harbor, N.Y., 1995.

DNA polymerases suitable for the present invention include DNA polymerases that have not yet been isolated.

Chimeric DNA Polymerases

In some embodiments, chimeric DNA polymerases suitable for the invention include any DNA polymerases containing sequences derived from two or more different DNA polymerases. In some embodiments, chimeric DNA polymerases suitable for the invention include chimeric DNA polymerases as described in co-pending application entitled "Chimeric DNA polymerases" filed on even date, the disclosures of which are hereby incorporated by reference. In some embodiments, chimeric DNA polymerases suitable for the invention contain sequences derived from Pfu and KOD DNA polymerases. In particular embodiments, a chimeric DNA polymerase suitable for the invention contains an amino acid sequence as shown in SEQ ID NO:16 (the Kofu amino acid sequence shown in the Sequences section). In some embodiments, a chimeric DNA polymerase suitable for the invention contains an amino acid sequence as shown in SEQ ID NO:15 (the Pod amino acid sequence shown in the Sequences section).

Chimeric DNA polymerases suitable for the invention also include the chimeric DNA polymerases described in U.S. Publication Nos. 20020119461, 20040058362 and U.S. Pat. No. 7,560,260, herein incorporated by reference in their entireties.

Fusion DNA Polymerases

Suitable fusion DNA polymerases include any DNA polymerases that are combined (e.g., covalently or non-covalently) with one or more protein domains having a desired activity (e.g., DNA-binding, dUTP hydrolysis or stabilizing template-primer complexes). In some embodiments, the one or more protein domains having the desired activity are derived from a non-polymerase protein. Typically, fusion DNA polymerases are generated to improve certain functional characteristics (e.g., processivity, elongation rate, fidelity, salt-resistance, dUTP tolerance etc.) of a DNA polymerase. For example, DNA polymerase has been fused in frame to the helix-hairpin-helix DNA binding motifs from DNA topoisomerase V and shown to increase processivity, salt resistance and thermostability of the fusion DNA polymerase as described in Pavlov et al., 2002, Proc. Natl. Acad. Sci. USA, 99:13510-13515. Fusion of the thioredoxin binding domain to T7 DNA polymerase enhances the processivity of the DNA polymerase fusion in the presence of thioredoxin as described in WO 97/29209, U.S. Pat. No. 5,972,603 and Bedford et al. Proc. Natl. Acad. Sci. USA 94: 479-484 (1997). Fusion of the archaeal PCNA binding domain to Taq DNA polymerase results in a DNA polymerase fusion that has enhanced processivity and produces higher yields of PCR amplified DNA in the presence, of PCNA (Motz, M., et al., J. Biol. Chem. May 3, 2002; 277 (18); 16179-88). Also, fusion of the sequence non-specific DNA binding protein Sso7d or Sac7d from *Sulfolobus sulfataricus* to a DNA polymerase, such as Pfu or Taq DNA polymerase, was shown to greatly increase the processivity of these DNA polymerases as disclosed in WO 01/92501 A1, which is hereby incorporated by reference in its entirety. Additional fusion polymerases are described in US Publication No. 20070190538A1, which is incorporated herein by reference.

Commercially available exemplary fusion polymerases include, but are not limited to, Phusion™ (Finnzymes and NEB, sold by BioRad as iProof) which is a chimeric Deep Vent™/Pfu DNA polymerase fused to a small basic chromatin-like Sso7d protein (see, U.S. Pat. No. 6,627,424, U.S. Application Publication NOs. 20040191825, 20040081963, 20040002076, 20030162173, 20030148330, and Wang et al. 2004, Nucleic Acids Research, 32(3), 1197-1207, all of which are hereby incorporated by reference); PfuUltra™ II Fusion (Stratagene) which is a Pfu-based DNA polymerase fused to a double stranded DNA binding protein (U.S. Application No. 20070148671, which is incorporated by reference); Herculase II Fusion (Stratagene) which is a Herculase II enzyme fused to a DNA-binding domain; and Pfx50 (Invitrogen) which is a DNA polymerase from *T. zilligii* fused to an accessory protein that stabilizes primer-template complexes.

Generation of Modified DNA Polymerases of the Invention

Modified DNA polymerases can be generated by introducing one or more amino acid alterations into a DNA polymerase at the positions corresponding to the positions described herein (e.g., positions identified in Tables 1, 2, 3, 4, 5 and 6).

Corresponding positions in various DNA polymerases can be determined by alignment of amino acid sequences. Alignment of amino acid sequences can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., *Methods in Enzymology*, 266, 460-480 (1996); http://blast.wustl/edu/blast/README.html). WU-BLAST-2 uses several search parameters, most of which are set to the default values. The adjustable parameters are set with the following values: overlap span=1, overlap fraction=0.125, word threshold (T)=11. HSP score (S) and HSP S2 parameters are dynamic values and are established by the program itself, depending upon the composition of the particular sequence, however, the minimum values may be adjusted and are set as indicated above. An example of an alignment is shown in FIG. 1.

Alterations may be a substitution, deletion or insertion of one or more amino acid residues. Appropriate alteration for each position can be determined by examining the nature and the range of mutations at the corresponding position described herein. In some embodiments, appropriate amino acid alterations can be determined by evaluating a three-dimensional structure of a DNA polymerase of interest (e.g., parental DNA polymerase). For example, amino acid substitutions identical or similar to those described in Tables 1, 2, 3, 4, 5, or 6 can be introduced to a DNA polymerase. Alternative amino acid substitutions can be made using any of the techniques and guidelines for conservative and non-conservative amino acids as set forth, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. As used herein, "non-conservative substitution" refers to the substitution of an amino acid in one class with an amino acid from another class; for example, substitution of an Ala, a class II residue, with a class III residue such as Asp, Asn, Glu, or Gln. Insertions or deletions may optionally be in the range of 1 to 5 amino acids.

Appropriate amino acid alterations allowed in relevant positions may be confirmed by testing the resulting modified DNA polymerases for activity in the in vitro assays known in the art or as described in the Examples below.

The variations can be made using methods known in the art such as oligonucleotide-mediated (site-directed) mutagenesis, and PCR mutagenesis. Site-directed mutagenesis (Carter et al., *Nucl. Acids Res.*, 13:4331 (1986); Zoller et al., Nucl. Acids Res., 10:6487 (1987)), cassette mutagenesis (Wells et al., *Gene,* 34:315 (1985)), restriction selection mutagenesis (Wells et al., Philos. *Trans. R. Soc.* London SerA, 317:415 (1986)), inverse PCR with mutations included in the primer sequence, or other known techniques can be performed on the cloned DNA to produce desired modified DNA polymerases.

In some embodiments, alterations suitable for the invention also include chemical modification including acetylation, acylation, amidation, ADP-ribosylation, glycosylation, GPI anchor formation, covalent attachment of a lipid or lipid derivative, methylation, myristlyation, pegylation, prenylation, phosphorylation, ubiqutination, or any similar process.

Modified DNA polymerases according to the invention may contain one or more amino acid alterations at one or more positions corresponding to those described in Tables 1, 2, 3, 4, 5, or 6. Modified DNA polymerases according to the invention may also contain additional substitutions, insertions and/or deletions independent of the mutations observed or selected in the directed evolution experiments. Thus, in some embodiments, a modified DNA polymerase according to the invention has an amino acid sequence at least 70%, including at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99%, identical to the corresponding wild-type (or naturally-occurring) DNA polymerase.

"Percent (%) amino acid sequence identity" is defined as the percentage of amino acid residues in a modified sequence that are identical with the amino acid residues in the corresponding parental sequence, after aligning the sequences and introducing gaps, if necessary, to achieve the maximum percent sequence identity, and not considering any conservative substitutions as part of the sequence identity. Alignment for purposes of determining percent amino acid sequence identity are similar to the alignment for purposes of determining corresponding positions as described above.

Methods well known in the art may be applied to express and isolate modified DNA polymerases. Many bacterial expression vectors contain sequence elements or combinations of sequence elements allowing high level inducible expression of the protein encoded by a foreign sequence. For example, expression vectors are commercially available from, for example, Novagen (www.emdbiosciences.com/html/NVG/AllTables.html#).

As an example, bacteria expressing an integrated inducible form of the T7 RNA polymerase gene may be transformed with an expression vector bearing a modified DNA polymerase gene linked to the T7 promoter. Induction of the T7 RNA polymerase by addition of an appropriate inducer, for example, isopropyl-p-D-thiogalactopyranoside (IPTG) for a lac-inducible promoter, induces the high level expression of the chimeric gene from the T7 promoter.

Appropriate host strains of bacteria may be selected from those available in the art by one of skill in the art. As a non-limiting example, *E. coli* strain BL-21 is commonly used for expression of exogenous proteins since it is protease deficient relative to other strains of *E. coli*. For situations in which codon usage for the particular polymerase gene differs from that normally seen in *E. coli* genes, there are strains of BL-21 that are modified to carry tRNA genes encoding tRNAs with rarer anticodons (for example, argU, ileY, leuW, and proL tRNA genes), allowing high efficiency expression of cloned chimeric genes (several BL21-CODON PLUSTM cell strains carrying rare-codon tRNAs are available from Stratagene, for example). Additionally or alternatively, genes encoding DNA polymerases may be codon optimized to facilitate expression in *E. coli*. Codon optimized sequences can be chemically synthesized.

There are many methods known to those of skill in the art that are suitable for the purification of a modified DNA polymerase of the invention. For example, the method of Lawyer et al. (1993, PCR Meth. & App. 2: 275) is well suited for the isolation of DNA polymerases expressed in *E. coli*, as it was designed originally for the isolation of Taq polymerase. Alternatively, the method of Kong et al. (1993, J. Biol. Chem. 268: 1965, incorporated herein by reference) may be used, which employs a heat denaturation step to destroy host proteins, and two column purification steps (over DEAE-Sepharose and heparin-Sepharose columns) to isolate highly active and approximately 80% pure DNA polymerase.

Further, modified DNA polymerase may be isolated by an ammonium sulfate fractionation, followed by Q Sepharose and DNA cellulose columns, or by adsorption of contaminants on a HiTrap Q column, followed by gradient elution from a HiTrap heparin column Applications of Modified DNA Polymerases of the Invention Modified DNA polymerases of the present invention may be used for any methods involving polynucleotide synthesis. Polynucleotide synthesis methods are well known to a person of ordinary skill in the art and can be found, for example, in Molecular Cloning second edition, Sambrook et al., Cold Spring Harbor Laboratory Press, Cold Spring Harbor, N.Y. (1989). For example, modified DNA polymerases of the present invention have a variety of uses in recombinant DNA technology including, but not limited to, labeling of DNA by nick translation, second-strand cDNA synthesis in cDNA cloning, DNA sequencing, whole-genome amplification and amplifying, detecting, and/or cloning nucleic acid sequences using polymerase chain reaction (PCR).

In some embodiments, the invention provides enzymes that are better suited for PCR used in industrial or research applications. PCR refers to an in vitro method for amplifying a specific polynucleotide template sequence. The technique of PCR is described in numerous publications, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989). PCR is also described in many U.S. patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, each of which is herein incorporated by reference.

Modified DNA polymerases with higher processivity, elongation rate and/or fidelity are expected to improve efficiency and success rate of long-range amplification (higher yield, longer targets amplified) and reduce the amount of required DNA template.

Various specific PCR amplification applications are available in the art (for reviews, see for example, Erlich, 1999, Rev Immunogenet., 1: 127-34; Prediger 2001, Methods Mol. Biol. 160: 49-63; Jurecic et al., 2000, Curr. Opin. Microbiol. 3: 316-21; Triglia, 2000, Methods Mol. Biol. 130: 79-83; MaClelland et al., 1994, PCR Methods Appl. 4: S66-81; Abramson and Myers, 1993, Current Opinion in Biotechnology 4: 41-47; each of which is incorporated herein by references).

As non-limiting examples, the present invention can be used in PCR applications including, but are not limited to, i) hot-start PCR which reduces non-specific amplification; ii) touch-down PCR which starts at high annealing temperature, then decreases annealing temperature in steps to reduce non-specific PCR product; iii) nested PCR which synthesizes more reliable product using an outer set of primers and an inner set of primers; iv) inverse PCR for amplification of regions flanking a known sequence. In this method, DNA is digested, the desired fragment is circularized by ligation, then PCR using primer complementary to the known sequence extending outwards; v) AP-PCR (arbitrary primed)/RAPD (random amplified polymorphic DNA). These methods create genomic fingerprints from species with little-known target sequences by amplifying using arbitrary oligonucleotides; vi) RT-PCR which uses RNA-directed DNA polymerase (e.g., reverse transcriptase) to synthesize cDNAs which is then used for PCR. This method is extremely sensitive for detecting the expression of a specific sequence in a tissue or cells. It may also be use to quantify mRNA transcripts; vii) RACE (rapid amplification of cDNA ends). This is used where information about DNA/protein sequence is limited. The method amplifies 3' or 5' ends of cDNAs generating fragments of cDNA with only one specific primer each (plus one adaptor primer). Overlapping RACE products can then be combined to produce full length cDNA; viii) DD-PCR (differential display PCR) which is used to identify differentially expressed genes in different tissues. First step in DD-PCR involves RT-PCR, then amplification is performed using short, intentionally nonspecific primers; ix) Multiplex-PCR in which two or more unique targets of DNA sequences in the same specimen are amplified simultaneously. One DNA sequence can be use as control to verify the quality of PCR; x) Q/C-PCR (Quantitative comparative) which uses an internal control DNA sequence (but of different size) which compete with the target DNA (competitive PCR) for the same set of primers; xi) Recusive PCR which is used to synthesize genes. Oligonucleotides used in this method are complementary to stretches of a gene (>80 bases), alternately to the sense and to the antisense strands with ends overlapping (~20 bases); xii) Asymmetric PCR; xiii) In Situ PCR; xiv) Site-directed PCR Mutagenesis; xv) DOP-PCR that uses partially degenerate primers for whole-genome amplificationi; xvi) quantitative PCR using SYBR green or oligonucleotide probes to detect amplification; and xvii) error-prone PCR in which conditions are optimized to give an increased number of mutations in the PCR product.

It should be understood that this invention is not limited to any particular amplification system. As other systems are developed, those systems may benefit by practice of this invention.

Kits

The invention also contemplates kit formats which include a package unit having one or more containers containing modified DNA polymerases of the invention and compositions thereof. In some embodiments, the present invention provides kits further including containers of various reagents used for polynucleotide synthesis, including synthesis in PCR.

Inventive kits in accordance with the present invention may also contain one or more of the following items: polynucleotide precursors, primers, buffers, instructions, and controls. Kits may include containers of reagents mixed together in suitable proportions for performing the methods in accordance with the invention. Reagent containers preferably contain reagents in unit quantities that obviate measuring steps when performing the subject methods.

EXAMPLES

Example 1

Directed Evolution Experiments Using a Chimeric Enzyme Kofu

To select mutated enzymes that would better be suited for recombinant DNA technologies, a directed evolution experiment is designed by simply mimicking the normal conditions under which the enzyme is usually used, or possibly under less than perfect conditions such as are expected in real-life applications. After conducting enough rounds of selection, an enzyme (or multiple enzymes) that is better suited for typical applications in recombinant DNA technologies should appear.

It is contemplated that this approach may be particularly suited to a chimeric enzyme that has been assembled from two different but similar enzymes, such as Kofu (see co-pending application entitled "Chimeric DNA polymerases" filed on even date, the disclosures of which are hereby incorporated by reference). The sequence of Kofu is shown in the Sequences section and in FIG. 1. The regions from KOD and Pfu are indicated in FIG. 1.

In this case, the component parts from different enzymes may not function well together in certain ways because they have evolved separately and been recently and artificially fused. Thus, small changes may be needed to bring the component parts into better conjunction. For example, mutations which bring the parts derived from KOD to more closely resemble the Pfu equivalent part (and vice versa) are likely to be selected for.

We have performed just such a selection on Kofu. In this particular experiment, the region that was mutated was limited to the polymerase domain of the enzyme. The PCR, in which the enrichment step manifests, was performed under near standard PCR conditions, without any hard, deliberately applied specific selective pressure. To varying degrees the reaction was made slightly suboptimal, as follows:

(1) Four different buffers were used; one was a standard PCR buffer, one contained known PCR enhancers, one contained higher than normal levels of the buffering component and the final was a combination of the previous two.

(2) The reaction contained impurities that may often be found in PCRs as they are commonly performed in real applications. The impurities included non-target DNA, RNA, proteins, lipids and other cellular components commonly found in biological samples.

(3) Primers were designed to have a propensity for primer-dimer formation (a common problem in PCR as it is performed in real applications).

(4) In some cases the extension time was marginally longer than required, or marginally shorter than ideal.

Several rounds of selection were conducted. During the course of the ongoing selection, it is likely that many different mutations will confer different types of advantage, to different degrees, either alone or in combination. Typically, during the first rounds of selection, there are no obvious dominant clones, while the huge numbers of neutral or disadvantageous mutants are likely to be eliminated. Thereafter, a large number of particular mutations typically appear in higher than expected numbers. These mutations are there because they have some advantages.

Typically, the selections are considered to have worked when the vast pool of mutants that are in the starting material have been eliminated and the pool is dominated by a remaining few types or families of mutants that have out-competed the other mutants and the wild type. At this stage, it is not necessary to define exactly the nature of the improvement that the mutations confer. The fact that it was selected for is sufficient proof, especially if the same mutation becomes dominant in independently run selections.

Further selection results in the number of some of these mutations increasing in the pool, while others may be eliminated possibly because they have some advantages but they are not sufficient enough to compete with better-adapted clones. At the same time, some previously unnoticed mutants may appear. The late appearance of these mutants might be due to the fact that these specific mutations were low in number in the starting pool, or that the mutation required another (or more than one) mutation in the same clone for the advantage to manifest. If selections continue even further, eventually, a few clones will likely to dominate substantially. Typically, it is important to isolate clones before this final point if it is desirable to isolate a wide range of beneficial mutations.

Example 2

Mutations Observed

Several rounds of selection were conducted as described in Example 1. During the course of the ongoing selections, many different mutations were observed either alone or in combination. Enzymes containing one or more of these mutations retain the enzymatic activity. Active enzymes with as many as 14 mutations were observed. An example is the highly active clone 5/7-F5 comprising the following mutations: E377K, L400P, N434S, K444M, P454S, A504V, C510S, F591I, V640I, K648R, V665M, I697F, E734N and L742M. The mutations observed in all the clones that were sequenced are shown in Table 1.

TABLE 1

MUTATIONS OBSERVED

| Position | Mutation |
|---|---|
| 342 | Q342L |
| 343 | P343A |
| 343 | P343R |
| 343 | P343S |
| 344 | L344P |
| 344 | L344Q |
| 345 | W345R |
| 346 | D346E |
| 346 | D346G |
| 346 | D346N |
| 346 | D346V |
| 347 | V347A |
| 347 | V347I |
| 348 | S348L |
| 348 | S348T |
| 349 | R349H |
| 350 | S350T |
| 351 | S351L |
| 352 | T352I |
| 352 | T352N |
| 354 | N354I |
| 354 | N354K |
| 354 | N354S |
| 354 | N354Y |
| 355 | L355F |
| 355 | L355I |
| 355 | L355V |
| 356 | V356A |
| 356 | V356L |
| 356 | V356M |
| 357 | E357G |
| 358 | W358R |
| 361 | L361M |
| 361 | L361V |
| 362 | R362G |
| 362 | R362K |
| 363 | K363R |
| 365 | Y365C |
| 365 | Y365F |
| 365 | Y365H |
| 366 | E366A |
| 367 | R367L |
| 368 | N368D |
| 368 | N368S |
| 368 | N368Y |
| 369 | E369D |
| 369 | E369V |
| 370 | V370A |
| 370 | V370I |
| 370 | V370L |
| 371 | A371T |
| 371 | A371V |
| 372 | P372L |
| 373 | N373S |
| 374 | K374R |
| 375 | P375L |
| 376 | S376G |
| 376 | S376N |
| 376 | S376R |
| 376 | S376T |
| 377 | E377D |
| 377 | E377G |
| 377 | E377K |
| 377 | E377R |
| 377 | E377V |
| 378 | E378D |
| 378 | E378G |
| 378 | E378K |
| 378 | E378V |
| 379 | E379K |
| 379 | E379V |
| 381 | Q381K |
| 381 | Q381R |
| 382 | R382H |
| 382 | R382L |
| 384 | L384H |

TABLE 1-continued

MUTATIONS OBSERVED

| Position | Mutation |
|---|---|
| 384 | L384R |
| 384 | L384V |
| 385 | R385H |
| 386 | E386G |
| 386 | E386K |
| 386 | E386V |
| 387 | S387T |
| 389 | T389I |
| 389 | T389S |
| 392 | F392Y |
| 394 | K394M |
| 395 | E395D |
| 395 | E395K |
| 396 | P396S |
| 397 | E397D |
| 397 | E397N |
| 397 | E397V |
| 397 | E397W |
| 398 | K398R |
| 400 | L400F |
| 400 | L400H |
| 400 | L400P |
| 400 | L400Y |
| 402 | E402G |
| 403 | N403K |
| 404 | I404V |
| 410 | R410H |
| 410 | R410L |
| 414 | P414S |
| 415 | S415T |
| 416 | I416T |
| 416 | I416V |
| 422 | V422I |
| 424 | P424L |
| 424 | P424S |
| 425 | D425G |
| 425 | D425N |
| 426 | T426M |
| 427 | L427F |
| 427 | L427P |
| 427 | L427R |
| 428 | N428D |
| 428 | N428S |
| 428 | N428Y |
| 429 | L429F |
| 429 | L429S |
| 429 | L429V |
| 429 | L429W |
| 430 | E430A |
| 430 | E430D |
| 430 | E430G |
| 431 | G431C |
| 432 | C432Y |
| 433 | K433E |
| 434 | N434D |
| 434 | N434I |
| 434 | N434K |
| 434 | N434S |
| 434 | N434Y |
| 436 | D436V |
| 437 | I437N |
| 437 | I437V |
| 438 | A438D |
| 438 | A438T |
| 438 | A438V |
| 439 | P439L |
| 439 | P439S |
| 440 | Q440H |
| 440 | Q440L |
| 440 | Q440R |
| 441 | V441I |
| 442 | G442E |
| 443 | H443D |
| 443 | H443R |
| 443 | H443Y |
| 444 | K444M |
| 444 | K444N |
| 444 | K444R |
| 445 | F445C |
| 445 | F445I |
| 445 | F445V |
| 445 | F445Y |
| 447 | K447E |
| 447 | K447N |
| 447 | K447R |
| 448 | D448Y |
| 449 | I449N |
| 449 | I449T |
| 449 | I449V |
| 450 | P450L |
| 451 | G451S |
| 452 | F452L |
| 453 | I453T |
| 453 | I453V |
| 454 | P454A |
| 454 | P454S |
| 455 | S455F |
| 455 | S455T |
| 455 | S455Y |
| 456 | L456M |
| 456 | L456V |
| 458 | G458A |
| 458 | G458D |
| 458 | G458S |
| 458 | G458V |
| 459 | H459N |
| 459 | H459Q |
| 459 | H459Y |
| 460 | L460S |
| 461 | L461P |
| 461 | L461Q |
| 462 | E462D |
| 462 | E462K |
| 464 | R464H |
| 465 | Q465H |
| 465 | Q465R |
| 466 | K466I |
| 466 | K466N |
| 467 | I467F |
| 467 | I467N |
| 469 | T469A |
| 469 | T469I |
| 470 | K470I |
| 470 | K470N |
| 470 | K470R |
| 471 | M471L |
| 471 | M471T |
| 472 | K472N |
| 472 | K472R |
| 473 | E473G |
| 474 | T474I |
| 474 | T474N |
| 474 | T474P |
| 474 | T474S |
| 475 | Q475H |
| 475 | Q475L |
| 475 | Q475R |
| 476 | D476E |
| 476 | D476G |
| 476 | D476N |
| 477 | P477H |
| 477 | P477L |
| 477 | P477S |
| 477 | P477T |
| 478 | I478F |
| 478 | I478L |
| 478 | I478N |
| 478 | I478T |
| 479 | E479D |
| 479 | E479K |
| 479 | E479V |
| 480 | K480E |

TABLE 1-continued

MUTATIONS OBSERVED

| Position | Mutation |
|---|---|
| 480 | K480M |
| 480 | K480T |
| 481 | I481F |
| 481 | I481L |
| 481 | I481N |
| 481 | I481T |
| 481 | I481V |
| 483 | L483F |
| 483 | L483H |
| 484 | D484E |
| 486 | R486L |
| 488 | K488I |
| 488 | K488N |
| 488 | K488R |
| 489 | A489P |
| 492 | L492S |
| 493 | L493I |
| 494 | A494S |
| 494 | A494T |
| 494 | A494V |
| 494 | A494V |
| 496 | S496P |
| 496 | S496T |
| 497 | F497Y |
| 501 | Y501C |
| 501 | Y501F |
| 504 | A504K |
| 504 | A504T |
| 504 | A504V |
| 505 | K505R |
| 509 | Y509C |
| 509 | Y509H |
| 510 | C510R |
| 510 | C510S |
| 510 | C510Y |
| 511 | K511N |
| 512 | E512D |
| 512 | E512G |
| 512 | E512K |
| 512 | E512Q |
| 512 | E512V |
| 516 | S516G |
| 517 | V517A |
| 518 | T518A |
| 518 | T518I |
| 518 | T518S |
| 519 | A519S |
| 519 | A519T |
| 519 | A519V |
| 522 | R522H |
| 524 | Y524H |
| 525 | I525M |
| 526 | E526V |
| 527 | L527S |
| 528 | V528A |
| 529 | W529R |
| 530 | K530G |
| 530 | K530M |
| 530 | K530N |
| 530 | K530R |
| 531 | E531K |
| 532 | L532Q |
| 534 | E534Q |
| 534 | E534V |
| 535 | K535I |
| 536 | F536L |
| 536 | F536S |
| 536 | F536Y |
| 537 | G537E |
| 537 | G537R |
| 538 | F538Y |
| 539 | K539I |
| 539 | K539R |
| 540 | V540L |
| 541 | L541I |
| 541 | L541P |
| 550 | A550V |
| 551 | T551I |
| 552 | I552T |
| 552 | I552V |
| 553 | P553H |
| 553 | P553L |
| 554 | G554D |
| 555 | G555R |
| 555 | G555W |
| 556 | E556D |
| 556 | E556K |
| 556 | E556Q |
| 556 | E556V |
| 557 | S557P |
| 558 | E558G |
| 558 | E558K |
| 558 | E558Q |
| 559 | E559D |
| 560 | I560L |
| 560 | I560T |
| 560 | I560V |
| 561 | K561E |
| 561 | K561M |
| 561 | K561R |
| 562 | K562I |
| 562 | K562R |
| 563 | K563E |
| 563 | K563I |
| 563 | K563N |
| 563 | K563R |
| 563 | K563T |
| 564 | A564T |
| 564 | A564V |
| 565 | L565M |
| 566 | E566D |
| 566 | E566G |
| 567 | F567I |
| 567 | F567S |
| 567 | F567Y |
| 568 | L568F |
| 568 | L568I |
| 569 | K569E |
| 569 | K569N |
| 569 | K569R |
| 570 | Y570F |
| 570 | Y570H |
| 571 | I571M |
| 571 | I571V |
| 573 | A573D |
| 573 | A573S |
| 573 | A573T |
| 573 | A573V |
| 574 | K574N |
| 576 | P576L |
| 577 | G577D |
| 578 | A578S |
| 578 | A578T |
| 578 | A578V |
| 579 | L579M |
| 579 | L579P |
| 579 | L579Q |
| 580 | E580G |
| 580 | E580K |
| 582 | E582D |
| 582 | E582G |
| 582 | E582K |
| 582 | E582V |
| 584 | E584K |
| 585 | G585R |
| 586 | F586L |
| 588 | K588E |
| 588 | K588R |
| 589 | R589C |
| 591 | F591I |
| 591 | F591L |
| 591 | F591Y |

TABLE 1-continued

MUTATIONS OBSERVED

| Position | Mutation |
|---|---|
| 592 | F592L |
| 592 | F592S |
| 592 | F592Y |
| 593 | V593A |
| 593 | V593L |
| 594 | T594A |
| 594 | T594S |
| 595 | K595R |
| 597 | K597R |
| 599 | A599T |
| 599 | A599V |
| 600 | V600A |
| 600 | V600L |
| 601 | I601F |
| 602 | D602N |
| 604 | E604D |
| 605 | G605D |
| 605 | G605S |
| 606 | K606E |
| 606 | K606N |
| 606 | K606R |
| 608 | T608A |
| 608 | T608K |
| 608 | T608M |
| 609 | T609A |
| 609 | T609I |
| 609 | T609S |
| 610 | R610K |
| 614 | I614M |
| 614 | I614S |
| 614 | I614T |
| 614 | I614V |
| 615 | V615A |
| 615 | V615I |
| 617 | R617G |
| 619 | W619R |
| 620 | S620G |
| 620 | S620N |
| 621 | E621D |
| 621 | E621G |
| 621 | E621V |
| 622 | I622F |
| 622 | I622V |
| 623 | A623T |
| 623 | A623V |
| 625 | E625D |
| 626 | T626A |
| 626 | T626S |
| 628 | A628T |
| 628 | A628V |
| 629 | R629H |
| 629 | R629S |
| 630 | V630A |
| 630 | V630I |
| 630 | V630L |
| 631 | L631S |
| 632 | E632G |
| 632 | E632V |
| 633 | A633T |
| 633 | A633V |
| 634 | L634V |
| 635 | L635M |
| 635 | L635P |
| 636 | K636I |
| 636 | K636R |
| 637 | D637G |
| 638 | G638E |
| 638 | G638R |
| 638 | G638V |
| 638 | G638W |
| 640 | V640A |
| 640 | V640D |
| 640 | V640F |
| 640 | V640I |
| 641 | E641G |
| 641 | E641K |
| 642 | K642E |
| 642 | K642M |
| 642 | K642N |
| 642 | K642R |
| 643 | A643T |
| 643 | A643V |
| 644 | V644A |
| 644 | V644L |
| 644 | V644M |
| 645 | R645L |
| 645 | R645P |
| 645 | R645Q |
| 646 | I646F |
| 646 | I646T |
| 646 | I646V |
| 647 | V647A |
| 647 | V647I |
| 648 | K648E |
| 648 | K648R |
| 648 | K648T |
| 650 | V650A |
| 651 | T651A |
| 651 | T651N |
| 652 | E652D |
| 652 | E652G |
| 652 | E652K |
| 652 | E652V |
| 653 | K653I |
| 653 | K653R |
| 655 | S655F |
| 656 | K656M |
| 657 | Y657C |
| 658 | E658G |
| 658 | E658K |
| 659 | V659I |
| 660 | P660L |
| 660 | P660Q |
| 660 | P660S |
| 660 | P660T |
| 661 | P661H |
| 661 | P661L |
| 662 | E662G |
| 662 | E662K |
| 662 | E662V |
| 665 | V665A |
| 665 | V665M |
| 666 | I666L |
| 666 | I666M |
| 667 | H667D |
| 667 | H667Y |
| 668 | E668G |
| 668 | E668K |
| 668 | E668V |
| 669 | Q669R |
| 670 | I670V |
| 672 | R672C |
| 672 | R672H |
| 673 | D673E |
| 675 | K675R |
| 676 | D676A |
| 676 | D676N |
| 678 | K678M |
| 678 | K678R |
| 678 | K678T |
| 679 | A679T |
| 679 | A679V |
| 680 | T680I |
| 680 | T680K |
| 680 | T680R |
| 681 | G681D |
| 681 | G681S |
| 684 | V684I |
| 685 | A685T |
| 688 | K688R |
| 689 | R689K |
| 691 | A691T |

TABLE 1-continued

MUTATIONS OBSERVED

| Position | Mutation |
|---|---|
| 691 | A691V |
| 692 | A692V |
| 693 | R693Q |
| 693 | R693W |
| 694 | G694D |
| 695 | V695A |
| 695 | V695D |
| 695 | V695G |
| 695 | V695I |
| 695 | V695L |
| 696 | K696E |
| 697 | I697F |
| 698 | R698H |
| 698 | R698P |
| 701 | T701A |
| 701 | T701S |
| 702 | V702M |
| 703 | I703M |
| 703 | I703T |
| 704 | S704G |
| 704 | S704N |
| 706 | I706T |
| 706 | I706V |
| 707 | V707I |
| 708 | L708S |
| 709 | K709E |
| 709 | K709M |
| 709 | K709N |
| 709 | K709Q |
| 709 | K709R |
| 710 | G710C |
| 711 | S711P |
| 711 | S711T |
| 714 | I714T |
| 715 | G715R |
| 715 | G715W |
| 716 | D716E |
| 716 | D716G |
| 719 | I719V |
| 720 | P720H |
| 720 | P720S |
| 721 | F721S |
| 721 | F721Y |
| 722 | D722G |
| 723 | E723D |
| 723 | E723V |
| 724 | F724Y |
| 725 | D725E |
| 725 | D725G |
| 725 | D725V |
| 726 | P726A |
| 726 | P726S |
| 726 | P726T |
| 727 | T727A |
| 727 | T727I |
| 727 | T727N |
| 728 | K728I |
| 728 | K728N |
| 728 | K728R |
| 729 | H729D |
| 729 | H729N |
| 730 | K730E |
| 730 | K730I |
| 730 | K730Q |
| 731 | Y731C |
| 732 | D732E |
| 732 | D732G |
| 733 | A733S |
| 733 | A733V |
| 734 | E734D |
| 734 | E734G |
| 734 | E734K |
| 734 | E734N |
| 735 | Y735F |
| 737 | I737N |
| 737 | I737T |

TABLE 1-continued

MUTATIONS OBSERVED

| Position | Mutation |
|---|---|
| 738 | E738D |
| 738 | E738G |
| 738 | E738K |
| 739 | N739H |
| 739 | N739K |
| 740 | Q740R |
| 741 | V741A |
| 742 | L742M |
| 743 | P743A |
| 743 | P743R |
| 743 | P743S |
| 743 | P743T |
| 744 | A744T |
| 744 | A744V |
| 745 | V745A |
| 745 | V745I |
| 746 | E746D |
| 746 | E746G |
| 746 | E746K |
| 746 | E746V |
| 748 | I748L |
| 748 | I748M |
| 750 | R750H |
| 751 | A751T |
| 751 | A751V |
| 752 | F752L |
| 752 | F752S |
| 752 | F752V |
| 752 | F752Y |
| 754 | Y754F |
| 754 | Y754H |
| 756 | K756E |
| 757 | E757D |
| 757 | E757G |
| 758 | D758G |
| 758 | D758N |
| 758 | D758Y |
| 759 | L759P |
| 760 | R760C |
| 760 | R760H |
| 761 | Y761C |
| 761 | Y761H |
| 761 | Y761N |
| 762 | Q762H |
| 762 | Q762L |
| 762 | Q762R |
| 763 | K763I |
| 763 | K763N |
| 764 | T764I |
| 765 | R765I |
| 766 | Q766R |
| 767 | V767A |
| 767 | V767L |
| 768 | G768D |
| 768 | G768R |
| 768 | G768S |
| 769 | L769M |
| 769 | L769P |
| 769 | L769R |
| 770 | S770P |
| 770 | S770Y |
| 771 | A771S |
| 771 | A771T |
| 772 | W772L |
| 772 | W772R |
| 773 | L773F |
| 773 | L773P |
| 777 | G777E |
| 567 | F567I |
| 567 | F567S |
| 567 | F567Y |
| 568 | L568F |

Example 3

Types of Selective Advantage

There are a wide range of advantages that may have been selected for, some of which are listed and discussed below:

1) Expression Efficiency:

The clones that express higher levels of the enzyme will have an advantage over those that express less. The specific activity of the mutated enzyme may not have been improved but the total activity will have. This characteristics is particularly valuable to a manufacture of enzymes because this will allow increased production levels and/or reduced production costs.

2) Solubility and Folding Robustness:

When solubility increases, the probability of inclusion bodies forming decreases. Therefore, in these clones, a higher proportion of useful, correctly folded enzyme product is expressed.

3) Thermostability:

It is well known that, during the thermocycling required for PCR, a certain fraction of the enzyme is inactivated due to the heating. An enzyme that is resistant to heat-inactivation will maintain activity longer. Therefore, less enzyme can be used and/or more cycles can be conducted.

4) Activity:

Mutants with increased enzymatic activity provide more efficient polymerization.

5) Processivity:

Mutants with increased processivity are able to synthesize long PCR products. Mutant enzymes that can incorporate more nucleotides/extension step are likely to operate efficiently at lower concentrations.

6) Speed:

Mutants with increased elongation rate provide more efficient polymerization. Enzymes that are fast can also be used with shorter extension times. This is particularly valuable for a high-throughput system.

7) Concentration Robustness:

It is known that PCR reactions may not be carried out appropriately if too much or too little enzyme is used. Under the selection conditions we used, a polymerase that can generate appropriate products whether it is supplied in excess or at low levels will have an advantage and be selected for.

8) Resistance to Salts, PCR Additives and Other Impurities:

The selection was conducted in the presence of salts, PCR additives (e.g., intercalating dyes), and other impurities. The presence of slats may reduce the DNA binding affitnity of polymerases. The presence of impurities may interfere with formation of a desired PCR product. A polymerase that can resist to salts and impurities and synthesize desired products is advantageous and will be selected for. The characteristic is particularly suited for applications in which PCR is used in crude samples.

9) Fidelity:

All polymerases make mistakes during replication, either by incorporating the wrong dNTP or by stuttering which causes deletions and insertions. Such mistakes can eliminate functional genes during selection, so there is a pressure for mistakes not to be made. A polymerase with higher fidelity is advantageous and will be selected for.

10) Avoidance of Primer-Dimers:

As the selection PCR had a built-in propensity to produce primer-dimers, which compete with and so reduce the correct product, there is a selective pressure for polymerases that avoid primer-dimer formation. Polymerases that avoid primer-dimer formation are particularly valuable as primer-dimers are a common problem in PCR.

11) Strand-Displacement Activity:

Secondary structure in the DNA due to intramolecular self annealing may inhibit DNA strand-elongation catalyzed by the polymerase. Similarly, partial re-annealing of the complementary DNA in addition to the primer will inhibit PCR. Any enzyme with improved strand-displacement activity will have an advantage in the selection.

12) Knock-Out of Uracil Read-Ahead Function:

Type B polymerases have a read-ahead domain in the N-terminus that stalls the polymerase upon encountering a uracil residue in the template strand. Mutations that impede stalling at uracil residues may improve PCR efficiency and may therefore be selected for.

13) Increased Nucleotide Selectivity:

dUTP is formed during PCR as the deamination product of dCTP. As discussed above, incorporation of this nucleotide inhibits PCR. Any mutation that improves the selectivity for incorporating canonical nucleotides (dATP, dCTP, dGTP and dTTP) vs. modified nucleotides (e.g., dUTP), may improve PCR efficiency.

14) Pyrophosphate Tolerance:

Pyrophosphate is released during incorporation of nucleotides into the nascent strand by polymerases. Accumulation of pyrophosphate may lead to inhibition of the polymerase activity. Polymerases that were selected for in the Directed evolution example may have evolved to become less affected by product inhibition.

15) Unknown:

There many other factors involved in the process of PCR. Enzymes that are better adapted to PCR for any reason will be selected under our selection conditions.

Example 4

Mutations that were Selected for

The success of the selection were demonstrated if it was shown that (1) a variety of mutations have been selected for; (2) that these relatively few mutations have come to heavily dominate the pool; (3) that mutations appeared both singly and in combination; (4) that a final, dominating family was starting to appear; (5) that mutants displayed a variety of phenotypes; (6) that different profiles of mutants were selected with the different libraries; (7) that some mutations bring the KOD sections to more closely resemble the Pfu equivalent region, and vice versa; and/or (8) that at least some mutants have phenotypic characteristics that were predicted.

Exemplary mutations that were selected for are shown in Table 2. These mutations occurred at least once for every 40 clones sequenced (2.5%). Some mutations occurred in as many as 15% of the sequenced clones. All these mutations give the polymerase some kind of advantage in the selection. The list is prioritized. Highest priority is given to positions where mutations occur most frequently.

TABLE 2

| Mutations that were selected for. | |
|---|---|
| 1) | F752Y |
| 2) | F591L |
| 3) | F591I |
| 4) | E668V |
| 5) | G638R |
| 6) | G638V |
| 7) | E734K |

TABLE 2-continued

Mutations that were selected for.

| | |
|---|---|
| 8) | E377K |
| 9) | T609I |
| 10) | T609A |
| 11) | P454S |
| 12) | E582K |
| 13) | G715R |
| 14) | E580K |
| 15) | A691V |
| 16) | E738G |
| 17) | A494V |
| 18) | K530R |
| 19) | A550V |
| 20) | E512K |
| 21) | V615I |
| 22) | V647A |
| 23) | E652K |
| 24) | V356M |
| 25) | D346G |
| 26) | S376G |
| 27) | Q381R |
| 28) | E386K |
| 29) | R410H |
| 30) | V441I |
| 31) | K444R |
| 32) | E462K |
| 33) | T518A |
| 34) | G555R |
| 35) | K588R |
| 36) | R589C |
| 37) | K597R |
| 38) | K606E |
| 39) | K606N |
| 40) | A633V |
| 41) | A679T |
| 42) | T680I |
| 43) | K688R |
| 44) | A733V |
| 45) | A744V |
| 46) | E746G |
| 47) | A751T |
| 48) | A751V |
| 49) | Q766R |
| 50) | W772R |

Example 5

Mutant Phenotypes

Phenotypes of the selected mutants are closely related to the selective advantages described above. We have identified or expect to identify mutant polymerases that express well, are more soluble, that display higher activity, fidelity, processivity and/or speed, that are active over a wide range of concentrations, that are resistant to impurities, that work over a range of concentrations and/or have a higher fidelity. In addition, some mutant polymerases may have phenotypes that are not immediately measurable. Since many of these phenotypes may depend on the manner in which the DNA and polymerase interact, it is contemplated that the selected mutations may affect DNA-polymerase binding characteristics.

While the phenotypes of the mutants will usually be related to the advantages listed above, other phenotypes may be present. These phenotypes may confer no advantage, but merely be a side effect of the advantageous mutation. In addition some mutants may display phenotypes that could be considered disadvantageous. This is possible if the mutation confers an advantage (for example, high activity) but this comes at a cost (for example, high error-rate or lower DNA binding affinity). If the advantage outweighs the disadvantage, the mutation will still be selected for. Such mutations may have commercial uses, for example a low fidelity enzyme could be used in error-prone PCR (e.g., for mutagenesis). A polymerase with lower DNA-binding affinity may be useful in applications in which processive DNA synthesis is not required. An example of this is sequencing-by-synthesis where a single nucleotide is incorporated per cycle. The utility of an enzyme with lower DNA-binding affinity in sequencing is exemplified in US2006/0281109, which is incorporated herein by reference.

To demonstrate that a variety of phenotypes have been selected for, various clones were subjected to a number of phenotype tests. So far, we have conducted tests for a few different phenotypes: enzyme activity, binding affinity to DNA and fidelity. Exemplary mutations associated with these phenotypes are shown in Tables 3, 4, 5 and 6. Each list is prioritized. Priority rating is based on: strength of phenotype, the frequency with which this mutation occurs in the library pool after selection, and the confidence with which we can assign a phenotype.

TABLE 3

Mutations that increase enzyme activity

| Priority Ranking | Mutations |
|---|---|
| 1. | F752Y |
| 2. | F591L |
| 3. | F591I |
| 4. | G638V |
| 5. | G638R |
| 6. | E668V |
| 7. | E734K |
| 8. | V356M |
| 9. | E738G |
| 10. | E386K |
| 11. | W772R |
| 12. | E377K |

TABLE 4

Mutations that increase binding to DNA

| Priority Ranking | Mutations |
|---|---|
| 1. | F591I |
| 2. | F591L |
| 3. | A550V |
| 4. | E377K |
| 5. | A494V |
| 6. | E734K |
| 7. | G638V |
| 8. | G638R |
| 9. | E668V |
| 10. | D346G |
| 11. | V356M |
| 12. | E738G |

TABLE 5

Mutations that decrease binding to DNA

| Priority Ranking | Mutations |
|---|---|
| 1. | R410H |
| 2. | E582K |
| 3. | E652K |
| 4. | A679T |
| 5. | S376G |
| 6. | T680I |

TABLE 6

Mutations that decrease fidelity

| Priority Ranking | Mutations |
|---|---|
| 1. | F591L |
| 2. | F752Y |
| 3. | F591I |
| 4. | E668V |
| 5. | V441I |
| 6. | G638R |
| 7. | S376G |
| 8. | T680I |

Some mutations that were selected for usually occurred together with other mutations that were also selected for. One such example is R410H. This mutation occurs together with mutations that increase the DNA-binding affinity. Clones 11/5Hi-E3 and 5/7-A6 both contain the mutation R410H and each contains an additional mutation, F591L and A550V respectively, that increases the DNA-binding affinity. The presence of the R410H mutation reduces the DNA-binding affinity relative to clones that contain F591L or A550V but do not have the R410H mutation.

A similar approach was used to identify phenotypes for all the mutations shown in Tables 3-6. Examples of mutations in mutant clones obtained through directed evolution and associated phenotypes are shown in Table 7.

TABLE 7

Mutations in exemplary mutant clones and associated exemplary phenotypes

| Clone | M13 activity Rel. to Kofu | PCR activity Rel. to Kofu | Fidelity $10 \times 10^{-6}$ | Binding affinity mS/cm | Mutations Selected for | Mutations Other (not selected for) |
|---|---|---|---|---|---|---|
| Kofu | 1 | 1 | 1.5 | 37 | n/a | n/a |
| 6/7-D5 | 7x | 2x | 41 | 40.7 | F591L | L400H, G458V, I706V |
| 10/7-D4 | 7x | 2x | 64 | 39.3 | F591L | K447E, K563T, K606E, E621G |
| 11/5Hi-E5 | 4x | 6x | 12 | 40.8 | F591L | F445I, K561E, K653R, |
| 5/7-C4 | 1 | 2x | 4.8 | 41.9 | E377K | A633T |
| 11/5Hi-E3 | 3x | 3x | 3.7 | 38 | R410H, F591L | E580G, K588R, K597R, A679V, R693Q, D725E |
| 5/7-A6 | 3x | 1 | 7.6 | 33.8 | R410H, A550V | P450L, K480M, K505R, K562R, P743T, V767A |
| 5/7-H2 | 3x | 1 | 7 | 40.3 | A550V | L427F, H459Q, K539R, V600A, I601F, F721S, T7 |

Example 6

Specific Examples of Phenotypes and Genotypes

The phenotypes associated with a particular mutation was assessed by expressing and purifying 49 clones. The binding affinity, enzyme activity and fidelity of each clone was determined as indicated in Examples 7-10 and compared to that of Kofu.

Specific examples of clones with altered phenotype compared to Kofu are shown in Table 7. Clones 6/7-D5, 10/7-D4 and 11/5Hi-E5 all contain the mutation F591L, in addition to other mutations. Sequencing of approximately 200 clones showed that the F591L mutation occurred in 15% of the clones. Thus, it is likely that this mutation gives the enzyme a selective advantage in the directed evolution experiment. The clones containing the F591L mutation are characterized by eluting from the heparin column at a higher salt concentration than Kofu, suggesting that they have high binding affinity for DNA. These clones also have higher activity than Kofu as measured both by the M13 activity assay and enzyme dilutions in PCR (see Examples 9 and 10). Furthermore, these clones have lower fidelity than Kofu. The other mutations that occur in these clones are not selected for, suggesting that they may not confer an advantage to the enzyme. These data indicate that the F591L mutation in Kofu increases the DNA-binding affinity, increases the enzyme activity, and decreases the fidelity of the enzyme.

Another example of a mutation that increases DNA-binding affinity is E377K. Clone 5/7-C4 contains only one other mutation and this mutation is not selected for, suggesting that the E377K is likely to be responsible for this phenotype.

Example 7

Fidelity Assay

The fidelity of enzymes was determined by a method similar to that described by Cline et al. and references therein (*Nucl. Acids Res.*, 1996, 24(18): 3546-3551). LacI was PCR amplified from *E. coli* and cloned into pUC19 to generate plasmid pKB-LacIQZalpha (SEQ ID NO:17). pKB-LacIQZalpha served both as template for PCR amplification of LacI in the fidelity assays and as vector for cloning the amplified LacI into for blue/white colony screening.

Specifically, 3×50 μl PCR reactions (for each enzyme) were set-up, using 2.4 ng of pKB-LacIQZalfa plasmid template (equivalent to 1 ng of lacI target), using varying amounts of each enzyme, to amplify the 1.386 Kb lacIQZalpha fragment. The amount of enzyme of each mutant to use in the fidelity assay was determined in an initial PCR using 2-fold dilutions of enzyme. The lowest concentrations of enzyme that gave specific PCR product in a sufficient yield for cloning were chosen for the fidelity assay (see Example 10). The PCR conditions for the fidelity assay were as follows: final concentrations of 1× KapaHifi Fidelity buffer, 2 mM $MgCl_2$, 0.3 μM each of primers M13-40 (GTTTTCCCAGTCACGAC (SEQ ID NO:24)) and PKBlac-1R (GGTATCTTTATAGTC-CTGTCG (SEQ ID NO:25)) and 0.3 mM each dNTP. Cycling parameters were: 95° C. 2 minutes, 25×(98° C. 25 seconds, 55° C. 15 seconds, 68° C. 1 minute), 68° C. 2 minutes.

PCR product yields were quantitated by means of gel electrophoresis and the numbers of template doublings were calculated. PCR products were digested with XbaI, NcoI and DpnI, gel-purified (without exposure to UV light) and ligated into XbaI-NcoI-digested pKB-LacIQZalpha. *E. coli* was transformed with the ligation mixtures and the cells were plated onto LB-Amp-X-gal plates. The number of blue colonies, white colonies and total number of colonies were recorded. The error rate f was calculated as f=−ln(F)/(d× (bp)), where F=fraction of white colonies ((total colonies minus blue colonies)/total colonies), d=number of template doublings and b=349 (only 349 bp of the lacI amplicon are scored).

The fidelities of Kofu and Kofu mutants ranged between 1.3 to 64×10$^{-6}$ (see Table 7).

Example 8

DNA Binding Affinity of Kofu and Kofu Mutants

DNA binding affinity was measured based on heparin binding assays. Heparin is a naturally occurring sulphated glucosaminoglycan. Heparin consists of alternating units of various uronic acid residues and various D-glucosamine with most of these substituted with one or two sulphate groups. The three dimensional structure resembles a single helix. At physiological pH the sulphate groups are deprotonated. The negative charge and the helical structure mimic the structure and charge of DNA, enabling binding of DNA-binding proteins to heparin. DNA polymerases contain a number of positively charged amino acid residues that are involved in binding of the enzyme to DNA. This property can be utilized during purification of polymerases whereby the polymerase binds to heparin that is covalently coupled to agarose beads. The binding affinity of the polymerase is determined by the number and strength of binding interactions. The polymerase is eluted by increasing the amount of salt in the elution buffer. Ion-bonds between the polymerase and heparin will be disrupted by adding an increasing concentration of salt. The salt concentration at which the enzyme elutes is, therefore, indicative of the binding affinity of the polymerase for heparin and DNA.

Pellets of *E. coli* cells containing Kofu or mutants thereof were lysed in 50 mM Tris-HCl pH 8.0, 150 mM NaCl (binding buffer). The lysates were incubated for 30 min at 75° C. to denature *E. coli* proteins, followed by centrifugation at 20 000 g for 20 min at 20° C. The supernatant was loaded onto a HiTrap Heparin column (GE Healthcare) and eluted on a 0.15 to 2 M NaCl gradient. The conductivity (mS/cm) at the elution peak was recorded as a measure of salt concentration of the eluate. A high conductivity indicates high affinity of the polymerase for heparin and DNA. The conductivity at the elution peak of Kofu was 37-38 mS/cm. The conductivity for low affinity polymerase mutants was between 34 and 37 mS/cm. The conductivity of high affinity polymerase mutants was between 38 and 51 mS/cm.

The conductivity is proportional to the amount of salt in a solution. We empirically determined the correlation between salt concentration and conductivity. We used the binding buffer and elution buffer at various ratios (final concentrations of 200 to 700 mM NaCl) and measured the conductivity. We plotted the conductivity vs. NaCl concentration. Linear regression analysis revealed that the conductivity (Cd) can be expressed as Cd=0.084×Cs+7.26, (R2=0.9995), where Cs is concentration of NaCl. From this we calculated that Kofu eluted at around 360 mM NaCl, and the mutants eluted at between around 320 and 520 mM NaCl.

Example 9

M13 Enzyme Activity Assay

Enzyme activity of Kofu and mutants of Kofu was measured either by M13 activity assay or by PCR using dilutions of enzyme. In the M13 activity assay, primed ssDNA was extended in an isothermal reaction using a range of dilutions of enzyme, and dsDNA was detected with SYBR green.

The following reactions were set up on ice: 50, 25, 12.5, 6.25, 3.1 or 1.6 ng enzyme was added per 25 µL reaction containing a final concentration of 1× KapaHifi Fidelity buffer, 2.5 mM MgCl2, 120 nM primer M13mp18-R (5'-AACGCCAGGGTTTTCCCAGTCACGACGT-TGTAAAACGACG-3' (SEQ ID NO:26)), 0.3×SYBR Green, 0.3 mM dNTP and 200 ng M13mp18 ssDNA (NEB). Primer extension was performed in an MJ MiniOpticon (BioRad) with the following protocol: 100 cycles of (30 sec at 50° C., data acquisition). Primer extension was observed as an increase in fluorescence due to binding of SYBR green to dsDNA.

The rate of increase in fluorescence (the slope of the traces) for each mutant was compared to that of wild-type Kofu. A mutant requiring half as much enzyme to give the same slope (activity) as Kofu is scored as having twice the activity. Typically, mutants required between 8-fold less to 4-fold more enzyme to give the same activity as Kofu. This is equivalent to the mutants having between 8-fold more and 4-fold less activity than Kofu.

An increase in activity at a given protein concentration, may be due to changes in one or more of several factors. Some of these factors are: incorporation rate, off-rate and on-rate. The incorporation rate is the rate at which the enzyme incorporates nucleotides, i.e., nucleotides incorporated per unit of time. The on-rate (rate of association) is the rate at which the enzyme associates with the DNA template. The off-rate (rate of dissociation) is the rate at which the enzyme disassociates from the DNA template. The affinity of the polymerase for DNA is determined as ratio of the on-rate vs the off-rate. An increase in affinity can be due to either an increase in the on-rate or a decrease in the off-rate (at constant off-rate or on-rate, respectively).

An increase in processivity may be due to an increase in the incorporation rate or/and a decrease in the off-rate. An increase in the incorporation rate will enable incorporation of more nucleotides (assuming constant off-rate) before the enzyme and DNA disassociate. A decrease in the off-rate will increase the time the enzyme and DNA remain bound to each other, thus enabling incorporation of more nucleotides before they disassociate (assuming constant incorporation rate).

The elongation rate/enzyme activity (at a given protein concentration) is affected by the processivity and the affinity of the enzyme, and the underlying factors affecting affinity and processivity. Hence, an increase in the elongation rate/enzyme activity may be due to an increase in the incorporation rate, a decrease in the off-rate, an increase in the on-rate, or a combination thereof.

Exemplary results are shown in Table 7.

Example 10

PCR Enzyme Activity Assay

Another way of comparing enzyme activity is by using dilutions of enzyme in PCR. For each mutant and for Kofu, 25 µL reactions were set up with 2-fold dilutions of enzyme in the range 460-3.6 ng enzyme/reaction. The PCR reactions contained final concentrations of: 1× KapaHifi Fidelity buffer, 0.3 mM dNTP, 0.3 µM each of primers M13-40 (GTTTTCCCAGTCACGAC (SEQ ID NO:24)) and PKBlac-1R (GGTATCTTTATAGTCCTGTCG (SEQ ID NO:25)) and 1.4 ng/25 µL of pKB-LacIQZalfa. PCR cycling conditions were: 95° C. 2 minutes, 25×(98° C. 25 seconds, 55° C. 15 seconds, 68° C. 1 minute), 68° C. 2 minutes. The PCR products from the Kofu mutants were analyzed by gel electrophoresis and compared to that of wild-type Kofu. The highest dilution of enzyme that gave a specific product was scored. Enzymes that gave a PCR product with 2-fold less enzyme compared to Kofu were scored as having 2-fold higher activity. The activities of the mutants assayed ranged between 2-fold less active to 6-fold more active than Kofu.

Exemplary results are shown in Table 7.

TABLE 8

Sequences

Native DNA sequences of Pfu and KOD

Sequence 1
(SEQ ID NO: 1)
>Native Pfu nucleotide sequence from genomic sequence (Acc. No. AE010147)

```
   1 ATGATTTTAG ATGTGGATTA CATAACTGAA GAAGGAAAAC CTGTTATTAG GCTATTCAAA
  61 AAAGAGAACG GAAAATTTAA GATAGAGCAT GATAGAACTT TTAGACCATA CATTTACGCT
 121 CTTCTCAGGG ATGATTCAAA GATTGAAGAA GTTAAGAAAA TAACGGGGGA AAGGCATGGA
 181 AAGATTGTGA GAATTGTTGA TGTAGAGAAG GTTGAGAAAA AGTTTCTCGG CAAGCCTATT
 241 ACCGTGTGGA AACTTTATTT GGAACATCCC CAAGATGTTC CCACTATTAG AGAAAAAGTT
 301 AGAGAACATC CAGCAGTTGT GGACATCTTC GAATACGATA TTCCATTTGC AAAGAGATAC
 361 CTCATCGACA AAGGCCTAAT ACCAATGGAG GGGGAAGAAG AGCTAAAGAT TCTTGCCTTC
 421 GATATAGAAA CCCTCTATCA CGAAGGAGAA GAGTTTGGAA AAGGCCCAAT TATAATGATT
 481 AGTTATGCAG ATGAAAATGA AGCAAAGGTG ATTACTTGGA AAAACATAGA TCTTCCATAC
 541 GTTGAGGTTG TATCAAGCGA GAGAGAGATG ATAAAGAGAT TTCTCAGGAT TATCAGGGAG
 601 AAGGATCCTG ACATTATAGT TACTTATAAT GGAGACTCAT TCGACTTCCC ATATTTAGCG
 661 AAAAGGGCAG AAAAACTTGG GATTAAATTA ACCATTGGAA GAGATGGAAG CGAGCCCAAG
 721 ATGCAGAGAA TAGGCGATAT GACGGCTGTA GAAGTCAAGG GAAGAATACA TTTCGACTTG
 781 TATCATGTAA TAACAAGGAC AATAAATCTC CCAACATACA CACTAGAGGC TGTATATGAA
 841 GCAATTTTTG GAAAGCCAAA GGAGAAGGTA TACGCCGACG AGATAGCAAA AGCCTGGGAA
 901 AGTGGAGAGA ACCTTGAGAG AGTTGCCAAA TACTCGATGG AAGATGCAAA GGCAACTTAT
 961 GAACTCGGGA AGAATTCCT TCCAATGGAA ATTCAGCTTT CAAGATTAGT TGGACAACCT
1021 TTATGGGATG TTTCAAGGTC AAGCACAGGG AACCTTGTAG AGTGGTTCTT ACTTAGGAAA
1081 GCCTACGAAA GAAACGAAGT AGCTCCAAAC AAGCCAAGTG AAGAGGAGTA TCAAAGAAGG
1141 CTCAGGGAGA GCTACACAGG TGGATTCGTT AAAGAGCCAG AAAAGGGGTT GTGGGAAAAC
1201 ATAGTATACC TAGATTTTAG AGCCCTATAT CCCTCGATTA TAATTACCCA CAATGTTTCT
1261 CCCGATACTC TAAATCTTGA GGGATGCAAG AACTATGATA TCGCTCCTCA AGTAGGCCAC
1321 AAGTTCTGCA AGGACATCCC TGGTTTTATA CCAAGTCTCT TGGGACATTT GTTAGAGGAA
1381 AGACAAAAGA TTAAGACAAA AATGAAGGAA ACTCAAGATC CTATAGAAAA AATACTCCTT
1441 GACTATAGAC AAAAAGCGAT AAAACTCTTA GCAAATTCTT TCTACGGATA TTATGGCTAT
1501 GCAAAAGCAA GATGGTACTG TAAGGAGTGT GCTGAGAGCG TTACTGCCTG GGGAAGAAAG
1561 TACATCGAGT TAGTATGGAA GGAGCTCGAA GAAAAGTTTG GATTTAAAGT CCTCTACATT
1621 GACACTGATG GTCTCTATGC AACTATCCCA GGAGGAGAAA GTGAGGAAAT AAAGAAAAAG
1681 GCTCTAGAAT TTGTAAAATA CATAAATTCA AAGCTCCCTG GACTGCTAGA GCTTGAATAT
1741 GAAGGGTTTT ATAAGAGGGG ATTCTTCGTT ACGAAGAAGA GGTATGCAGT AATAGATGAA
1801 GAAGGAAAAG TCATTACTCG TGGTTTAGAG ATAGTTAGGA GAGATTGGAG TGAAATTGCA
1861 AAAGAAACTC AAGCTAGAGT TTTGGAGACA ATACTAAAAC ACGGAGATGT TGAAGAAGCT
1921 GTGAGAATAG TAAAAGAAGT AATACAAAAG CTTGCCAATT ATGAAATTCC ACCAGAGAAG
```

TABLE 8-continued

Sequences

```
1981 CTCGCAATAT ATGAGCAGAT AACAAGACCA TTACATGAGT ATAAGGCGAT AGGTCCTCAC

2041 GTAGCTGTTG CAAAGAAACT AGCTGCTAAA GGAGTTAAAA TAAAGCCAGG AATGGTAATT

2101 GGATACATAG TACTTAGAGG CGATGGTCCA ATTAGCAATA GGGCAATTCT AGCTGAGGAA

2161 TACGATCCCA AAAAGCACAA GTATGACGCA GAATATTACA TTGAGAACCA GGTTCTTCCA

2221 GCGGTACTTA GGATATTGGA GGGATTTGGA TACAGAAAGG AAGACCTCAG ATACCAAAAG

2281 ACAAGACAAG TCGGCCTAAC TTCCTGGCTT AACATTAAAA AATCCTAG
```

Sequence 2
(SEQ ID NO: 2)
>Native KOD nucleotide sequence (from genomic sequence, Acc. no. AP006878)

```
   1 ATGATCCTCG ACACTGACTA CATAACCGAG GATGGAAAGC CTGTCATAAG AATTTTCAAG

61 AAGGAAAACG GCGAGTTTAA GATTGAGTAC GACCGGACTT TTGAACCCTA CTTCTACGCC

121 CTCCTGAAGG ACGATTCTGC CATTGAGGAA GTCAAGAAGA TAACCGCCGA GAGGCACGGG

181 ACGGTTGTAA CGGTTAAGCG GGTTGAAAAG GTTCAGAAGA AGTTCCTCGG AGACCAGTT

241 GAGGTCTGGA AACTCTACTT TACTCATCCG CAGGACGTCC CAGCGATAAG GGACAAGATA

301 CGAGAGCATC CAGCAGTTAT TGACATCTAC GAGTACGACA TACCCTTCGC CAAGCGCTAC

361 CTCATAGACA AGGGATTAGT GCCAATGGAA GGCGACGAGG AGCTGAAAAT GCTCGCCTTC

421 GACATTGAAA CTCTCTACCA TGAGGGCGAG GAGTTCGCCG AGGGGCCAAT CCTTATGATA

481 AGCTACGCCG ACGAGGAAGG GGCCAGGGTG ATAACTTGGA GAACGTGGA TCTCCCCTAC

541 GTTGACGTCG TCTCGACGGA GAGGGAGATG ATAAAGCGCT TCCTCCGTGT TGTGAAGGAG

601 AAAGACCCGG ACGTTCTCAT AACCTACAAC GGCGACAACT TCGACTTCGC CTATCTGAAA

661 AAGCGCTGTG AAAAGCTCGG AATAAACTTC GCCCTCGGAA GGGATGGAAG CGAGCCGAAG

721 ATTCAGAGGA TGGGCGACAG GTTTGCCGTC GAAGTGAAGG GACGGATACA CTTCGATCTC

781 TATCCTGTGA TAAGACGGAC GATAAACCTG CCCACATACA CGCTTGAGGC CGTTTATGAA

841 GCCGTCTTCG GTCAGCCGAA GGAGAAGGTT TACGCTGAGG AAATAACCAC AGCCTGGGAA

901 ACCGGCGAGA ACCTTGAGAG AGTCGCCCGC TACTCGATGG AAGATGCGAA GGTCACATAC

961 GAGCTTGGGA AGGAGTTCCT TCCGATGGAG GCCCAGCTTT CTCGCTTAAT CGGCCAGTCC

1021 CTCTGGGACG TCTCCCGCTC CAGCACTGGC AACCTCGTTG AGTGGTTCCT CCTCAGGAAG

1081 GCCTATGAGA GGAATGAGCT GGCCCCGAAC AAGCCCGATG AAAAGGAGCT GGCCAGAAGA

1141 CGGCAGAGCT ATGAAGGAGG CTATGTAAAA GAGCCCGAGA GAGGGTTGTG GGAGAACATA

1201 GTGTACCTAG ATTTTAGATC CCTGTACCCC TCAATCATCA TCACCCACAA CGTCTCGCCG

1261 GATACGCTCA ACAGAGAAGG ATGCAAGGAA TATGACGTTG CCCCACAGGT CGGCCACCGC

1321 TTCTGCAAGG ACTTCCCAGG ATTTATCCCG AGCCTGCTTG GAGACCTCCT AGAGGAGAGG

1381 CAGAAGATAA AGAAGAAGAT GAAGGCCACG ATTGACCCGA TCGAGAGGAA GCTCCTCGAT

1441 TACAGGCAGA GGGCCATCAA GATCCTGGCA AACAGCTACT ACGGTTACTA CGGCTATGCA

1501 AGGGCGCGCT GGTACTGCAA GGAGTGTGCA GAGAGCGTAA CGGCCTGGGG AAGGGAGTAC

1561 ATAACGATGA CCATCAAGGA GATAGAGGAA AAGTACGGCT TTAAGGTAAT CTACAGCGAC

1621 ACCGACGGAT TTTTTGCCAC AATACCTGGA GCCGATGCTG AAACCGTCAA AAAGAAGGCT

1681 ATGGAGTTCC TCAAGTATAT CAACGCCAAA CTTCCGGGCG CGCTTGAGCT CGAGTACGAG

1741 GGCTTCTACA ACGCGGCTT CTTCGTCACG AAGAAGAAGT ATGCGGTGAT AGACGAGGAA

1801 GGCAAGATAA CAACGCGCGG ACTTGAGATT GTGAGGCGTG ACTGGAGCGA GATAGCGAAA

1861 GAGACGCAGG CGAGGGTTCT TGAAGCTTTG CTAAAGGACG GTGACGTCGA GAAGGCCGTG
```

TABLE 8-continued

Sequences

1921 AGGATAGTCA AAGAAGTTAC CGAAAAGCTG AGCAAGTACG AGGTTCCGCC GGAGAAGCTG

1981 GTGATCCACG AGCAGATAAC GAGGGATTTA AGGACTACA AGGCAACCGG TCCCCACGTT

2041 GCCGTTGCCA AGAGGTTGGC CGCGAGAGGA GTCAAAATAC GCCCTGGAAC GGTGATAAGC

2101 TACATCGTGC TCAAGGGCTC TGGGAGGATA GGCGACAGGG CGATACCGTT CGACGAGTTC

2161 GACCCGACGA AGCACAAGTA CGACGCCGAG TACTACATTG AGAACCAGGT TCTCCCAGCC

2221 GTTGAGAGAA TTCTGAGAGC CTTCGGTTAC CGCAAGGAAG ACCTGCGCTA CCAGAAGACG

2281 AGACAGGTTG GTTTGAGTGC TTGGCTGAAG CCGAAGGGAA CTTGA

Codon optimized sequences of Pfu and KOD

Sequence 3
(SEQ ID NO: 3)
>Pfu codon optimized nucleotide sequence

1 ATGATTCTGG ATGTGGACTA TATCACCGAA GAGGGCAAAC CGGTTATACG TTTATTTAAG

61 AAAGAGAATG GTAAATTCAA GATCGAGCAT GACCGCACGT TCCGTCCATA CATTTACGCG

121 TTGCTTCGGG ATGATAGCAA AATTGAGGAA GTCAAAAAGA TCACCGGGGA ACGTCATGGA

181 AAAATAGTAA GAATTGTGGA CGTTGAAAAA GTCGAAAAGA AATTTCTGGG CAAACCGATC

241 ACTGTATGGA AGCTCTATCT GGAACATCCT CAGGATGTGC CCACAATTCG AGAAAAAGTT

301 CGTGAGCACC CAGCCGTCGT GGATATATTT GAATATGACA TCCCTTTTGC AAAACGCTAC

361 TTAATTGATA AAGGCCTGAT CCCGATGGAG GGGGAAGAAG AACTTAAAAT TCTGGCTTTT

421 GACATAGAAA CGCTCTATCA TGAGGGAGAA GAATTTGGCA AAGGTCCCAT CATTATGATT

481 TCTTACGCGG ATGAGAACGA AGCCAAGGTA ATCACTTGGA AAAATATTGA CCTGCCGTAC

541 GTTGAAGTGG TCAGTTCAGA GCGGGAAATG ATTAAACGTT TTTTACGCAT CATTAGAGAG

601 AAAGATCCAG ATATAATCGT TACATATAAC GGCGACTCCT TCGATTTTCC TTACCTGGCA

661 AAACGAGCTG AAAAATTGGG TATTAAACTT ACCATCGGGC GTGACGGATC GGAACCGAAA

721 ATGCAACGCA TTGGCGATAT GACGGCGGTA GAGGTGAAAG GTCGGATACA CTTTGATCTG

781 TATCATGTCA TCACCCGTAC TATTAATCTC CCCACATACA CGTTAGAAGC CGTTTATGAG

841 GCAATATTCG GCAAGCCGAA AGAAAAAGTG TACGCTGACG AAATCGCGAA GGCATGGGAG

901 AGCGGCGAAA ACCTGGAGCG CGTAGCAAAA TATTCTATGG AAGATGCTAA AGCGACCTAC

961 GAATTGGGGA AGAATTTCT TCCAATGGAA ATTCAGCTGA GTCGTTTAGT CGGACAACCT

1021 CTGTGGGACG TTTCACGCTC CTCGACTGGC AATCTCGTGG AGTGGTTCCT GTTGAGAAAA

1081 GCCTATGAAC GAAACGAAGT AGCACCGAAT AAACCAAGCG AGGAAGAATA TCAGCGTCGC

1141 CTTCGCGAGT CTTACACAGG TGGGTTTGTT AAGGAACCGG AGAAAGGTCT TTGGGAAAAC

1201 ATCGTGTATT TAGATTTCCG TGCGCTGTAC CCCAGTATTA TAATCACCCA CAATGTCTCA

1261 CCTGACACGC TCAACTTGGA AGGTTGCAAA AATTATGATA TTGCTCCGCA AGTTGGACAT

1321 AAGTTTTGTA AAGATATTCC GGGCTTCATC CCGTCCCTGC TTGGTCACTT ACTGGAAGAG

1381 CGCCAAAAAA TTAAGACCAA AATGAAAGAG ACTCAGGATC CCATTGAAAA GATCCTGCTC

1441 GATTACCGGC AAAAAGCCAT TAAATTGCTT GCAAACTCGT TTTATGGGTA CTATGGCTAT

1501 GCGAAGGCTC GTTGGTACTG CAAAGAATGT GCCGAGAGCG TGACAGCATG GGGTCGCAAA

1561 TATATAGAAT TAGTATGGAA GGAGCTGGAA GAAAAATTCG GATTCAAAGT CCTGTACATC

1621 GATACGGATG GCCTCTATGC GACCATTCCT GGTGGGGAGT CTGAAGAAAT CAAGAAAAAA

1681 GCCTTGGAAT TCGTTAAGTA CATTAATAGT AAATTACCGG GACTGCTTGA ACTGGAGTAT

TABLE 8-continued

Sequences

```
1741 GAAGGCTTCT ACAAAAGAGG TTTTTTCGTT ACTAAGAAAC GATATGCCGT AATAGATGAA

1801 GAGGGGAAAG TCATCACACG TGGCCTCGAG ATTGTTCGCC GGGACTGGTC AGAGATAGCA

1861 AAGGAAACGC AGGCGCGCGT GCTCGAAACC ATCTTGAAAC ATGGTGATGT AGAGGAAGCC

1921 GTCCGCATTG TTAAAGAGGT GATCCAGAAG TTAGCAAACT ATGAAATTCC ACCGGAAAAA

1981 CTGGCGATAT ACGAGCAAAT CACTCGTCCC CTTCACGAAT ATAAAGCTAT GGACCTCAT

2041 GTAGCCGTCG CGAAGAAACT GGCTGCAAAA GGCGTTAAGA TAAAACCAGG TATGGTGATC

2101 GGGTACATTG TACTCCGCGG CGACGGTCCG ATTTCCAATA GAGCCATCTT GGCGGAGGAA

2161 TATGATCCTA AAAAGCATAA ATACGACGCT GAATATTACA TTGAGAACCA GGTCTTGCCG

2221 GCAGTTCTGC GGATACTTGA AGGATTTGGC TATCGTAAAG AAGATCTGCG CTATCAAAAG

2281 ACGCGACAGG TGGGTCTGAC TAGCTGGTTG AATATCAAAA AATCGTAA
```

Sequence 4 (SEQ ID NO: 4)
>Pfu codon optimized nucleotide sequence, extra 9 nt in 5' area.

```
   1 ATGGCTAGCG CCATTCTGGA TGTGGACTAT ATCACCGAAG AGGGCAAACC GGTTATACGT

61 TTATTTAAGA AGAGAATGG TAAATTCAAG ATCGAGCATG ACCGCACGTT CCGTCCATAC

121 ATTTACGCGT TGCTTCGGGA TGATAGCAAA ATTGAGGAAG TCAAAAGAT CACCGGGGAA

181 CGTCATGGAA AATAGTAAG AATTGTGGAC GTTGAAAAAG TCGAAAGAA ATTTCTGGGC

241 AAACCGATCA CTGTATGGAA GCTCTATCTG GAACATCCTC AGGATGTGCC CACAATTCGA

301 GAAAAAGTTC GTGAGCACCC AGCCGTCGTG GATATATTTG AATATGACAT CCCTTTTGCA

361 AAACGCTACT TAATTGATAA AGGCCTGATC CCGATGGAGG GGGAAGAAGA ACTTAAAATT

421 CTGGCTTTTG ACATAGAAAC GCTCTATCAT GAGGAGAGA AATTTGGCAA AGGTCCCATC

481 ATTATGATTT CTTACGCGGA TGAGAACGAA GCCAAGGTAA TCACTTGGAA AAATATTGAC

541 CTGCCGTACG TTGAAGTGGT CAGTTCAGAG CGGGAAATGA TTAAACGTTT TTTACGCATC

601 ATTAGAGAGA AGATCCAGA TATAATCGTT ACATATAACG GCGACTCCTT CGATTTTCCT

661 TACCTGGCAA AACGAGCTGA AAAATTGGGT ATTAAACTTA CCATCGGGCG TGACGGATCG

721 GAACCGAAAA TGCAACGCAT TGGCGATATG ACGGCGGTAG AGGTGAAAGG TCGGATACAC

781 TTTGATCTGT ATCATGTCAT CACCCGTACT ATTAATCTCC CCACATACAC GTTAGAAGCC

841 GTTTATGAGG CAATATTCGG CAAGCCGAAA GAAAAAGTGT ACGCTGACGA AATCGCGAAG

901 GCATGGGAGA GCGGCGAAAA CCTGGAGCGC GTAGCAAAAT ATTCTATGGA AGATGCTAAA

961 GCGACCTACG AATTGGGGAA AGAATTTCTT CCAATGGAAA TTCAGCTGAG TCGTTTAGTC

1021 GGACAACCTC TGTGGGACGT TTCACGCTCC TCGACTGGCA ATCTCGTGGA GTGGTTCCTG

1081 TTGAGAAAAG CCTATGAACG AAACGAAGTA GCACCGAATA AACCAAGCGA GGAAGAATAT

1141 CAGCGTCGCC TTCGCGAGTC TTACACAGGT GGGTTTGTTA AGGAACCGGA GAAAGGTCTT

1201 TGGGAAAACA TCGTGTATTT AGATTTCCGT GCGCTGTACC CCAGTATTAT AATCACCCAC

1261 AATGTCTCAC CTGACACGCT CAACTTGGAA GGTTGCAAAA ATTATGATAT TGCTCCGCAA

1321 GTTGGACATA AGTTTTGTAA AGATATTCCG GGCTTCATCC CGTCCCTGCT TGGTCACTTA

1381 CTGGAAGAGC GCCAAAAAAT TAAGACCAAA ATGAAAGAGA CTCAGGATCC CATTGAAAAG

1441 ATCCTGCTCG ATTACCGGCA AAAAGCCATT AAATTGCTTG CAAACTCGTT TTATGGGTAC

1501 TATGGCTATG CGAAGGCTCG TTGGTACTGC AAAGAATGTG CCGAGAGCGT GACAGCATGG

1561 GGTCGCAAAT ATATAGAATT AGTATGGAAG GAGCTGGAAG AAAAATTCGG ATTCAAAGTC

1621 CTGTACATCG ATACGGATGG CCTCTATGCG ACCATTCCTG GTGGGGAGTC TGAAGAAATC
```

TABLE 8-continued

Sequences

```
1681 AAGAAAAAAG CCTTGGAATT CGTTAAGTAC ATTAATAGTA AATTACCGGG ACTGCTTGAA

1741 CTGGAGTATG AAGGCTTCTA CAAAAGAGGT TTTTTCGTTA CTAAGAAACG ATATGCCGTA

1801 ATAGATGAAG AGGGGAAAGT CATCACACGT GGCCTCGAGA TTGTTCGCCG GGACTGGTCA

1861 GAGATAGCAA AGGAAACGCA GGCGCGCGTG CTCGAAACCA TCTTGAAACA TGGTGATGTA

1921 GAGGAAGCCG TCCGCATTGT TAAAGAGGTG ATCCAGAAGT TAGCAAACTA TGAAATTCCA

1981 CCGGAAAAAC TGGCGATATA CGAGCAAATC ACTCGTCCCC TTCACGAATA TAAAGCTATT

2041 GGACCTCATG TAGCCGTCGC GAAGAAACTG GCTGCAAAAG GCGTTAAGAT AAAACCAGGT

2101 ATGGTGATCG GGTACATTGT ACTCCGCGGC GACGGTCCGA TTTCCAATAG AGCCATCTTG

2161 GCGGAGGAAT ATGATCCTAA AAAGCATAAA TACGACGCTG AATATTACAT TGAGAACCAG

2221 GTCTTGCCGG CAGTTCTGCG GATACTTGAA GGATTTGGCT ATCGTAAAGA AGATCTGCGC

2281 TATCAAAAGA CGCGACAGGT GGGTCTGACT AGCTGGTTGA ATATCAAAAA ATCGTAA
```

Sequence 5

(SEQ ID NO: 5)

>KOD codon optimized nucleotide sequence

```
   1 ATGATTCTGG ATACCGACTA TATCACGGAA GATGGCAAAC CGGTGATACG TATTTTTAAG

61 AAAGAGAATG GTGAGTTCAA AATCGAGTAC GACCGCACTT TTGAGCCATA TTTCTACGCG

121 TTACTGAAGG ACGATAGCGC CATTGAAGAA GTTAAAAAAA TCACCGCAGA GCGGCATGGG

181 ACAGTGGTAA CCGTGAAGAG AGTTGAAAAA GTCCAGAAAA AATTTTTGGG ACGACCTGTA

241 GAAGTGTGGA AACTTTATTT CACTCACCCC CAAGATGTTC CGGCTATACG TGATAAAATT

301 CGCGAACATC CAGCGGTCAT TGATATTTAC GAATATGATA TACCTTTTGC CAAGCGTTAC

361 CTCATCGACA AAGGCCTGGT GCCGATGGAA GGTGATGAAG AATTAAAAAT GTTGGCATTC

421 GACATTGAAA CACTTTATCA CGAGGGGGAA GAGTTTGCTG AGGGTCCCAT CCTGATGATT

481 TCTTATGCGG ATGAAGAGGG TGCCCGCGTA ATAACCTGGA AGAACGTTGA CTCCCCGTAC

541 GTGGACGTCG TTAGTACGGA ACGGGAAATG ATCAAACGTT TCCTGCGCGT AGTGAAAGAG

601 AAAGATCCAG ACGTCTTAAT TACCTATAAT GGTGATAACT TTGATTTTGC ATACCTGAAA

661 AAAAGATGCG AAAGTTGGG CATAAATTTC GCTCTTGGTC GAGACGGGTC AGAGCCTAAA

721 ATCCAGCGTA TGGGAGATCG CTTTGCGGTT GAAGTGAAAG GCCGGATTCA TTTCGACCTG

781 TATCCGGTAA TTCGTCGCAC TATCAACCTC CCCACATACA CGTTAGAAGC CGTCTATGAG

841 GCAGTTTTTG GTCAACCGAA GGAAAAAGTT TACGCTGAGG AAATTACCAC TGCGTGGGAA

901 ACAGGCGAGA ATCTGGAACG TGTAGCCCGC TATTCTATGG AGGATGCAAA AGTTACCTAT

961 GAATTGGGTA AGGAATTTCT TCCAATGGAG GCGCAGCTGT CGAGATTAAT AGGGCAGAGC

1021 CTGTGGGACG TGTCTCGAAG TTCAACGGGA AACCTCGTCG AATGGTTTCT GTTGCGGAAA

1081 GCATACGAGC GTAATGAACT TGCCCCTAAC AAACCGGATG AAAAGGAGCT GGCACGCCGT

1141 CGCCAATCCT ATGAAGGCGG TTACGTTAAA GAACCAGAGC GGGGGTTATG GGAAAATATC

1201 GTGTATCTGG ATTTCCGTTC GCTCTACCCG AGCATTATCA TTACCCACAA CGTATCTCCC

1261 GACACTTTGA ATCGCGAGGG CTGTAAAGAA TATGATGTCG CGCCGCAGGT TGGTCATAGA

1321 TTTTGCAAGG ACTTCCCGGG ATTTATACCA AGTCTGCTTG CGATTTACT GGAAGAGCGA

1381 CAAAAAATCA AAAGAAAAT GAAAGCTACA ATCGATCCGA TAGAACGTAA GCTGCTCGAC

1441 TACCGCCAGC GGGCCATCAA ATTTTGGCA AACTCATATT ATGGTTACTA TGGGTACGCG

1501 CGTGCTCGCT GGTATTGTAA AGAGTGCGCC GAATCCGTGA CGGCATGGGG CCGTGAATAC
```

TABLE 8-continued

Sequences

```
1561 ATCACCATGA CTATTAAGGA GATAGAAGAG AAATATGGTT TCAAAGTAAT CTACTCGGAT

1621 ACAGACGGAT TCTTTGCGAC GATTCCCGGT GCCGATGCAG AAACCGTCAA GAAAAAGCG

1681 ATGGAATTCC TTAAGTATAT AAATGCTAAA TTACCTGGTG CCCTGGAGCT GGAATACGAA

1741 GGGTTTTACA AACGCGGATT CTTTGTTACT AAGAAAAAAT ATGCGGTGAT CGACGAGGAA

1801 GGCAAGATTA CGACCAGAGG CCTCGAGATT GTACGGCGTG ATTGGAGCGA AATCGCTAAA

1861 GAAACACAGG CACGTGTCTT GGAGGCATTA CTGAAAGATG GGACGTTGA AAAGGCGGTG

1921 CGAATTGTAA AAGAAGTCAC CGAAAAACTT TCTAAGTACG AAGTTCCGCC AGAGAAACTG

1981 GTGATACACG AACAAATCAC TCGTGATCTG AAAGACTATA AGGCTACAGG CCCGCATGTA

2041 GCAGTCGCCA ACGCCTCGC GGCTCGGGGT GTTAAAATTC GTCCCGGAAC GGTGATCAGT

2101 TACATTGTAT TGAAGGGCTC AGGTCGCATA GGGGATAGAG CAATCCCTTT CGACGAGTTT

2161 GATCCAACCA ACACAAATA TGATGCCGAA TACTATATTG AAAACCAGGT CTTGCCGGCG

2221 GTTGAGCGTA TACTGCGCGC TTTCGGCTAT CGAAAGGAAG ATCTTCGTTA CCAAAAAACT

2281 AGACAGGTGG GTCTGTCCGC ATGGCTCAAA CCTAAGGGAA CGTAA
```

Sequence 6
(SEQ ID NO: 6)
>KOD codon optimized nucleotide sequence, extra 9 nt in 5' area.

```
  1 ATGGCTAGCG CCATTCTGGA TACCGACTAT ATCACGGAAG ATGGCAAACC GGTGATACGT

61 ATTTTTAAGA AGGAGAATGG TGAGTTCAAA ATCGAGTACG ACCGCACTTT TGAGCCATAT

121 TTCTACGCGT TACTGAAGGA CGATAGCGCC ATTGAAGAAG TTAAAAAAAT CACCGCAGAG

181 CGGCATGGGA CAGTGGTAAC CGTGAAGAGA GTTGAAAAAG TCCAGAAAAA ATTTTTGGGA

241 CGACCTGTAG AAGTGTGGAA ACTTTATTTC ACTCACCCCC AAGATGTTCC GGCTATACGT

301 GATAAAATTC GCGAACATCC AGCGGTCATT GATATTTACG AATATGATAT ACCTTTTGCC

361 AAGCGTTACC TCATCGACAA AGGCCTGGTG CCGATGGAAG GTGATGAAGA ATTAAAAATG

421 TTGGCATTCG ACATTGAAAC ACTTTATCAC GAGGGGGAAG AGTTTGCTGA GGGTCCCATC

481 CTGATGATTT CTTATGCGGA TGAAGAGGGT GCCCGCGTAA TAACCTGGAA GAACGTTGAT

541 CTCCCGTACG TGGACGTCGT TAGTACGGAA CGGGAAATGA TCAAACGTTT CCTGCGCGTA

601 GTGAAAGAGA AAGATCCAGA CGTCTTAATT ACCTATAATG GTGATAACTT TGATTTTGCA

661 TACCTGAAAA AAAGATGCGA AAAGTTGGGC ATAAATTTCG CTCTTGGTCG AGACGGGTCA

721 GAGCCTAAAA TCCAGCGTAT GGGAGATCGC TTTGCGGTTG AAGTGAAAGG CCGGATTCAT

781 TTCGACCTGT ATCCGGTAAT TCGTCGCACT ATCAACCTCC CCACATACAC GTTAGAAGCC

841 GTCTATGAGG CAGTTTTTGG TCAACCGAAG GAAAAAGTTT ACGCTGAGGA AATTACCACT

901 GCGTGGGAAA CAGGCGAGAA TCTGGAACGT GTAGCCCGCT ATTCTATGGA GGATGCAAAA

961 GTTACCTATG AATTGGGTAA GGAATTTCTT CCAATGGAGG CGCAGCTGTC GAGATTAATA

1021 GGGCAGAGCC TGTGGGACGT GTCTCGAAGT TCAACGGGAA ACCTCGTCGA ATGGTTTCTG

1081 TTGCGGAAAG CATACGAGCG TAATGAACTT GCCCCTAACA AACCGGATGA AAAGGAGCTG

1141 GCACGCCGTC GCCAATCCTA TGAAGGCGGT TACGTTAAAG AACCAGAGCG GGGGTTATGG

1201 GAAAATATCG TGTATCTGGA TTTCCGTTCG CTCTACCCGA GCATTATCAT TACCCACAAC

1261 GTATCTCCCG ACACTTTGAA TCGCGAGGGC TGTAAAGAAT ATGATGTCGC GCCGCAGGTT

1321 GGTCATAGAT TTTGCAAGGA CTTCCCGGGA TTTATACCAA GTCTGCTTGG CGATTTACTG

1381 GAAGAGCGAC AAAAAATCAA AAAGAAAATG AAAGCTACAA TCGATCCGAT AGAACGTAAG

1441 CTGCTCGACT ACCGCCAGCG GGCCATCAAA ATTTTGGCAA ACTCATATTA TGGTTACTAT
```

TABLE 8-continued

Sequences

```
1501 GGGTACGCGC GTGCTCGCTG GTATTGTAAA GAGTGCGCCG AATCCGTGAC GGCATGGGGC

1561 CGTGAATACA TCACCATGAC TATTAAGGAG ATAGAAGAGA AATATGGTTT CAAAGTAATC

1621 TACTCGGATA CAGACGGATT CTTTGCGACG ATTCCCGGTG CCGATGCAGA AACCGTCAAG

1681 AAAAAAGCGA TGGAATTCCT TAAGTATATA AATGCTAAAT TACCTGGTGC CCTGGAGCTG

1741 GAATACGAAG GGTTTTACAA ACGCGGATTC TTTGTTACTA AGAAAAAATA TGCGGTGATC

1801 GACGAGGAAG GCAAGATTAC GACCAGAGGC CTCGAGATTG TACGGCGTGA TTGGAGCGAA

1861 ATCGCTAAAG AAACACAGGC ACGTGTCTTG GAGGCATTAC TGAAAGATGG GGACGTTGAA

1921 AAGGCGGTGC GAATTGTAAA AGAAGTCACC GAAAAACTTT CTAAGTACGA AGTTCCGCCA

1981 GAGAAACTGG TGATACACGA ACAAATCACT CGTGATCTGA AGACTATAA GGCTACAGGC

2041 CCGCATGTAG CAGTCGCCAA ACGCCTCGCG GCTCGGGGTG TTAAAATTCG TCCCGGAACG

2101 GTGATCAGTT ACATTGTATT GAAGGGCTCA GGTCGCATAG GGGATAGAGC AATCCCTTTC

2161 GACGAGTTTG ATCCAACCAA ACACAAATAT GATGCCGAAT ACTATATTGA AAACCAGGTC

2221 TTGCCGGCGG TTGAGCGTAT ACTGCGCGCT TTCGGCTATC GAAAGGAAGA TCTTCGTTAC

2281 CAAAAAACTA GACAGGTGGG TCTGTCCGCA TGGCTCAAAC CTAAGGGAAC GTAA
```

Sequence 7
(SEQ ID NO: 7)
>pKB13-Pfu codon optimized nucleotide sequence in pUC19 vector

```
  1 TCGCGCGTTT CGGTGATGAC GGTGAAAACC TCTGACACAT GCAGCTCCCG GAGACGGTCA

61 CAGCTTGTCT GTAAGCGGAT GCCGGGAGCA GACAAGCCCG TCAGGGCGCG TCAGCGGGTG

121 TTGGCGGGTG TCGGGGCTGG CTTAACTATG CGGCATCAGA GCAGATTGTA CTGAGAGTGC

181 ACCATATGCG GTGTGAAATA CCGCACAGAT GCGTAAGGAG AAAATACCGC ATCAGGCGCC

241 ATTCGCCATT CAGGCTGCGC AACTGTTGGG AAGGGCGATC GGTGCGGGCC TCTTCGCTAT

301 TACGCCAGCT GGCGAAAGGG GGATGTGCTG CAAGGCGATT AAGTTGGGTA ACGCCAGGGT

361 TTTCCCAGTC ACGACGTTGT AAAACGACGG CCAGTGAATT CGGTCTCAGC GCCATTCTGG

421 ATACCGACTA TATCACGGAA GATGGCAAAC CGGTGATACG TATTTTTAAG AAAGAGAATG

481 GTGAGTTCAA AATCGAGTAC GACCGCACTT TTGAGCCATA TTTCTACGCG TTACTGAAGG

541 ACGATAGCGC CATTGAAGAA GTTAAAAAAA TCACCGCAGA GCGGCATGGG ACAGTGGTAA

601 CCGTGAAGAG AGTTGAAAAA GTCCAGAAAA AATTTTTGGG ACGACCTGTA GAAGTGTGGA

661 AACTTTATTT CACTCACCCC CAAGATGTTC CGGCTATACG TGATAAAATT CGCGAACATC

721 CAGCGGTCAT TGATATTTAC GAATATGATA TACCTTTTGC CAAGCGTTAC CTCATCGACA

781 AAGGCCTGGT GCCGATGGAA GGTGATGAAG AATTAAAAAT GTTGGCATTC GACATTGAAA

841 CACTTTATCA CGAGGGGGAA GAGTTTGCTG AGGGTCCCAT CCTGATGATT TCTTATGCGG

901 ATGAAGAGGG TGCCCGCGTA ATAACCTGGA AGAACGTTGA TCTCCCGTAC GTGGACGTCG

961 TTAGTACGGA ACGGGAAATG ATCAAACGTT TCCTGCGCGT AGTGAAAGAG AAAGATCCAG

1021 ACGTCTTAAT TACCTATAAT GGTGATAACT TTGATTTTGC ATACCTGAAA AAAAGATGCG

1081 AAAAGTTGGG CATAAATTTC GCTCTTGGTC GAGACGGGTC AGAGCCTAAA ATCCAGCGTA

1141 TGGGAGATCG CTTTGCGGTT GAAGTGAAAG GCCGGATTCA TTTCGACCTG TATCCGGTAA

1201 TTCGTCGCAC TATCAACCTC CCCACATACA CGTTAGAAGC CGTCTATGAG GCAGTTTTTG

1261 GTCAACCGAA GGAAAAGTT TACGCTGAGG AAATTACCAC TGCGTGGGAA ACAGGCGAGA

1321 ATCTGGAACG TGTAGCCCGC TATTCTATGG AGGATGCAAA AGTTACCTAT GAATTGGGTA
```

TABLE 8-continued

Sequences

```
1381 AGGAATTTCT TCCAATGGAG GCGCAGCTGT CGAGATTAAT AGGGCAGAGC CTGTGGGACG
1441 TGTCTCGAAG TTCAACGGGA AACCTCGTCG AATGGTTTCT GTTGCGGAAA GCATACGAGC
1501 GTAATGAACT TGCCCCTAAC AAACCGGATG AAAAGGAGCT GGCACGCCGT CGCCAATCCT
1561 ATGAAGGCGG TTACGTTAAA GAACCAGAGC GGGGGTTATG GGAAAATATC GTGTATCTGG
1621 ATTTCCGTTC GCTCTACCCG AGCATTATCA TTACCCACAA CGTATCTCCC GACACTTTGA
1681 ATCGCGAGGG CTGTAAAGAA TATGATGTCG CGCCGCAGGT TGGTCATAGA TTTTGCAAGG
1741 ACTTCCCGGG ATTTATACCA AGTCTGCTTG GCGATTTACT GGAAGAGCGA CAAAAAATCA
1801 AAAGAAAAT GAAAGCTACA ATCGATCCGA TAGAACGTAA GCTGCTCGAC TACCGCCAGC
1861 GGGCCATCAA AATTTTGGCA AACTCATATT ATGGTTACTA TGGGTACGCG CGTGCTCGCT
1921 GGTATTGTAA AGAGTGCGCC GAATCCGTGA CGGCATGGGG CCGTGAATAC ATCACCATGA
1981 CTATTAAGGA GATAGAAGAG AAATATGGTT TCAAAGTAAT CTACTCGGAT ACAGACGGAT
2041 TCTTTGCGAC GATTCCCGGT GCCGATGCAG AAACCGTCAA GAAAAAAGCG ATGGAATTCC
2101 TTAAGTATAT AAATGCTAAA TTACCTGGTG CCCTGGAGCT GGAATACGAA GGGTTTTACA
2161 AACGCGGATT CTTTGTTACT AAGAAAAAAT ATGCGGTGAT CGACGAGGAA GGCAAGATTA
2221 CGACCAGAGG CCTCGAGATT GTACGGCGTG ATTGGAGCGA AATCGCTAAA GAAACACAGG
2281 CACGTGTCTT GGAGGCATTA CTGAAAGATG GGGACGTTGA AAAGGCGGTG CGAATTGTAA
2341 AAGAAGTCAC CGAAAAACTT TCTAAGTACG AAGTTCCGCC AGAGAAACTG GTGATACACG
2401 AACAAATCAC TCGTGATCTG AAAGACTATA AGGCTACAGG CCCGCATGTA GCAGTCGCCA
2461 AACGCCTCGC GGCTCGGGGT GTTAAAATTC GTCCCGGAAC GGTGATCAGT TACATTGTAT
2521 TGAAGGGCTC AGGTCGCATA GGGGATAGAG CAATCCCTTT CGACGAGTTT GATCCAACCA
2581 AACACAAATA TGATGCCGAA TACTATATTG AAAACCAGGT CTTGCCGGCG GTTGAGCGTA
2641 TACTGCGCGC TTTCGGCTAT CGAAAGGAAG ATCTTCGTTA CCAAAAAACT AGACAGGTGG
2701 GTCTGTCCGC ATGGCTCAAA CCTAAGGGAA CGTAATGATA TGAGACCGGA TCCTCTAGAG
2761 TCGACCTGCA GGCATGCAAG CTTGGCGTAA TCATGGTCAT AGCTGTTTCC TGTGTGAAAT
2821 TGTTATCCGC TCACAATTCC ACACAACATA CGAGCCGGAA GCATAAAGTG TAAAGCCTGG
2881 GGTGCCTAAT GAGTGAGCTA ACTCACATTA ATTGCGTTGC GCTCACTGCC CGCTTTCCAG
2941 TCGGGAAACC TGTCGTGCCA GCTGCATTAA TGAATCGGCC AACGCGCGGG GAGAGGCGGT
3001 TTGCGTATTG GGCGCTCTTC CGCTTCCTCG CTCACTGACT CGCTGCGCTC GGTCGTTCGG
3061 CTGCGGCGAG CGGTATCAGC TCACTCAAAG GCGGTAATAC GGTTATCCAC AGAATCAGGG
3121 GATAACGCAG GAAAGAACAT GTGAGCAAAA GGCCAGCAAA AGGCCAGGAA CCGTAAAAAG
3181 GCCGCGTTGC TGGCGTTTTT CCATAGGCTC CGCCCCCCTG ACGAGCATCA CAAAAATCGA
3241 CGCTCAAGTC AGAGGTGGCG AAACCCGACA GGACTATAAA GATACCAGGC GTTTCCCCCT
3301 GGAAGCTCCC TCGTGCGCTC TCCTGTTCCG ACCCTGCCGC TTACCGGATA CCTGTCCGCC
3361 TTTCTCCCTT CGGGAAGCGT GGCGCTTTCT CATAGCTCAC GCTGTAGGTA TCTCAGTTCG
3421 GTGTAGGTCG TTCGCTCCAA GCTGGGCTGT GTGCACGAAC CCCCCGTTCA GCCCGACCGC
3481 TGCGCCTTAT CCGGTAACTA TCGTCTTGAG TCCAACCCGG TAAGACACGA CTTATCGCCA
3541 CTGGCAGCAG CCACTGGTAA CAGGATTAGC AGAGCGAGGT ATGTAGGCGG TGCTACAGAG
3601 TTCTTGAAGT GGTGGCCTAA CTACGGCTAC ACTAGAAGAA CAGTATTTGG TATCTGCGCT
3661 CTGCTGAAGC CAGTTACCTT CGGAAAAAGA GTTGGTAGCT CTTGATCCGG CAAACAAACC
```

TABLE 8-continued

Sequences

3721 ACCGCTGGTA GCGGTGGTTT TTTTGTTTGC AAGCAGCAGA TTACGCGCAG AAAAAAGGA

3781 TCTCAAGAAG ATCCTTTGAT CTTTTCTACG GGGTCTGACG CTCAGTGGAA CGAAAACTCA

3841 CGTTAAGGGA TTTTGGTCAT GAGATTATCA AAAAGGATCT TCACCTAGAT CCTTTTAAAT

3901 TAAAAATGAA GTTTTAAATC AATCTAAAGT ATATATGAGT AAACTTGGTC TGACAGTTAC

3961 CAATGCTTAA TCAGTGAGGC ACCTATCTCA GCGATCTGTC TATTTCGTTC ATCCATAGTT

4021 GCCTGACTCC CCGTCGTGTA GATAACTACG ATACGGGAGG GCTTACCATC TGGCCCCAGT

4081 GCTGCAATGA TACCGCGAGA CCCACGCTCA CCGGCTCCAG ATTTATCAGC AATAAACCAG

4141 CCAGCCGGAA GGGCCGAGCG CAGAAGTGGT CCTGCAACTT TATCCGCCTC CATCCAGTCT

4201 ATTAATTGTT GCCGGGAAGC TAGAGTAAGT AGTTCGCCAG TTAATAGTTT GCGCAACGTT

4261 GTTGCCATTG CTACAGGCAT CGTGGTGTCA CGCTCGTCGT TTGGTATGGC TTCATTCAGC

4321 TCCGGTTCCC AACGATCAAG GCGAGTTACA TGATCCCCCA TGTTGTGCAA AAAAGCGGTT

4381 AGCTCCTTCG GTCCTCCGAT CGTTGTCAGA AGTAAGTTGG CCGCAGTGTT ATCACTCATG

4441 GTTATGGCAG CACTGCATAA TTCTCTTACT GTCATGCCAT CCGTAAGATG CTTTTCTGTG

4501 ACTGGTGAGT ACTCAACCAA GTCATTCTGA GAATAGTGTA TGCGGCGACC GAGTTGCTCT

4561 TGCCCGGCGT CAATACGGGA TAATACCGCG CCACATAGCA GAACTTTAAA AGTGCTCATC

4621 ATTGGAAAAC GTTCTTCGGG GCGAAAACTC TCAAGGATCT TACCGCTGTT GAGATCCAGT

4681 TCGATGTAAC CCACTCGTGC ACCCAACTGA TCTTCAGCAT CTTTTACTTT CACCAGCGTT

4741 TCTGGGTGAG CAAAAACAGG AAGGCAAAAT GCCGCAAAAA AGGGAATAAG GGCGACACGG

4801 AAATGTTGAA TACTCATACT CTTCCTTTTT CAATATTATT GAAGCATTTA TCAGGGTTAT

4861 TGTCTCATGA GCGGATACAT ATTTGAATGT ATTTAGAAAA ATAAACAAAT AGGGGTTCCG

4921 CGCACATTTC CCCGAAAAGT GCCACCTGAC GTCTAAGAAA CCATTATTAT CATGACATTA

4981 ACCTATAAAA ATAGGCGTAT CACGAGGCCC TTTCGTC

Sequence 8
(SEQ ID NO: 8)
>pKB8-KOD codon optimized nucleotide sequence in pUC19 vector

1 TCGCGCGTTT CGGTGATGAC GGTGAAAACC TCTGACACAT GCAGCTCCCG GAGACGGTCA

61 CAGCTTGTCT GTAAGCGGAT GCCGGGAGCA GACAAGCCCG TCAGGGCGCG TCAGCGGGTG

121 TTGGCGGGTG TCGGGCTGG CTTAACTATG CGGCATCAGA GCAGATTGTA CTGAGAGTGC

181 ACCATATGCG GTGTGAAATA CCGCACAGAT GCGTAAGGAG AAAATACCGC ATCAGGCGCC

241 ATTCGCCATT CAGGCTGCGC AACTGTTGGG AAGGGCGATC GGTGCGGGCC TCTTCGCTAT

301 TACGCCAGCT GGCGAAAGGG GGATGTGCTG CAAGGCGATT AAGTTGGGTA ACGCCAGGGT

361 TTTCCCAGTC ACGACGTTGT AAAACGACGG CCAGTGAATT CGGTCTCAGC GCCATTCTGG

421 ATACCGACTA TATCACGGAA GATGGCAAAC CGGTGATACG TATTTTTAAG AAAGAGAATG

481 GTGAGTTCAA AATCGAGTAC GACCGCACTT TTGAGCCATA TTTCTACGCG TTACTGAAGG

541 ACGATAGCGC CATTGAAGAA GTTAAAAAAA TCACCGCAGA GCGGCATGGG ACAGTGGTAA

601 CCGTGAAGAG AGTTGAAAAA GTCCAGAAAA ATTTTTGGG ACGACCTGTA GAAGTGTGGA

661 AACTTTATTT CACTCACCCC CAAGATGTTC CGGCTATACG TGATAAAATT CGCGAACATC

721 CAGCGGTCAT TGATATTTAC GAATATGATA TACCTTTTGC CAAGCGTTAC CTCATCGACA

781 AAGGCCTGGT GCCGATGGAA GGTGATGAAG AATTAAAAAT GTTGGCATTC GACATTGAAA

841 CACTTTATCA CGAGGGGGAA GAGTTTGCTG AGGGTCCCAT CCTGATGATT TCTTATGCGG

901 ATGAAGAGGG TGCCCGCGTA ATAACCTGGA AGAACGTTGA TCTCCCGTAC GTGGACGTCG

TABLE 8-continued

Sequences

```
 961 TTAGTACGGA ACGGGAAATG ATCAAACGTT TCCTGCGCGT AGTGAAAGAG AAAGATCCAG

1021 ACGTCTTAAT TACCTATAAT GGTGATAACT TTGATTTTGC ATACCTGAAA AAAGATGCG

1081 AAAAGTTGGG CATAAATTTC GCTCTTGGTC GAGACGGGTC AGAGCCTAAA ATCCAGCGTA

1141 TGGGAGATCG CTTTGCGGTT GAAGTGAAAG GCCGGATTCA TTTCGACCTG TATCCGGTAA

1201 TTCGTCGCAC TATCAACCTC CCCACATACA CGTTAGAAGC CGTCTATGAG GCAGTTTTTG

1261 GTCAACCGAA GGAAAAAGTT TACGCTGAGG AAATTACCAC TGCGTGGGAA ACAGGCGAGA

1321 ATCTGGAACG TGTAGCCCGC TATTCTATGG AGGATGCAAA AGTTACCTAT GAATTGGGTA

1381 AGGAATTTCT TCCAATGGAG GCGCAGCTGT CGAGATTAAT AGGGCAGAGC CTGTGGGACG

1441 TGTCTCGAAG TTCAACGGGA AACCTCGTCG AATGGTTTCT GTTGCGGAAA GCATACGAGC

1501 GTAATGAACT TGCCCCTAAC AAACCGGATG AAAAGGAGCT GGCACGCCGT CGCCAATCCT

1561 ATGAAGGCGG TTACGTTAAA GAACCAGAGC GGGGGTTATG GGAAAATATC GTGTATCTGG

1621 ATTTCCGTTC GCTCTACCCG AGCATTATCA TTACCCACAA CGTATCTCCC GACACTTTGA

1681 ATCGCGAGGG CTGTAAAGAA TATGATGTCG CGCCGCAGGT TGGTCATAGA TTTTGCAAGG

1741 ACTTCCCGGG ATTTATACCA AGTCTGCTTG GCGATTTACT GGAAGAGCGA CAAAAAATCA

1801 AAAGAAAAT GAAAGCTACA ATCGATCCGA TAGAACGTAA GCTGCTCGAC TACCGCCAGC

1861 GGGCCATCAA AATTTTGGCA AACTCATATT ATGGTTACTA TGGGTACGCG CGTGCTCGCT

1921 GGTATTGTAA AGAGTGCGCC GAATCCGTGA CGGCATGGGG CCGTGAATAC ATCACCATGA

1981 CTATTAAGGA GATAGAAGAG AAATATGGTT TCAAAGTAAT CTACTCGGAT ACAGACGGAT

2041 TCTTTGCGAC GATTCCCGGT GCCGATGCAG AAACCGTCAA GAAAAAAGCG ATGGAATTCC

2101 TTAAGTATAT AAATGCTAAA TTACCTGGTG CCCTGGAGCT GGAATACGAA GGGTTTTACA

2161 AACGCGGATT CTTTGTTACT AAGAAAAAAT ATGCGGTGAT CGACGAGGAA GGCAAGATTA

2221 CGACCAGAGG CCTCGAGATT GTACGGCGTG ATTGGAGCGA AATCGCTAAA GAAACACAGG

2281 CACGTGTCTT GGAGGCATTA CTGAAAGATG GGGACGTTGA AAAGGCGGTG CGAATTGTAA

2341 AAGAAGTCAC CGAAAAACTT TCTAAGTACG AAGTTCCGCC AGAGAAACTG GTGATACACG

2401 AACAAATCAC TCGTGATCTG AAAGACTATA AGGCTACAGG CCCGCATGTA GCAGTCGCCA

2461 AACGCCTCGC GGCTCGGGGT GTTAAAATTC GTCCCGGAAC GGTGATCAGT TACATTGTAT

2521 TGAAGGGCTC AGGTCGCATA GGGGATAGAG CAATCCCTTT CGACGAGTTT GATCCAACCA

2581 AACACAAATA TGATGCCGAA TACTATATTG AAAACCAGGT CTTGCCGGCG GTTGAGCGTA

2641 TACTGCGCGC TTTCGGCTAT CGAAAGGAAG ATCTTCGTTA CCAAAAAACT AGACAGGTGG

2701 GTCTGTCCGC ATGGCTCAAA CCTAAGGGAA CGTAATGATA TGAGACCGGA TCCTCTAGAG

2761 TCGACCTGCA GGCATGCAAG CTTGGCGTAA TCATGGTCAT AGCTGTTTCC TGTGTGAAAT

2821 TGTTATCCGC TCACAATTCC ACACAACATA CGAGCCGGAA GCATAAAGTG TAAAGCCTGG

2881 GGTGCCTAAT GAGTGAGCTA ACTCACATTA ATTGCGTTGC GCTCACTGCC CGCTTTCCAG

2941 TCGGGAAACC TGTCGTGCCA GCTGCATTAA TGAATCGGCC AACGCGCGGG GAGAGGCGGT

3001 TTGCGTATTG GGCGCTCTTC CGCTTCCTCG CTCACTGACT CGCTGCGCTC GGTCGTTCGG

3061 CTGCGGCGAG CGGTATCAGC TCACTCAAAG GCGGTAATAC GGTTATCCAC AGAATCAGGG

3121 GATAACGCAG GAAAGAACAT GTGAGCAAAA GGCCAGCAAA AGGCCAGGAA CCGTAAAAAG

3181 GCCGCGTTGC TGGCGTTTTT CCATAGGCTC CGCCCCCCTG ACGAGCATCA CAAAAATCGA

3241 CGCTCAAGTC AGAGGTGGCG AAACCCGACA GGACTATAAA GATACCAGGC GTTTCCCCCT
```

TABLE 8-continued

Sequences

```
3301 GGAAGCTCCC TCGTGCGCTC TCCTGTTCCG ACCCTGCCGC TTACCGGATA CCTGTCCGCC

3361 TTTCTCCCTT CGGGAAGCGT GGCGCTTTCT CATAGCTCAC GCTGTAGGTA TCTCAGTTCG

3421 GTGTAGGTCG TTCGCTCCAA GCTGGGCTGT GTGCACGAAC CCCCGTTCA GCCCGACCGC

3481 TGCGCCTTAT CCGGTAACTA TCGTCTTGAG TCCAACCCGG TAAGACACGA CTTATCGCCA

3541 CTGGCAGCAG CCACTGGTAA CAGGATTAGC AGAGCGAGGT ATGTAGGCGG TGCTACAGAG

3601 TTCTTGAAGT GGTGGCCTAA CTACGGCTAC ACTAGAAGAA CAGTATTTGG TATCTGCGCT

3661 CTGCTGAAGC CAGTTACCTT CGGAAAAAGA GTTGGTAGCT CTTGATCCGG CAAACAAACC

3721 ACCGCTGGTA GCGGTGGTTT TTTTGTTTGC AAGCAGCAGA TTACGCGCAG AAAAAAGGA

3781 TCTCAAGAAG ATCCTTTGAT CTTTTCTACG GGGTCTGACG CTCAGTGGAA CGAAAACTCA

3841 CGTTAAGGGA TTTTGGTCAT GAGATTATCA AAAAGGATCT TCACCTAGAT CCTTTTAAAT

3901 TAAAAATGAA GTTTTAAATC AATCTAAAGT ATATATGAGT AAACTTGGTC TGACAGTTAC

3961 CAATGCTTAA TCAGTGAGGC ACCTATCTCA GCGATCTGTC TATTTCGTTC ATCCATAGTT

4021 GCCTGACTCC CCGTCGTGTA GATAACTACG ATACGGGAGG GCTTACCATC TGGCCCCAGT

4081 GCTGCAATGA TACCGCGAGA CCCACGCTCA CCGGCTCCAG ATTTATCAGC AATAAACCAG

4141 CCAGCCGGAA GGGCCGAGCG CAGAAGTGGT CCTGCAACTT TATCCGCCTC CATCCAGTCT

4201 ATTAATTGTT GCCGGGAAGC TAGAGTAAGT AGTTCGCCAG TTAATAGTTT GCGCAACGTT

4261 GTTGCCATTG CTACAGGCAT CGTGGTGTCA CGCTCGTCGT TTGGTATGGC TTCATTCAGC

4321 TCCGGTTCCC AACGATCAAG GCGAGTTACA TGATCCCCCA TGTTGTGCAA AAAAGCGGTT

4381 AGCTCCTTCG GTCCTCCGAT CGTTGTCAGA AGTAAGTTGG CCGCAGTGTT ATCACTCATG

4441 GTTATGGCAG CACTGCATAA TTCTCTTACT GTCATGCCAT CCGTAAGATG CTTTTCTGTG

4501 ACTGGTGAGT ACTCAACCAA GTCATTCTGA GAATAGTGTA TGCGGCGACC GAGTTGCTCT

4561 TGCCCGGCGT CAATACGGGA TAATACCGCG CCACATAGCA GAACTTTAAA AGTGCTCATC

4621 ATTGGAAAAC GTTCTTCGGG GCGAAAACTC TCAAGGATCT TACCGCTGTT GAGATCCAGT

4681 TCGATGTAAC CCACTCGTGC ACCCAACTGA TCTTCAGCAT CTTTTACTTT CACCAGCGTT

4741 TCTGGGTGAG CAAAAACAGG AAGGCAAAAT GCCGCAAAAA AGGGAATAAG GCGACACGG

4801 AAATGTTGAA TACTCATACT CTTCCTTTTT CAATATTATT GAAGCATTTA TCAGGGTTAT

4861 TGTCTCATGA GCGGATACAT ATTTGAATGT ATTTAGAAAA ATAAACAAAT AGGGGTTCCG

4921 CGCACATTTC CCCGAAAAGT GCCACCTGAC GTCTAAGAAA CCATTATTAT CATGACATTA

4981 ACCTATAAAA ATAGGCGTAT CACGAGGCCC TTTCGTC
```

Amino acid sequences of Pfu and KOD

Sequence 9

(SEQ ID NO: 9)
>Pfu amino acid sequence

```
  1 MILDVDYITE EGKPVIRLFK KENGKFKIEH DRTFRPYIYA LLRDDSKIEE VKKITGERHG

61 KIVRIVDVEK VEKKFLGKPI TVWKLYLEHP QDVPTIREKV REHPAVVDIF EYDIPFAKRY

121 LIDKGLIPME GEEELKILAF DIETLYHEGE EFGKGPIIMI SYADENEAKV ITWKNIDLPY

181 VEVVSSEREM IKRFLRIIRE KDPDIIVTYN GDSFDFPYLA KRAEKLGIKL TIGRDGSEPK

241 MQRIGDMTAV EVKGRIHFDL YHVITRTINL PTYTLEAVYE AIFGKPKEKV YADEIAKAWE

301 SGENLERVAK YSMEDAKATY ELGKEFLPME IQLSRLVGQP LWDVSRSSTG NLVEWFLLRK

361 AYERNEVAPN KPSEEEYQRR LRESYTGGFV KEPEKGLWEN IVYLDFRALY PSIIITHNVS
```

TABLE 8-continued

Sequences

```
421 PDTLNEGCK NYDIAPQVGH KFCKDIPGFI PSLLGHLLEE RQKIKTKMKE TQDPIEKILL

481 DYRQKAIKLL ANSFYGYYGY AKARWYCKEC AESVTAWGRK YIELVWKELE EKFGFKVLYI

541 DTDGLYATIP GGESEEIKKK ALEFVKYINS KLPGLLELEY EGFYKRGFFV TKKRYAVIDE

601 EGKVITRGLE IVRRDWSEIA KETQARVLET ILKHGDVEEA VRIVKEVIQK LANYEIPPEK

661 LAIYEQITRP LHEYKAIGPH VAVAKKLAAK GVKIKPGMVI GYIVLRGDGP ISNRAILAEE

721 YDPKKHKYDA EYYIENQVLP AVLRILEGFG YRKEDLRYQK TRQVGLTSWL NIKKS*
```

Sequence 10                                                             (SEQ ID NO: 10)
>Pfu amino acid sequence, extra 3 aa in 5' area.
```
  1 MASAILDVDY ITEEGKPVIR LFKKENGKFK IEHDRTFRPY IYALLRDDSK IEEVKKITGE

61 RHGKIVRIVD VEKVEKKFLG KPITVWKLYL EHPQDVPTIR EKVREHPAVV DIFEYDIPFA

121 KRYLIDKGLI PMEGEEELKI LAFDIETLYH EGEEFGKGPI IMISYADENE AKVITWKNID

181 LPYVEVVSSE REMIKRFLRI IREKDPDIIV TYNGDSFDFP YLKKRCEKLG IKLTIGRDGS

241 EPKMQRIGDM TAVEVKGRIH FDLYHVITRT INLPTYTLEA VYEAIFGKPK EKVYADEIAK

301 AWESGENLER VAKYSMEDAK ATYELGKEFL PMEIQLSRLV GQPLWDVSRS STGNLVEWFL

361 LRKAYERNEV APNKPSEEEY QRRLRESYTG GFVKEPEKGL WENIVYLDFR ALYPSIIITH

421 NVSPDTLNLE GCKNYDIAPQ VGHKFCKDIP GFIPSLLGHL LEERQKIKTK MKETQDPIEK

481 ILLDYRQKAI KLLANSFYGY YGYAKARWYC KECAESVTAW GRKYIELVWK ELEEKFGFKV

541 LYIDTDGLYA TIPGGESEEI KKKALEFVKY INSKLPGLLE LEYEGFYKRG FFVTKKRYAV

601 IDEEGKVITR GLEIVRRDWS EIAKETQARV LETILKHGDV EEAVRIVKEV IQKLANYEIP

661 PEKLAIYEQI TRPLHEYKAI GPHVAVAKKL AAKGVKIKPG MVIGYIVLRG DGPISNRAIL

721 AEEYDPKKHK YDAEYYIENQ VLPAVLRILE GFGYRKEDLR YQKTRQVGLT SWLNIKKS*
```

Sequence 11                                                             (SEQ ID NO: 11)
>KOD amino acid sequence
```
  1 MILDTDYITE DGKPVIRIFK KENGEFKIEY DRTFEPYFYA LLKDDSAIEE VKKITAERHG

61 TVVTVKRVEK VQKKFLGRPV EVWKLYFTHP QDVPAIRDKI REHPAVIDIY EYDIPFAKRY

121 LIDKGLVPME GDEELKMLAF DIETLYHEGE EFAEGPILMI SYADEEGARV ITWKNVDLPY

181 VDVVSTEREM IKRFLVVKE KDPDVLITYN GDNFDFAYLK KRCEKLGINF ALGRDGSEPK

241 IQRMGDRFAV EVKGRIHFDL YPVIRRTINL PTYTLEAVYE AVFGQPKEKV YAEEITTAWE

301 TGENLERVAR YSMEDAKVTY ELGKEFLPME AQLSRLIGQS LWDVSRSSTG NLVEWFLLRK

361 AYERNELAPN KPDEKELARR RQSYEGGYVK EPERGLWENI VYLDFRSLYP SIIITHNVSP

421 DTLNREGCKE YDVAPQVGHR FCKDFPGFIP SLLGDLLEER QKIKKKMKAT IDPIERKLLD

481 YRQRAIKILA NSYYGYYGYA RARWYCKECA ESVTAWGREY ITMTIKEIEE KYGFKVIYSD

541 TDGFFATIPG ADAETVKKKA MEFLKYINAK LPGALELEYE GFYKRGFFVT KKKYAVIDEE

601 GKITTRGLEI VRRDWSEIAK ETQARVLEAL LKDGDVEKAV RIVKEVTEKL SKYEVPPEKL

661 VIHEQITRDL KDYKATGPHV AVAKRLAARG VKIRPGTVIS YIVLKGSGRI GDRAIPFDEF

721 DPTKHKYDAE YYIENQVLPA VERILRAFGY RKEDLRYQKT RQVGLSAWLK PKGT
```

Sequence 12                                                             (SEQ ID NO: 12)
>KOD amino acid sequence, extra 3 aa in 5' area.
```
  1 MASAILDTDY ITEDGKPVIR IFKKENGEFK IEYDRTFEPY FYALLKDDSA IEEVKKITAE

61 RHGTVVTVKR VEKVQKKFLG RPVEVWKLYF THPQDVPAIR DKIREHPAVI DIYEYDIPFA

121 KRYLIDKGLV PMEGDEELKM LAFDIETLYH EGEEFAEGPI LMISYADEEG ARVITWKNVD
```

TABLE 8-continued

Sequences

```
181 LPYVDVVSTE REMIKRFLRV VKEKDPDVLI TYNGDNFDFA YLKKRCEKLG INFALGRDGS

241 EPKIQRMGDR FAVEVKGRIH FDLYPVIRRT INLPTYTLEA VYEAVFGQPK EKVYAEEITT

301 AWETGENLER VARYSMEDAK VTYELGKEFL PMEAQLSRLI GQSLWDVSRS STGNLVEWFL

361 LRKAYERNEL APNKPDEKEL ARRRQSYEGG YVKEPERGLW ENIVYLDFRS LYPSIIITHN

421 VSPDTLNREG CKEYDVAPQV GHRFCKDFPG FIPSLLGDLL EERQKIKKKM KATIDPIERK

481 LLDYRQRAIK ILANSYYGYY GYARARWYCK ECAESVTAWG REYITMTIKE IEEKYGFKVI

541 YSDTDGFFAT IPGADAETVK KKAMEFLKYI NAKLPGALEL EYEGFYKRGF FVTKKKYAVI

601 DEEGKITTRG LEIVRRDWSE IAKETQARVL EALLKDGDVE KAVRIVKEVT EKLSKYEVPP

661 EKLVIHEQIT RDLKDYKATG PHVAVAKRLA ARGVKIRPGT VISYIVLKGS GRIGDRAIPF

721 DEFDPTKHKY DAEYYIENQV LPAVERILRA FGYRKEDLRY QKTRQVGLSA WLKPKGT*
```

DNA sequences of chimeras Pod and Kofu

Sequence 13

(SEQ ID NO: 13)

>Pod codon optimized nucleotide sequence

```
   1 ATGGCTAGCG CCATTCTGGA TGTGGACTAT ATCACCGAAG AGGGCAAACC GGTTATACGT

61 TTATTTAAGA AAGAGAATGG TAAATTCAAG ATCGAGCATG ACCGCACGTT CCGTCCATAC

121 ATTTACGCGT TGCTTCGGGA TGATAGCAAA ATTGAGGAAG TCAAAAAGAT CACCGGGGAA

181 CGTCATGGAA AATAGTAAG AATTGTGGAC GTTGAAAAAG TCGAAAAGAA ATTTCTGGGC

241 AAACCGATCA CTGTATGGAA GCTCTATCTG AACATCCTC AGGATGTGCC CACAATTCGA

301 GAAAAAGTTC GTGAGCACCC AGCCGTCGTG GATATATTTG AATATGACAT CCCTTTTGCA

361 AAACGCTACT TAATTGATAA AGGCCTGATC CCGATGGAGG GGGAAGAAGA ACTTAAAATT

421 CTGGCTTTTG ACATAGAAAC GCTCTATCAT GAGGGAGAAG AATTTGGCAA AGGTCCCATC

481 ATTATGATTT CTTACGCGGA TGAGAACGAA GCCAAGGTAA TCACTTGGAA AAATATTGAC

541 CTGCCGTACG TTGAAGTGGT CAGTTCAGAG CGGGAAATGA TTAAACGTTT TTTACGCATC

601 ATTAGAGAGA AAGATCCAGA TATAATCGTT ACATATAACG GCGACTCCTT CGATTTTCCT

661 TACCTGGCAA AACGAGCTGA AAAATTGGGT ATTAAACTTA CCATCGGGCG TGACGGATCG

721 GAACCGAAAA TGCAACGCAT TGGCGATATG ACGGCGGTAG AGGTGAAAGG TCGGATACAC

781 TTTGATCTGT ATCATGTCAT CACCCGTACT ATTAATCTCC CCACATACAC GTTAGAAGCC

841 GTTTATGAGG CAATATTCGG CAAGCCGAAA GAAAAAGTGT ACGCTGACGA AATCGCGAAG

901 GCATGGGAGA GCGGCGAAAA CCTGGAGCGC GTAGCAAAAT ATTCTATGGA AGATGCTAAA

961 GCGACCTACG AATTGGGGAA AGAATTTCTT CCAATGGAAA TTCAGCTGTC GAGATTAATA

1021 GGGCAGAGCC TGTGGGACGT GTCTCGAAGT TCAACGGGAA ACCTCGTCGA ATGGTTTCTG

1081 TTGCGGAAAG CATACGAGCG TAATGAACTT GCCCCTAACA AACCGGATGA AAAGGAGCTG

1141 GCACGCCGTC GCCAATCCTA TGAAGGCGGT TACGTTAAAG AACCAGAGCG GGGGTTATGG

1201 GAAAATATCG TGTATCTGGA TTTCCGTTCG CTCTACCCGA GCATTATCAT TACCCACAAC

1261 GTATCTCCCG ACACTTTGAA TCGCGAGGGC TGTAAGAAT ATGATGTCGC GCCGCAGGTT

1321 GGTCATAGAT TTTGCAAGGA CTTCCCGGGA TTTATACCAA GTCTGCTTGG CGATTTACTG

1381 GAAGAGCGAC AAAAAATCAA AAAGAAAATG AAAGCTACAA TCGATCCGAT AGAACGTAAG

1441 CTGCTCGACT ACCGCCAGCG GGCCATCAAA ATTTTGGCAA ACTCATATTA TGGTTACTAT

1501 GGGTACGCGC GTGCTCGCTG GTATTGTAAA GAGTGCGCCG AATCCGTGAC GGCATGGGGC
```

TABLE 8-continued

Sequences

```
1561 CGTGAATACA TCACCATGAC TATTAAGGAG ATAGAAGAGA AATATGGTTT CAAAGTAATC

1621 TACTCGGATA CAGACGGATT CTTTGCGACG ATTCCCGGTG CCGATGCAGA AACCGTCAAG

1681 AAAAAAGCGA TGGAATTCGT TAAGTACATT AATAGTAAAT TACCGGGACT GCTTGAACTG

1741 GAGTATGAAG GCTTCTACAA AAGAGGTTTT TTCGTTACTA AGAAACGATA TGCCGTAATA

1801 GATGAAGAGG GGAAAGTCAT CACACGTGGC CTCGAGATTG TTCGCCGGGA CTGGTCAGAG

1861 ATAGCAAAGG AAACGCAGGC GCGCGTGCTC GAAACCATCT TGAAACATGG TGATGTAGAG

1921 GAAGCCGTCC GCATTGTTAA AGAGGTGATC CAGAAGTTAG CAAACTATGA AATTCCACCG

1981 GAAAAACTGG CGATATACGA GCAAATCACT CGTCCCCTTC ACGAATATAA AGCTATTGGA

2041 CCTCATGTAG CCGTCGCGAA GAAACTGGCT GCAAAAGGCG TTAAGATAAA ACCAGGTATG

2101 GTGATCGGGT ACATTGTACT CCGCGGCGAC GGTCCGATTT CCAATAGAGC CATCTTGGCG

2161 GAGGAATATG ATCCTAAAAA GCATAAATAC GACGCTGAAT ATTACATTGA GAACCAGGTC

2221 TTGCCGGCAG TTCTGCGGAT ACTTGAAGGA TTTGGCTATC GTAAGAAGA TCTGCGCTAT

2281 CAAAAGACGC GACAGGTGGG TCTGACTAGC TGGTTGAATA TCAAAAAATC GTAA
```

Sequence 14
(SEQ ID NO: 14)
>Kofu codon optimized nucleotide sequence
```
   1 ATGGCTAGCG CCATTCTGGA TACCGACTAT ATCACGGAAG ATGGCAAACC GGTGATACGT

61 ATTTTTAAGA AGAGAATGG TGAGTTCAAA ATCGAGTACG ACCGCACTTT TGAGCCATAT

121 TTCTACGCGT TACTGAAGGA CGATAGCGCC ATTGAAGAAG TTAAAAAAAT CACCGCAGAG

181 CGGCATGGGA CAGTGGTAAC CGTGAAGAGA GTTGAAAAAG TCCAGAAAAA ATTTTTGGGA

241 CGACCTGTAG AAGTGTGGAA ACTTTATTTC ACTCACCCCC AAGATGTTCC GGCTATACGT

301 GATAAAATTC GCGAACATCC AGCGGTCATT GATATTTACG AATATGATAT ACCTTTTGCC

361 AAGCGTTACC TCATCGACAA AGGCCTGGTG CCGATGGAAG GTGATGAAGA ATTAAAAATG

421 TTGGCATTCG ACATTGAAAC ACTTTATCAC GAGGGGAAG AGTTTGCTGA GGGTCCCATC

481 CTGATGATTT CTTATGCGGA TGAAGAGGGT GCCCGCGTAA TAACCTGGAA GAACGTTGAT

541 CTCCCGTACG TGGACGTCGT TAGTACGGAA CGGGAAATGA TCAAACGTTT CCTGCGCGTA

601 GTGAAAGAGA AGATCCAGA CGTCTTAATT ACCTATAATG GTGATAACTT TGATTTTGCA

661 TACCTGAAAA AAGATGCGA AAAGTTGGGC ATAAATTTCG CTCTTGGTCG AGACGGGTCA

721 GAGCCTAAAA TCCAGCGTAT GGGAGATCGC TTTGCGGTTG AAGTGAAAGG CCGGATTCAT

781 TTCGACCTGT ATCCGGTAAT TCGTCGCACT ATCAACCTCC CCACATACAC GTTAGAAGCC

841 GTCTATGAGG CAGTTTTTGG TCAACCGAAG GAAAAAGTTT ACGCTGAGGA AATTACCACT

901 GCGTGGGAAA CAGGCGAGAA TCTGGAACGT GTAGCCCGCT ATTCTATGGA GGATGCAAAA

961 GTTACCTATG AATTGGGTAA GGAATTTCTT CCAATGGAGG CGCAGCTGAG TCGTTTAGTC

1021 GGACAACCTC TGTGGGACGT TCACGCTCC TCGACTGGCA ATCTCGTGGA GTGGTTCCTG

1081 TTGAGAAAAG CCTATGAACG AAACGAAGTA GCACCGAATA AACCAAGCGA GGAAGAATAT

1141 CAGCGTCGCC TTCGCGAGTC TTACACAGGT GGGTTTGTTA AGGAACCGGA GAAAGGTCTT

1201 TGGGAAAACA TCGTGTATTT AGATTTCCGT GCGCTGTACC CCAGTATTAT AATCACCCAC

1261 AATGTCTCAC CTGACACGCT CAACTTGGAA GGTTGCAAAA ATTATGATAT TGCTCCGCAA

1321 GTTGGACATA AGTTTTGTAA AGATATTCCG GGCTTCATCC CGTCCCTGCT TGGTCACTTA

1381 CTGGAAGAGC GCCAAAAAAT TAAGACCAAA ATGAAAGAGA CTCAGGATCC CATTGAAAAG

1441 ATCCTGCTCG ATTACCGGCA AAAAGCCATT AAATTGCTTG CAAACTCGTT TTATGGGTAC
```

TABLE 8-continued

Sequences

```
1501 TATGGCTATG CGAAGGCTCG TTGGTACTGC AAAGAATGTG CCGAGAGCGT GACAGCATGG

1561 GGTCGCAAAT ATATAGAATT AGTATGGAAG GAGCTGGAAG AAAAATTCGG ATTCAAAGTC

1621 CTGTACATCG ATACGGATGG CCTCTATGCG ACCATTCCTG GTGGGGAGTC TGAAGAAATC

1681 AAGAAAAAAG CCTTGGAATT CCTTAAGTAT ATAAATGCTA AATTACCTGG TGCCCTGGAG

1741 CTGGAATACG AAGGGTTTTA CAAACGCGGA TTCTTTGTTA CTAAGAAAAA ATATGCGGTG

1801 ATCGACGAGG AAGGCAAGAT TACGACCAGA GGCCTCGAGA TTGTACGGCG TGATTGGAGC

1861 GAAATCGCTA AGAAACACA GGCACGTGTC TTGGAGGCAT TACTGAAAGA TGGGGACGTT

1921 GAAAAGGCGG TGCGAATTGT AAAGAAGTC ACCGAAAAAC TTTCTAAGTA CGAAGTTCCG

1981 CCAGAGAAAC TGGTGATACA CGAACAAATC ACTCGTGATC TGAAAGACTA TAAGGCTACA

2041 GGCCCGCATG TAGCAGTCGC CAAACGCCTC GCGGCTCGGG GTGTTAAAAT TCGTCCCGGA

2101 ACGGTGATCA GTTACATTGT ATTGAAGGGC TCAGGTCGCA TAGGGGATAG AGCAATCCCT

2161 TTCGACGAGT TTGATCCAAC CAAACACAAA TATGATGCCG AATACTATAT TGAAAACCAG

2221 GTCTTGCCGG CGGTTGAGCG TATACTGCGC GCTTTCGGCT ATCGAAAGGA AGATCTTCGT

2281 TACCAAAAAA CTAGACAGGT GGGTCTGTCC GCATGGCTCA AACCTAAGGG AACGTAA
```

Amino acid sequences of chimeras Pod and Kofu

Sequence 15

(SEQ ID NO: 15)

>Pod amino acid sequence

```
  1 MASAILDVDY ITEEGKPVIR LFKKENGKFK IEHDRTFRPY IYALLRDDSK IEEVKKITGE

61 RHGKIVRIVD VEKVEKKFLG KPITVWKLYL EHPQDVPTIR EKVREHPAVV DIFEYDIPFA

121 KRYLIDKGLI PMEGEEELKI LAFDIETLYH EGEEFGKGPI IMISYADENE AKVITWKNID

181 LPYVEVVSSE REMIKRFLRI IREKDPDIIV TYNGDSFDFP YLAKRAEKLG IKLTIGRDGS

241 EPKMQRIGDM TAVEVKGRIH FDLYHVITRT INLPTYTLEA VYEAIFGKPK EKVYADEIAK

301 AWESGENLER VAKYSMEDAK ATYELGKEFL PMEIQLSRLI GQSLWDVSRS STGNLVEWFL

361 LRKAYERNEL APNKPDEKEL ARRRQSYEGG YVKEPERGLW ENIVYLDFRS LYPSIIITHN

421 VSPDTLNREG CKEYDVAPQV GHRFCKDFPG FIPSLLGDLL EERQKIKKKM KATIDPIERK

481 LLDYRQRAIK ILANSYYGYY GYARARWYCK ECAESVTAWG REYITMTIKE IEEKYGFKVI

541 YSDTDGFFAT IPGADAETVK KKAMEFVKYI NSKLPGLLEL EYEGFYKRGF FVTKKRYAVI

601 DEEGKVITRG LEIVRRDWSE IAKETQARVL ETILKHGDVE EAVRIVKEVI QKLANYEIPP

661 EKLAIYEQIT RPLHEYKAIG PHVAVAKKLA AKGVKIKPGM VIGYIVLRGD GPISNRAILA

721 EEYDPKKHKY DAEYYIENQV LPAVLRILEG FGYRKEDLRY QKTRQVGLTS WLNIKKS*
```

Sequence 16

(SEQ ID NO: 16)

>Kofu amino acid sequence

```
  1 MASAILDTDY ITEDGKPVIR IFKKENGEFK IEYDRTFEPY FYALLKDDSA IEEVKKITAE

61 RHGTVVTVKR VEKVQKKFLG RPVEVWKLYF THPQDVPAIR DKIREHPAVI DIYEYDIPFA

121 KRYLIDKGLV PMEGDEELKM LAFDIETLYH EGEEFAEGPI LMISYADEEG ARVITWKNVD

181 LPYVDVVSTE REMIKRFLRV VKEKDPDVLI TYNGDNFDFA YLKKRCEKLG INFALGRDGS

241 EPKIQRMGDR FAVEVKGRIH FDLYPVIRRT INLPTYTLEA VYEAVFGQPK EKVYAEEITT

301 AWETGENLER VARYSMEDAK VTYELGKEFL PMEAQLSRLV GQPLWDVSRS STGNLVEWFL

361 LRKAYERNEV APNKPSEEEY QRRLRESYTG GFVKEPEKGL WENIVYLDFR ALYPSIIITH

421 NVSPDTLNLE GCKNYDIAPQ VGHKFCKDIP GFIPSLLGHL LEERQKIKTK MKETQDPIEK
```

TABLE 8-continued

Sequences

481 ILLDYRQKAI KLLANSFYGY YGYAKARWYC KECAESVTAW GRKYIELVWK ELEEKFGFKV

541 LYIDTDGLYA TIPGGESEEI KKKALEFLKY INAKLPGALE LEYEGFYKRG FFVTKKKYAV

601 IDEEGKITTR GLEIVRRDWS EIAKETQARV LEALLKDGDV EKAVRIVKEV TEKLSKYEVP

661 PEKLVIHEQI TRDLKDYKAT GPHVAVAKRL AARGVKIRPG TVISYIVLKG SGRIGDRAIP

721 FDEFDPTKHK YDAEYYIENQ VLPAVERILR AFGYRKEDLR YQKTRQVGLS AWLKPKGT*

Sequence 17
(SEQ ID NO: 17)
>pLACIQZa
   1 TCGCGCGTTTCGGTGATGACGGTGAAAACCTCTGACACATGCAGCTCCCGGAGACGGTCA

61 CAGCTTGTCTGTAAGCGGATGCCGGGAGCAGACAAGCCCGTCAGGGCGCGTCAGCGGGTG

121 TTGGCGGGTGTCGGGGCTGGCTTAACTATGCGGCATCAGAGCAGATTGTACTGAGAGTGC

181 ACCATATGCGGTGTGAAATACCGCACAGATGCGTAAGGAGAAAATACCGCATCAGGCGCC

241 ATTCGCCATTCAGGCTGCGCAACTGTTGGGAAGGGCGATCGGTGCGGGCCTCTTCGCTAT

GT
 301 TACGCCAGCTGGCGAAAGGGGGATGTGCTGCAAGGCGATTAAGTTGGGTAACGCCAGGGT

TTTCCCAGTCACGAC >>> Primer M13-40 (SEQ ID NO: 24)
 361 TTTCCCAGTCACGACGTTGTAAAACGACGGCCAGTGAATTCGAGCTCGGTACCCGGGGAT XbaI
 421 CCTCTAGAGCCGTAATCATGGTCATAGCTGTTTCCTGTGTGAAATTGTTATCCGCTCACA

481 ATTCCACACAACATACGAGCCGGAAGCATAAAGTGTAAAGCCTGGGGTGCCTAATGAGTG

541 AGCTAACTCACATTAATTGCGTTGCGCTCACTGCCCGCTTTCCAGTCGGGAAACCTGTCG

601 TGCCAGCTGCATTAATGAATCGGCCAACGCGCGGGGAGAGGCGGTTTGCGTATTGGGCGC

661 CAGGGTGGTTTTTCTTTTCACCAGTGAGACGGGCAACAGCTGATTGCCCTTCACCGCCTG

721 GCCCTGAGAGAGTTGCAGCAAGCGGTCCACGCTGGTTTGCCCCAGCAGGCGAAAATCCTG

781 TTTGATGGTGGTTGACGGCGGGATATAACATGAGCTGTCTTCGGTATCGTCGTATCCCAC

841 TACCGAGATATCCGCACCAACGCGCAGCCCGGACTCGGTAATGGCGCGCATTGCGCCCAG

901 CGCCATCTGATCGTTGGCAACCAGCATCGCAGTGGGAACGATGCCCTCATTCAGCATTTG

961 CATGGTTTGTTGAAAACCGGACATGGCACTCCAGTCGCCTTCCCGTTCCGCTATCGGCTG

1021 AATTTGATTGCGAGTGAGATATTTATGCCAGCCAGCCAGACGCAGACGCGCCGAGACAGA

1081 ACTTAATGGGCCCGCTAACAGCGCGATTTGCTGGTGACCCAATGCGACCAGATGCTCCAC

1141 GCCCAGTCGCGTACCGTCTTCATGGGAGAAAATAATACTGTTGATGGGTGTCTGGTCAGA

1201 GACATCAAGAAATAACGCCGGAACATTAGTGCAGGCAGCTTCCACAGCAATGGCATCCTG

1261 GTCATCCAGCGGATAGTTAATGATCAGCCCACTGACGCGTTGCGCGAGAAGATTGTGCAC

1321 CGCCGCTTTACAGGCTTCGACGCCGCTTCGTTCTACCATCGACACCACCACGCTGGCACC

1381 CAGTTGATCGGCGCGAGATTTAATCGCCGCGACAATTTGCGACGGCGCGTGCAGGGCCAG

1441 ACTGGAGGTGGCAACGCCAATCAGCAACGACTGTTTGCCCGCCAGTTGTTGTGCCACGCG

1501 GTTGGGAATGTAATTCAGCTCCGCCATCGCCGCTTCCACTTTTTCCCGCGTTTTCGCAGA

1561 AACGTGGCTGGCCTGGTTCACCACGCGGGAAACGGTCTGATAAGAGACACCGGCATACTC

1621 TGCGACATCGTATAACGTTACTGGTTTCACATTCACCACCCTGAATTGACTCTCTTCCGG

1681 GCGCTATCATGCCATACCGCGAAAGGTTTTGCGCCATTCGATGGTGTCAACGTAAATGCA

NcoI
1741 TGCCGCTTCGCCTTCCGGCCACCAGAATAGCCTGCGCCATGGGCTTCCTCGCTCACTGAC

TABLE 8-continued

Sequences

```
1801 TCGCTGCGCTCGGTCGTTCGGCTGCGGCGAGCGGTATCAGCTCACTCAAAGGCGGTAATA

1861 CGGTTATCCACAGAATCAGGGGATAACGCAGGAAAGAACATGTGAGCAAAAGGCCAGCAA

1921 AAGGCCAGGAACCGTAAAAAGGCCGCGTTGCTGGCGTTTTTCCATAGGCTCCGCCCCCCT

1981 GACGAGCATCACAAAAATCGACGCTCAAGTCAGAGGTGGCGAAACCCGACAGGACTATAA

PRIMER PKBLACIR <<< GCTGTCCTGATATT
          TCTATGG (SEQ ID NO: 25)

2041 AGATACCAGGCGTTTCCCCCTGGAAGCTCCCTCGTGCGCTCTCCTGTTCCGACCCTGCCG

2101 CTTACCGGATACCTGTCCGCCTTTCTCCCTTCGGGAAGCGTGGCGCTTTCTCATAGCTCA

2161 CGCTGTAGGTATCTCAGTTCGGTGTAGGTCGTTCGCTCCAAGCTGGGCTGTGTGCACGAA

2221 CCCCCCGTTCAGCCCGACCGCTGCGCCTTATCCGGTAACTATCGTCTTGAGTCCAACCCG

2281 GTAAGACACGACTTATCGCCACTGGCAGCAGCCACTGGTAACAGGATTAGCAGAGCGAGG

2341 TATGTAGGCGGTGCTACAGAGTTCTTGAAGTGGTGGCCTAACTACGGCTACACTAGAAGA

2401 ACAGTATTTGGTATCTGCGCTCTGCTGAAGCCAGTTACCTTCGGAAAAAGAGTTGGTAGC

2461 TCTTGATCCGGCAAACAAACCACCGCTGGTAGCGGTGGTTTTTTTGTTTGCAAGCAGCAG

2521 ATTACGCGCAGAAAAAAAGGATCTCAAGAAGATCCTTTGATCTTTTCTACGGGGTCTGAC

2581 GCTCAGTGGAACGAAAACTCACGTTAAGGGATTTTGGTCATGAGATTATCAAAAAGGATC

2641 TTCACCTAGATCCTTTTAAATTAAAAATGAAGTTTTAAATCAATCTAAAGTATATATGAG

2701 TAAACTTGGTCTGACAGTTACCAATGCTTAATCAGTGAGGCACCTATCTCAGCGATCTGT

2761 CTATTTCGTTCATCCATAGTTGCCTGACTCCCCGTCGTGTAGATAACTACGATACGGGAG

2821 GGCTTACCATCTGGCCCCAGTGCTGCAATGATACCGCGAGACCCACGCTCACCGGCTCCA

2881 GATTTATCAGCAATAAACCAGCCAGCCGGAAGGGCCGAGCGCAGAAGTGGTCCTGCAACT

2941 TTATCCGCCTCCATCCAGTCTATTAATTGTTGCCGGGAAGCTAGAGTAAGTAGTTCGCCA

3001 GTTAATAGTTTGCGCAACGTTGTTGCCATTGCTACAGGCATCGTGGTGTCACGCTCGTCG

3061 TTTGGTATGGCTTCATTCAGCTCCGGTTCCCAACGATCAAGGCGAGTTACATGATCCCCC

3121 ATGTTGTGCAAAAAAGCGGTTAGCTCCTTCGGTCCTCCGATCGTTGTCAGAAGTAAGTTG

3181 GCCGCAGTGTTATCACTCATGGTTATGGCAGCACTGCATAATTCTCTTACTGTCATGCCA

3241 TCCGTAAGATGCTTTTCTGTGACTGGTGAGTACTCAACCAAGTCATTCTGAGAATAGTGT

3301 ATGCGGCGACCGAGTTGCTCTTGCCCGGCGTCAATACGGGATAATACCGCGCCACATAGC

3361 AGAACTTTAAAAGTGCTCATCATTGGAAAACGTTCTTCGGGGCGAAAACTCTCAAGGATC

3421 TTACCGCTGTTGAGATCCAGTTCGATGTAACCCACTCGTGCACCCAACTGATCTTCAGCA

3481 TCTTTTACTTTCACCAGCGTTTCTGGGTGAGCAAAAACAGGAAGGCAAAATGCCGCAAAA

3541 AAGGGAATAAGGGCGACACGGAAATGTTGAATACTCATACTCTTCCTTTTTCAATATTAT

3601 TGAAGCATTTATCAGGGTTATTGTCTCATGAGCGGATACATATTTGAATGTATTTAGAAA

3661 AATAAACAAATAGGGGTTCCGCGCACATTTCCCCGAAAAGTGCCACCTGACGTCTAAGAA

3721 ACCATTATTATCATGACATTAACCTATAAAAATAGGCGTATCACGAGGCCCTTTCGTC
```

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. The articles "a", "an", and "the" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses variations, combinations, and permutations in which one or more limitations, elements, clauses, descriptive terms, etc., from one or more of the claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth herein. It should also be understood that any embodiment of the invention, e.g., any embodiment found within the prior art, can be explicitly excluded from the claims, regardless of whether the specific exclusion is recited in the specification.

It should also be understood that, unless clearly indicated to the contrary, in any methods claimed herein that include more than one act, the order of the acts of the method is not necessarily limited to the order in which the acts of the method are recited, but the invention includes embodiments in which the order is so limited. Furthermore, where the claims recite a composition, the invention encompasses methods of using the composition and methods of making the composition.

INCORPORATION OF REFERENCES

All publications and patent documents cited in this application are incorporated by reference in their entirety to the same extent as if the contents of each individual publication or patent document were incorporated herein.

What is claimed is:

1. A modified DNA polymerase having a DNA polymerase activity comprising an amino acid sequence having at least 95% sequence identity to the amino acid sequence as set forth in SEQ ID NO: 16, or the amino acid sequence as set forth in, which amino acid sequence includes one or more amino acid substitutions relative to SEQ ID NO:16, such substitutions being selected from the group consisting of F752Y, F591L, F591I, E668V, G638R, G638V, E734K, E377K, T609I, T609A, P454S, E582K or G715R of SEQ ID NO: 16 and combinations thereof, wherein the one or more amino acid substitutions alter enzyme activity, fidelity, processivity, elongation rate, stability, or solubility.

2. A modified DNA polymerase having a DNA polymerase activity comprising the amino acid sequence as set forth in SEQ ID NO: 16 with one or more amino acid substitutions selected from the group consisting of F752Y, F591L, F591I, G638V, G638R, E668V, E734K, V356M, E738G, E386K, W772R, or E377K of SEQ ID NO: 16 and combinations thereof, wherein the one or more amino acid substitutions increase the enzyme activity of the DNA polymerase.

3. A modified DNA polymerase having a DNA polymerase activity comprising the amino acid sequence as set forth in SEQ ID NO: 16 with one or more amino acid substitutions selected from the group consisting of F591I, F591L, A550V, E377K, A494V, E734K, G638V, G638R, E668V, D346G, V356M or E738G of SEQ ID NO: 16 and combinations thereof, wherein the one or more amino acid substitutions increase the DNA binding affinity of the DNA polymerase.

4. A modified DNA polymerase having a DNA polymerase activity comprising the amino acid sequence as set forth in SEQ ID NO: 16 with one or more amino acid substitutions selected from the group consisting of R410H, E582K, E652K, A679T, S376G, or T680I of SEQ ID NO: 16 and combinations thereof, wherein the one or more amino acid substitutions decreases the DNA binding affinity of the DNA polymerase.

5. A modified DNA polymerase having a DNA polymerase activity comprising the amino acid sequence as set forth in SEQ ID NO: 16 with one or more amino acid substitutions selected from the group consisting of F591L, F752Y, F591I, E668V, V441I, G638R, S376G or T680I of SEQ ID NO: 16 and combinations thereof, wherein the one or more amino acid substitutions decreases the fidelity of the DNA polymerase.

6. The modified DNA polymerase of any one of claim 1, 2, 3, 4 or 5, wherein the DNA polymerase is a fusion polymerase.

7. A kit comprising the modified DNA polymerase of any one of claim 1, 2, 3, 4 or 5.

* * * * *

UNITED STATES PATENT AND TRADEMARK OFFICE
CERTIFICATE OF CORRECTION

| | | |
|---|---|---|
| PATENT NO. | : 8,481,685 B2 | Page 1 of 1 |
| APPLICATION NO. | : 13/127425 | |
| DATED | : July 9, 2013 | |
| INVENTOR(S) | : Bourn et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 238 days.

Signed and Sealed this
Twenty-sixth Day of November, 2013

Margaret A. Focarino
*Commissioner for Patents of the United States Patent and Trademark Office*

UNITED STATES PATENT AND TRADEMARK OFFICE
CERTIFICATE OF CORRECTION

PATENT NO.        : 8,481,685 B2
APPLICATION NO. : 13/127425
DATED             : July 9, 2013
INVENTOR(S)       : Bourn et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 239 days.

Signed and Sealed this
Eighth Day of September, 2015

Michelle K. Lee
*Director of the United States Patent and Trademark Office*